United States Patent
Greenberg et al.

(10) Patent No.: US 10,711,027 B2
(45) Date of Patent: Jul. 14, 2020

(54) DNA POLYMERASE BETA INHIBITORS

(71) Applicant: The Johns Hopkins University, Baltimore, MD (US)

(72) Inventors: Marc M. Greenberg, Baltimore, MD (US); Rakesh Paul, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/326,513

(22) PCT Filed: Aug. 11, 2017

(86) PCT No.: PCT/US2017/046534
§ 371 (c)(1),
(2) Date: Feb. 19, 2019

(87) PCT Pub. No.: WO2018/034987
PCT Pub. Date: Feb. 22, 2018

(65) Prior Publication Data
US 2019/0202853 A1 Jul. 4, 2019

Related U.S. Application Data

(60) Provisional application No. 62/377,028, filed on Aug. 19, 2016, provisional application No. 62/490,190, filed on Apr. 26, 2017.

(51) Int. Cl.
*C07H 19/10* (2006.01)
*C07H 3/04* (2006.01)
*A61P 35/00* (2006.01)

(52) U.S. Cl.
CPC .............. *C07H 19/10* (2013.01); *A61P 35/00* (2018.01); *C07H 3/04* (2013.01)

(58) Field of Classification Search
None
See application file for complete search history.

(56) References Cited

U.S. PATENT DOCUMENTS 9,029,346 B1 * 5/2015 Greenberg .............. C07H 19/10
514/42

FOREIGN PATENT DOCUMENTS

JP 2013-194044 9/2013
JP 2014-091731 5/2014

OTHER PUBLICATIONS

Absalon et al., Sequence-specific double-strand cleavage of DNA by Fe-bleomycin. 1. The detection of sequence-specific double-strand breaks using hairpin oligonucleotides. Biochemistry. Feb. 14, 1995;34(6):2065-75.

Absalon et al., Sequence-specific double-strand cleavage of DNA by Fe-bleomycin. 2. Mechanism and dynamics. Biochemistry. Feb. 14, 1995;34(6):2076-86.
Albertella et al., The overexpression of specialized DNA polymerases in cancer. DNA Repair (Amst). May 2, 2005;4(5):583-93.
Arian et al., Irreversible inhibition of DNA polymerase β by small-molecule mimics of a DNA lesion. J Am Chem Soc. Feb, 26, 2014;136(8):3176-83.
Asaeda et al., Highly sensitive assay of DNA abasic sites in mammalian cells—optimization of the aldehyde reactive probe method. Anal. Chim. Acta 1998;365:35-41.
Barakat et al., DNA polymerase beta (pol β) inhibitors: a comprehensive overview. Drug Discov Today. Aug. 2012;17(15-16):913-20.
Barakat et al., DNA repair inhibitors: the next major step to improve cancer therapy. Curr Top Med Chem. 2012;12(12):1376-9.
Beard et al., Structure and mechanism of DNA polymerase Beta. Chem Rev. Feb. 2006;106(2):361-82.
Boeckman et al., Direct enantioselective organocatalytic hydroxymethylation of aldehydes catalyzed by alpha,alpha-diphenylprolinol trimethylsilyl ether. Org Lett. Oct. 15, 2009;11(20):4544-7.
Bournaud et al., Organocatalyst-mediated enantioselective intramolecular Michael addition of aldehydes to vinyl sulfones. Tetrahedron: Asymmetry 2010;21(13-14):1666-73.
Braithwaite et al., DNA polymerases beta and lambda mediate overlapping and independent roles in base excision repair in mouse embryonic fibroblasts. PLoS One. Aug. 18, 2010;5(8):e12229.
Braithwaite et al.,DNA polymerase lambda mediates a back-up base excision repair activity in extracts of mouse embryonic fibroblasts. J. Biol. Chem. 2005;280:18469-18475.
Chen et al., Reconstructed evolutionary adaptive paths give polymerases accepting reversible terminators for sequencing and SNP detection. Proc Natl Acad Sci U S A. Feb. 2, 2010;107(5):1948-53.
Chung et al., Impact of linker strain and flexibility in the design of a fragment-based inhibitor. Nat Chem Biol. Jun. 2009;5(6):407-13.
Deterding et al., Mapping of the 5'-2-deoxyribose-5-phosphate lyase active site in DNA polymerase beta by mass spectrometry. J Biol Chem. Apr. 7, 2000;275(14):10463-71.
Dianov et al., Mammalian base excision repair: the forgotten archangel. Nucleic Acids Res. Apr. 1, 2013;41(6):3483-90.
Dizdaroglu, Oxidatively induced DNA damage and its repair in cancer. Mutat Res Rev Mutat Res. Jan.-Mar. 2015;763:212-45.
Donigan et al., Human POLB gene is mutated in high percentage of colorectal tumors. J Biol Chem. Jul. 6, 2012;287(28):23830-9.
Donigan et al., The human gastric cancer-associated DNA polymerase β variant D160N is a mutator that induces cellular transformation. DNA Repair (Amst). Apr. 1, 2012;11(4):381-90.
Donley et al., Small Molecule Inhibitors of 8-Oxoguanine DNA Glycosylase-1 (OGG1). ACS Chem Biol. Oct. 16, 2015;10(10):2334-43.
Dorjsuren et al., A real-time fluorescence method for enzymatic characterization of specialized human DNA polymerases. Nucleic Acids Res. Oct. 2009;37(19):e128.

(Continued)

*Primary Examiner* — Traviss C McIntosh, III
(74) *Attorney, Agent, or Firm* — Casimir Jones, S.C.; Jeffrey W. Childers

(57) ABSTRACT

Methods and compounds are disclosed for irreversibly inhibiting a DNA repair enzyme that possesses lyase activity.

22 Claims, 18 Drawing Sheets
Specification includes a Sequence Listing.

(56) References Cited

OTHER PUBLICATIONS

Dorjsuren et al., Diverse small molecule inhibitors of human apurinic/apyrimidinic endonuclease APE1 identified from a screen of a large public collection. PLoS One. 2012;7(10):e47974.
Feng et al., Deoxyribose phosphate excision by the N-terminal domain of the polymerase beta: the mechanism revisited. Biochemistry. Jul. 7, 1998;37(27):9605-11.
Fu et al., Balancing repair and tolerance of DNA damage caused by alkylating agents. Nat Rev Cancer. Jan. 12, 2012;12(2):104-20.
Gao et al., Inhibitors of DNA polymerase beta: activity and mechanism. Bioorg Med Chem. Apr. 15, 2008;16(8):4331-40.
Garcia-Diaz et al., Identification of an intrinsic 5'-deoxyribose-5-phosphate lyase activity in human DNA polymerase lambda: a possible role in base excision repair. J Biol Chem. Sep. 14, 2001;276(37):34659-63.
Gates et al., Biologically relevant chemical reactions of N7-alkylguanine residues in DNA. Chem Res Toxicol. Jul. 2004;17(7):839-56.
Gavande et al., DNA repair targeted therapy: The past or future of cancer treatment? Pharmacol Ther. Apr. 2016;160:65-83.
Goellner et al., Targeting DNA polymerase β for therapeutic intervention. Curr Mol Pharmacol. Jan. 2012;5(1):68-87.
Goldberg, Mechanism of neocarzinostatin action: role of DNA microstructure in determination of chemistry of bistranded oxidative damage. Acc. Chem. Res. 1991;24:191-198.
Gowda et al., Honokiol Inhibits DNA Polymerases β and λ and Increases Bleomycin Sensitivity of Human Cancer Cells. Chem Res Toxicol. Feb. 20, 2017;30(2):715-725.
Guan et al., Inhibition of short patch and long patch base excision repair by an oxidized abasic site. Biochemistry. Nov. 16, 2010;49(45):9904-10.
Guan et al., Irreversible inhibition of DNA polymerase beta by an oxidized abasic lesion. J Am Chem Soc. Apr. 14, 2010;132(14):5004-5.
Helleday et al., DNA repair pathways as targets for cancer therapy. Nat Rev Cancer. Mar. 2008;8(3):193-204.
Hong et al., Mild generation of 5-(2'-deoxyuridinyl)methyl radical from a phenyl selenide precursor. Org Lett. Dec. 23, 2004;6(26):5011-3.
Horton et al., Hypersensitivity of DNA polymerase beta null mouse fibroblasts reflects accumulation of cytotoxic repair intermediates from site-specific alkyl DNA lesions. DNA Repair (Amst). Jan. 2, 2003;2(1):27-48.
Horton et al., Involvement of DNA polymerase beta in protection against the cytotoxicity of oxidative DNA damage. DNA Repair (Amst). Apr. 29, 2002;1(4):317-33.
Horton et al., XRCC1 and DNA polymerase beta in cellular protection against cytotoxic DNA single-strand breaks. Cell Res. Jan. 2008;18(1):48-63.
Ide et al., Synthesis and damage specificity of a novel probe for the detection of abasic sites in DNA. Biochemistry. Aug. 17, 1993;32(32):8276-83.
Jacobs et al., Long patch base excision repair compensates for DNA polymerase β inactivation by the C4'-oxidized abasic site. Biochemistry. Jan. 11, 2011;50(1):136-43.
Jessen et al., Bioreversible protection of nucleoside diphosphates. Angew Chem Int Ed Engl. 2008;47(45):8719-22.
Jiang et al., Uracil-directed ligand tethering: an efficient strategy for uracil DNA glycosylase (UNG) inhibitor development. J Am Chem Soc. Dec. 14, 2005;127(49):17412-20.
Kodama et al., Preparation and analysis of oligonucleotides containing lesions resulting from C5'-oxidation. J Org Chem. Nov. 25, 2005;70(24):9916-24.
Kozarich et al., Sequence-specific isotope effects on the cleavage of DNA by bleomycin. Science. Sep. 22, 1989;245(4924):1396-9.
Kuriyama et al., Inhibitory effect of novel somatostatin peptide analogues on human cancer cell growth based on the selective inhibition of DNA polymerase β. Bioorg Med Chem. Jan. 15, 2013;21(2):403-11.

Kwarcinski et al., Irreversible inhibitors of c-Src kinase that target a nonconserved cysteine. ACS Chem Biol. Nov. 16, 2012;7(11):1910-7.
Lavrik et al., Binary system for selective photoaffinity labeling of base excision repair DNA polymerases. Nucleic Acids Res. Jul. 15, 2002;30(14):e73.
Liu et al., (2011) Links between DNA polymerase beta expression and sensitivity to bleomycin, Toxicology 281, 63-69.
Liu et al., An efficient method for the cleavage of p-methoxybenzylidene (PMP), tetrahydropyranyl (THP) and 1,3-dithiane protecting groups by Selectfluor$^{TM}$. Tetrahedron Lett. 2002;43:4037-4039.
Liu et al., Developing irreversible inhibitors of the protein kinase cysteinome. Chem Biol. Feb. 21, 2013;20(2):146-59.
Matsumoto et al., Catalytic center of DNA polymerase beta for excision of deoxyribose phosphate groups. Biochemistry. May 5, 1998;37(18):6456-64.
Matsumoto et al., Excision of deoxyribose phosphate residues by DNA polymerase beta during DNA repair. Science. Aug. 5, 1995;269(5224):699-702.
McGall et al., New insight into the mechanism of base propenal formation during bleomycin mediated DNA degradation. J. Am. Chem Soc. 1992;114:4958-4967.
Mootoo et al., n-Pentenyl glycosides permit the chemospecific liberation of the anomeric center. J. Am. Chem. Soc. 1988;110:2662-2663.
Nakamura et al., Chemical properties of fatty acid derivatives as inhibitors of DNA polymerases. Org Biomol Chem. Dec. 21, 2007;5(24):3912-21.
Neef et al., An azide-modified nucleoside for metabolic labeling of DNA, ChemBioChem 2014; 15:789-793.
Nemec et al., Colon cancer-associated DNA polymerase β variant induces genomic instability and cellular transformation. J Biol Chem. Jul. 6, 2012;287(28):23840-9.
Ora et al., Biodegradable protections for nucleoside 5'-monophosphates: comparative study on the removal of O-acetyl and O-acetyloxymethyl protected 3-hydroxy-2,2-bis(ethoxycarbonyl)propyl groups. J Org Chem. Jul. 17, 2009;74(14):4992-5001.
Pascucci et al., Reconstitution of the base excision repair pathway for 7,8-dihydro-8-oxoguanine with purified human proteins. Nucleic Acids Res. May 15, 2002;30(10):2124-30.
Paul et al., Synergistic Effects of an Irreversible DNA Polymerase Inhibitor and DNA Damaging Agents on HeLa Cells. ACS Chem Biol. Jun. 16, 2017;12(6):1576-1583.
Pitié et al., Activation of DNA carbon-hydrogen bonds by metal complexes. Chem Rev. Feb. 10, 2010;110(2):1018-59.
Polosina et al., 'Knock down' of DNA polymerase beta by RNA interference: recapitulation of null phenotype. DNA Repair (Amst). Nov. 2, 2004;3(11):1469-74.
Pourceau et al., Azide solid support for 3'-conjugation of oligonucleotides and their circularization by click chemistry. J Org Chem. Sep. 4, 2009;74(17):6837-42.
Prasad et al., Functional analysis of the amino-terminal 8-kDa domain of DNA polymerase beta as revealed by site-directed mutagenesis. DNA binding and 5'-deoxyribose phosphate lyase activities. J Biol Chem. May 1, 1998;273(18):11121-6.
Prasad et al., Human DNA polymerase beta deoxyribose phosphate lyase. Substrate specificity and catalytic mechanism. J Biol Chem. Jun. 12, 1998;273(24):15263-70.
Prasad et al., Structural insight into the DNA polymerase beta deoxyribose phosphate lyase mechanism. DNA Repair (Amst). Dec. 8, 2005;4(12):1347-57.
Rabow et al., Identification and quantitation of the lesion accompanying base release in bleomycin-mediated DNA degradation. J. Am. Chem. Soc. 1990;112:3196-3203.
Rai et al., Synthesis, biological evaluation, and structure-activity relationships of a novel class of apurinic/apyrimidinic endonuclease 1 inhibitors. J Med Chem. Apr. 12, 2012;55(7):3101-12.
Schermerhorn et al., A chemical and kinetic perspective on base excision repair of DNA. Acc Chem Res. Apr. 15, 2014;47(4):1238-46.
Sobol et al., Base excision repair intermediates induce p53-independent cytotoxic and genotoxic responses. J Biol Chem. Oct. 10, 2003;278(41):39951-9.

(56) References Cited

OTHER PUBLICATIONS

Sobol et al., Requirement of mammalian DNA polymerase-β in base-excision repair. Nature 1996;379:183-6.

Sobol et al., The lyase activity of the DNA repair protein beta-polymerase protects from DNA-damage-induced cytotoxicity. Nature. Jun. 15, 2000;405(6788):807-10.

Srivastava et al., DNA polymerase beta expression differences in selected human tumors and cell lines. Carcinogenesis. Jun. 1999;20(6):1049-54.

Starcevic et al., Is there a link between DNA polymerase beta and cancer? Cell Cycle. Aug. 2004;3(8):998-1001.

Stevens et al., DNA polymerase λ inactivation by oxidized abasic sites. Biochemistry. Feb. 5, 2013;52(5):975-83.

Stivers et al., A mechanistic perspective on the chemistry of DNA repair glycosylases. Chem Rev. Jul. 2003;103(7):2729-59.

Strittmatter et al., Expanding the Scope of Human DNA Polymerase λ and β Inhibitors. ACS Chem Biol. 2014;9:282-90.

Strittmatter et al., Small Molecule Inhibitors of Human DNA Polymerase λ. ACS Chem Biol. Apr. 15, 2011;6(4):314-9.

Sugiyama et al., Specific detection of C-4' hydroxylated abasic sites generated by bleomycin and neocarzinostatin in DNA, J. Am. Chem. Soc. 1990;112:5252-5257.

Trivedi et al., Human methyl purine DNA glycosylase and DNA polymerase beta expression collectively predict sensitivity to temozolomide. Mol Pharmacol. Aug. 2008;74(2):505-16.

Trivedi et al., The role of base excision repair in the sensitivity and resistance to temozolomide-mediated cell death. Cancer Res. Jul. 15, 2005;65(14):6394-400.

Wilson et al., Base excision repair and design of small molecule inhibitors of human DNA polymerase β. Cell Mol Life Sci. Nov. 2010;67(21):3633-47.

Wyatt et al., Methylating agents and DNA repair responses: Methylated bases and sources of strand breaks. Chem Res Toxicol. Dec. 2006;19(12):1580-94.

International Search Report and Written Opinion for PCT/US2017/046534, dated Nov. 27, 2017, 13 pages.

International Preliminary Report on Patentability for PCT/US2017/046534, dated Aug. 28, 2018, 41 pages.

* cited by examiner (a)   SEQ ID NO: 1
5'-d(TAA TGG CTA ACG CAA XAC GTA ATG CAG TCT)-³²P-3'
3'-d(ATT ACC GAT TGC GTT__ATG CAT TAC TGC AGA)
       SEQ ID NO: 2
                          X = dRP
*Fig. 7A*
(b)
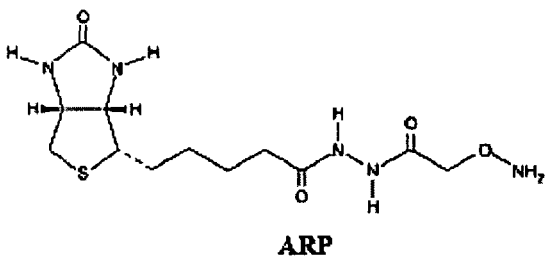
ARP
*Fig. 7B*
(c)  hv    +  +  +     +  -
     NaOH  -  -  -     +  -
     NaBH₄ +  -  +     -  -
     ARP   +  +  -     -  -
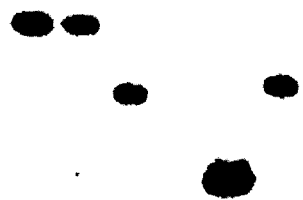
*Fig. 7C*

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial sequence
<220> FEATURE:
<223> OTHER INFORMATION: Synthetic

<400> SEQUENCE: 1
taatggctaa cgcaaacgta atgcagtct                              29

<210> SEQ ID NO 2
<211> LENGTH: 30
<212> TYPE: DNA
<213> ORGANISM: Artificial sequence
<220> FEATURE:
<223> OTHER INFORMATION: Synthetic

<400> SEQUENCE: 2
agacgtcatt acgtattgcg ttagccatta                             30

<210> SEQ ID NO 3
<211> LENGTH: 29
<212> TYPE: DNA
<213> ORGANISM: Artificial sequence
<220> FEATURE:
<223> OTHER INFORMATION: Synthetic

<400> SEQUENCE: 3
tcaccctcgt acgactcttt tttttttgc                              29
```

```
<210> SEQ ID NO 4
<211> LENGTH: 29
<212> TYPE: DNA
<213> ORGANISM: Artificial sequence
<220> FEATURE:
<223> OTHER INFORMATION: Synthetic

<400> SEQUENCE: 4
gcaaaaaaaa aagagtcgta cgagggtga                                      29

<210> SEQ ID NO 5
<211> LENGTH: 30
<212> TYPE: DNA
<213> ORGANISM: Artificial sequence
<220> FEATURE:
<223> OTHER INFORMATION: Synthetic

<400> SEQUENCE: 5
cgaccggctc gtatgtgtgt ggagctgtgg                                     30

<210> SEQ ID NO 6
<211> LENGTH: 31
<212> TYPE: DNA
<213> ORGANISM: Artificial sequence
<220> FEATURE:
<223> OTHER INFORMATION: Synthetic

<400> SEQUENCE: 6
ccacagctcc acacaacata cgagccggtc g                                   31
```

DNA POLYMERASE BETA INHIBITORS

CROSS-REFERENCE TO RELATED APPLICATIONS

This application is a § 371 U.S. National Entry Application of International Application PCT/US2017/046534, filed Aug. 11, 2017, which claims the benefit of U.S. Provisional Application Nos. 62/377,028 filed Aug. 19, 2016, and 62/490,190 filed Apr. 26, 2017, each of which are incorporated herein by reference in their entirety.

FEDERALLY SPONSORED RESEARCH OR DEVELOPMENT

This invention was made with government support under GM063028 awarded by the National Institutes of Health. The government has certain rights in the invention.

SEQUENCE LISTING

The text of the computer readable sequence listing filed herewith, titled "36570-253_SEQUENCE_LISTING_ST25", created May 19, 2020, having a file size of 2,000 bytes, is hereby incorporated by reference in its entirety.

BACKGROUND

Base excision repair (BER) is a primary mechanism for maintaining genome integrity. A large variety of modified nucleotides resulting from DNA oxidation and alkylation are removed by glycosylases (Friedberg et al., 2006). Abasic (AP) sites are ubiquitous DNA lesions that are mutagenic and cytotoxic. Some BER glycosylases are bifunctional and cleave DNA at a transiently formed AP site via a lyase process (Stivers et al, 2003). In other instances, AP sites are produced as metastable intermediates. AP sites also are generated via spontaneous hydrolysis of native and damaged nucleotides.

DNA polymerase β (Pol β), a bifunctional enzyme that contains an 8 kDa lyase active site separate from its polymerase active site (Matsumoto and Kim, 1995; Matsumoto et al., 1998; Prasad et al., 1998), plays an integral role in BER by excising the remnant of an AP site following 5'-incision by apurinic endonuclease I (Ape1), and subsequently filling in the single nucleotide gap (Scheme 1).

Scheme 1. Role of DNA polymerase β (Pol β) in base excision repair.

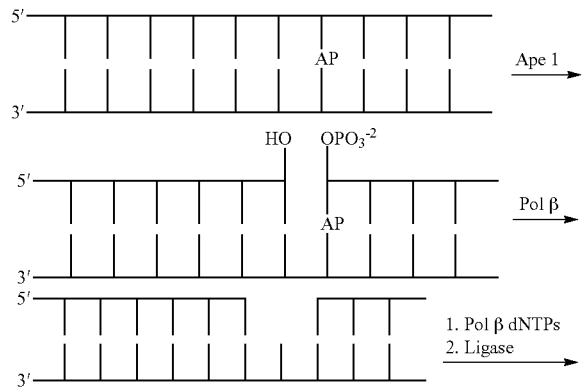

Pol β excises the 5'-phosphorylated 2-deoxyribose (dRP) produced upon Ape1 incision of DNA containing an AP site (Scheme 2). Lys72 is the primary amine responsible for Schiff base formation, although the enzyme retains some lyase activity when this amino acid is mutated (Deterding et al., 2000; Prasad et al., 2005; Prasad et al., 1998; Feng et al., 1998). Lys84, which also is present in the lyase active site, is postulated to substitute for Lys72 in the mutated enzyme, albeit with much lower efficiency. Following Schiff base formation, dRP elimination leaves a single nucleotide gap that contains the appropriate end groups for DNA synthesis (by Pol β) and ligation to complete repair (Scheme 1, above).

Scheme 2. Role of Pol β in excising the dRP produced upon Ape1 incision of DNA containing an AP site.

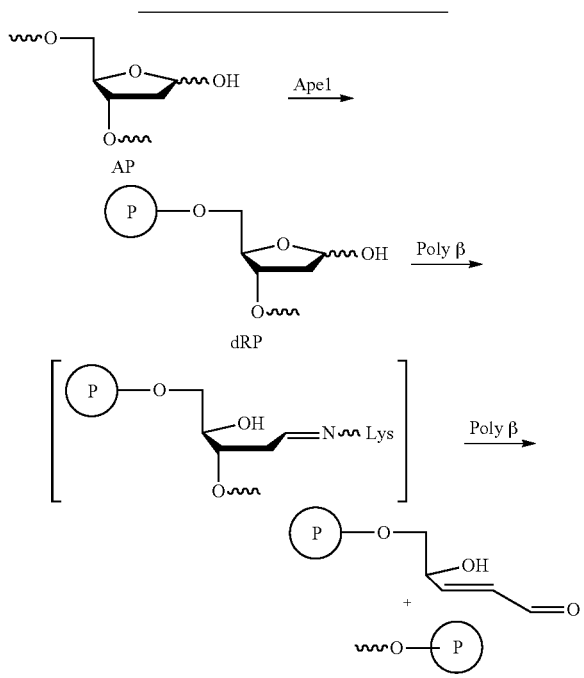

Part of the attraction of Pol β as a potential therapeutic target is that it is over expressed in a variety of cancer cells (Husain et al., 1999; Starcevic et al., 2004; Barakat et al., 2012). In addition, Pol β variants are found in a large percentage of tumors (Donigan et al., 2012a; Nemec et al., 2012; Donigan et al., 2012b). Some of the variants exhibit reduced activity and may contribute to tumorigenesis by decreasing genomic stability. In addition, Pol β's vitality to genome integrity is manifested by the observation that cells lacking both alleles of the gene for this enzyme are embryonic lethal and knocking down Pol β activity sensitizes cells to DNA damaging agents (Horton et al., 2008). Consequently, Pol β has attracted interest as a target for antitumor therapy. Inhibiting Pol β potentiates the cytotoxic effects of DNA damaging agents and can be cytotoxic in its own right.

Natural and unnatural products have been tested as inhibitors of Pol β and the related enzyme, Pol λ, which is believed to act as a back up for Pol β in BER (Braithwaite et al., 2010; Braithwaite et al., 2005; Gao et al., 2008; Nakamura et al., 2007; Strittmatter et al., 2011; Wilson et al., 2010). Some of these molecules are believed to target the lyase domain. There is an interaction between Pol β and a DNA lesion, dioxobutane (DOB), which is produced by a family of potent cytotoxic antitumor antibiotics following C5'-hydrogen atom abstraction (Pitié and Pratviel, 2010; Goldberg, 1991). DOB efficiently inactivates Pol β (and Pol λ) (Guan and Greenberg, 2010; Guan et al., 2010; Stevens et al., 2013). Radiolabeling experiments, liquid chromatography, and mass spectral analyses of protease digests indicate that the 1,4-dicarbonyl inactivates Pol β in two ways (Scheme 3).

Scheme 3. Inactivation of Pol β by DOB.

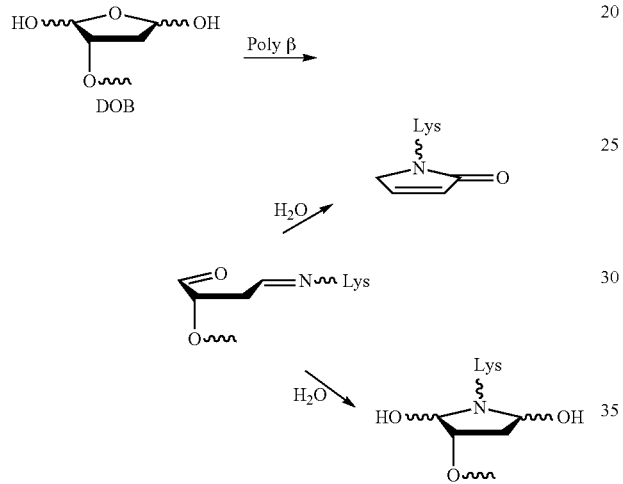

DOB forms a stable lactam following condensation with Lys72 or Lys84, elimination, and dehydration. The lesion also forms a stable adduct without undergoing DNA cleavage. The pC4-AP that is produced upon Ape1 incision of C4-AP (structures below) also contains a 1,4-dicarbonyl and inactivates Pol β and Pol λ (Stevens et al., 2013; Jacobs et al., 2011).

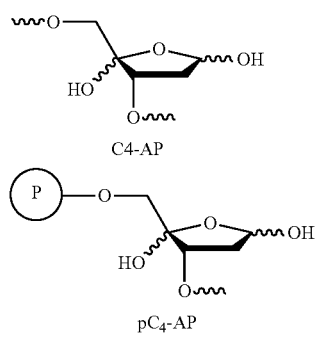

SUMMARY

In some aspects, the presently disclosed subject matter provides a compound of formula (I):

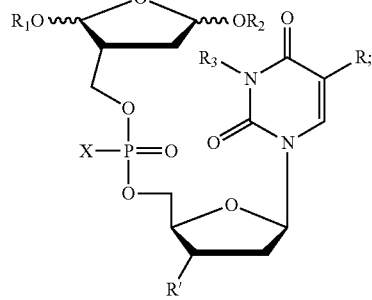

(I)

wherein: X is selected from the group consisting of alkyl, alkoxyl, O⁻, and S⁻;

R is selected from the group consisting of —CH₃ and

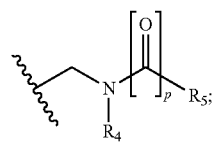

R' is selected from the group consisting of —NR₆R₇ and

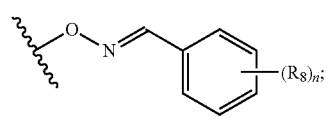

with the proviso that if R is —CH₃, then R' is —NR₆R₇; $R_1$ and $R_2$ are each independently selected from the group consisting of hydrogen and —C(=O)-alkyl; $R_3$ and $R_4$ are each independently selected from the group consisting of hydrogen or $C_1$-$C_6$ alkyl; $R_5$, $R_6$ and $R_7$ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof; each $R_8$ is independently selected from the group consisting of halogen, hydroxyl, alkyl, alkenyl, alkynyl, alkoxyl, sulfhydryl, sulfide, and carboxyl; n is an integer selected from the group consisting of 0, 1, 2, 3, 4, and 5; p is an integer selected from the group consisting of 0 and 1; and pharmaceutically acceptable salts thereof.

In other aspects, the presently disclosed subject matter provides a method for irreversibly inhibiting a DNA repair enzyme that possesses lyase activity in a subject, the method comprising administering to the subject a therapeutically effective amount of a compound of Formula (I) and pharmaceutically acceptable salts thereof.

In yet other aspects, the presently disclosed subject matter provides a method for inhibiting a cancer cell, the method comprising contacting the cancer or noncancerous cell with a compound of Formula (I) in an amount effective to irreversibly inhibit a DNA repair enzyme that possesses lyase activity, thereby inhibiting the cancer cell.

In still yet other aspects, the presently disclosed subject matter provides a method for irreversibly inhibiting a DNA repair enzyme that possesses lyase activity, the method comprising contacting the DNA repair enzyme with a compound of Formula (I) wherein contacting the DNA repair enzyme with the compound irreversibly inhibits the DNA repair enzyme.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
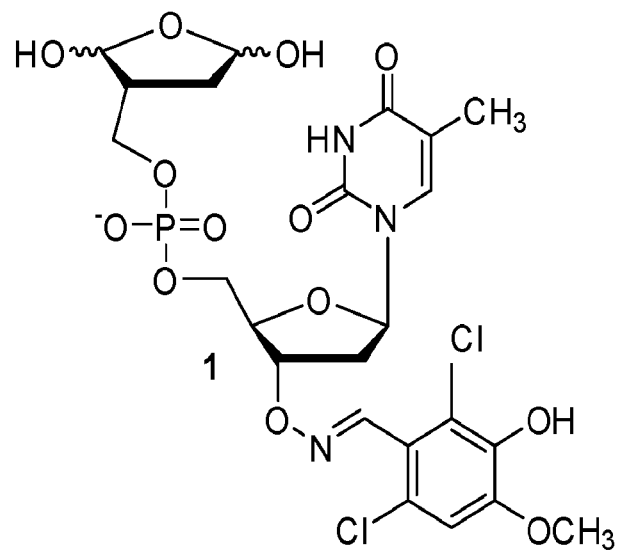
Figure 1:
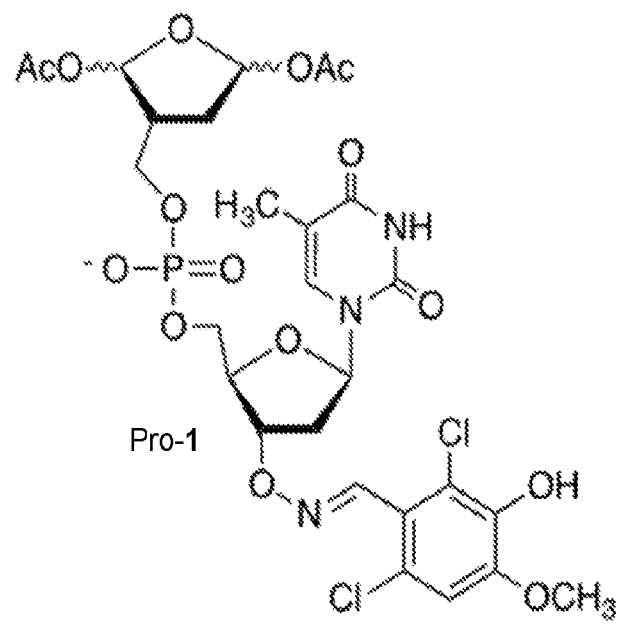
Figure 2:
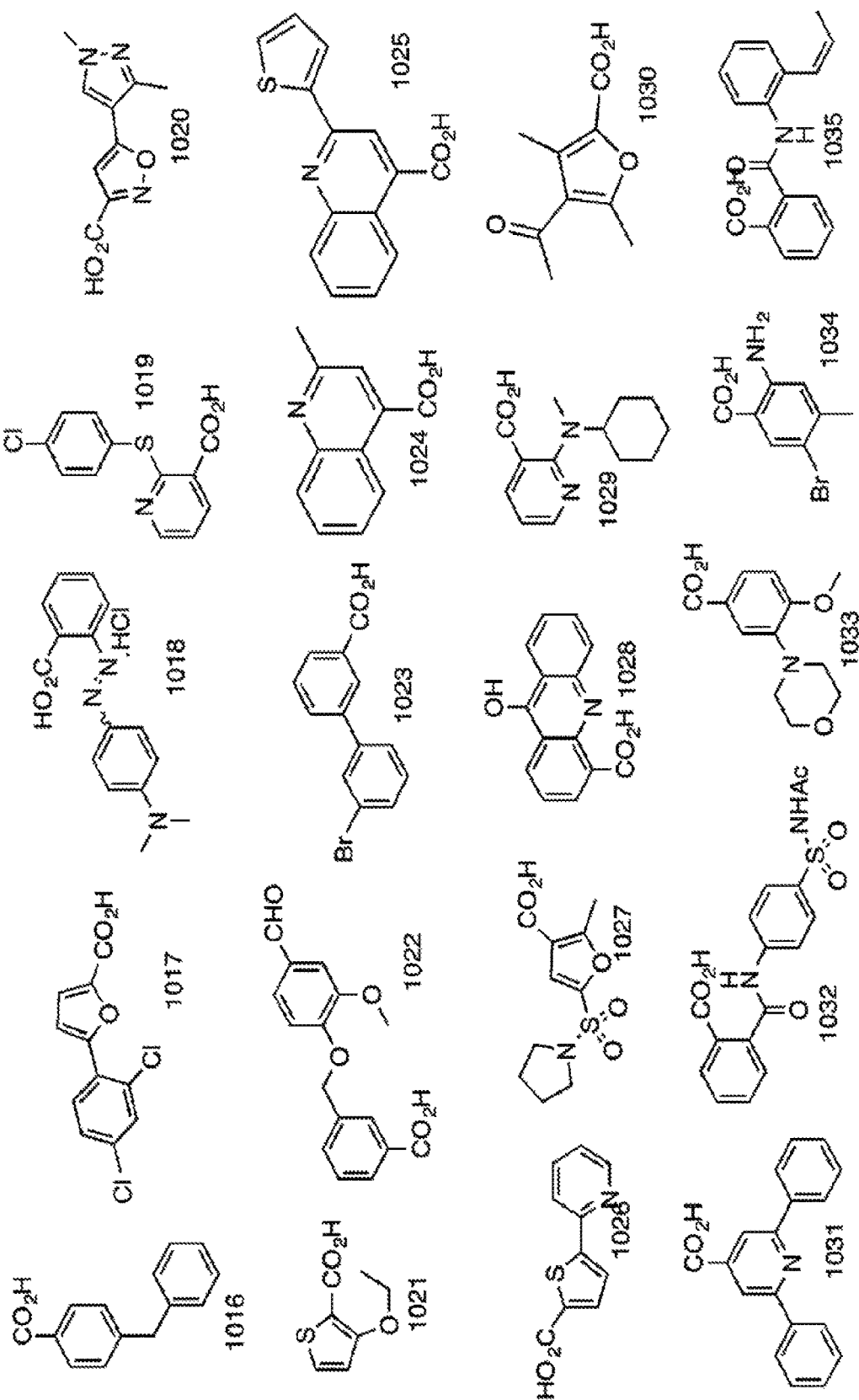
Figure 2:
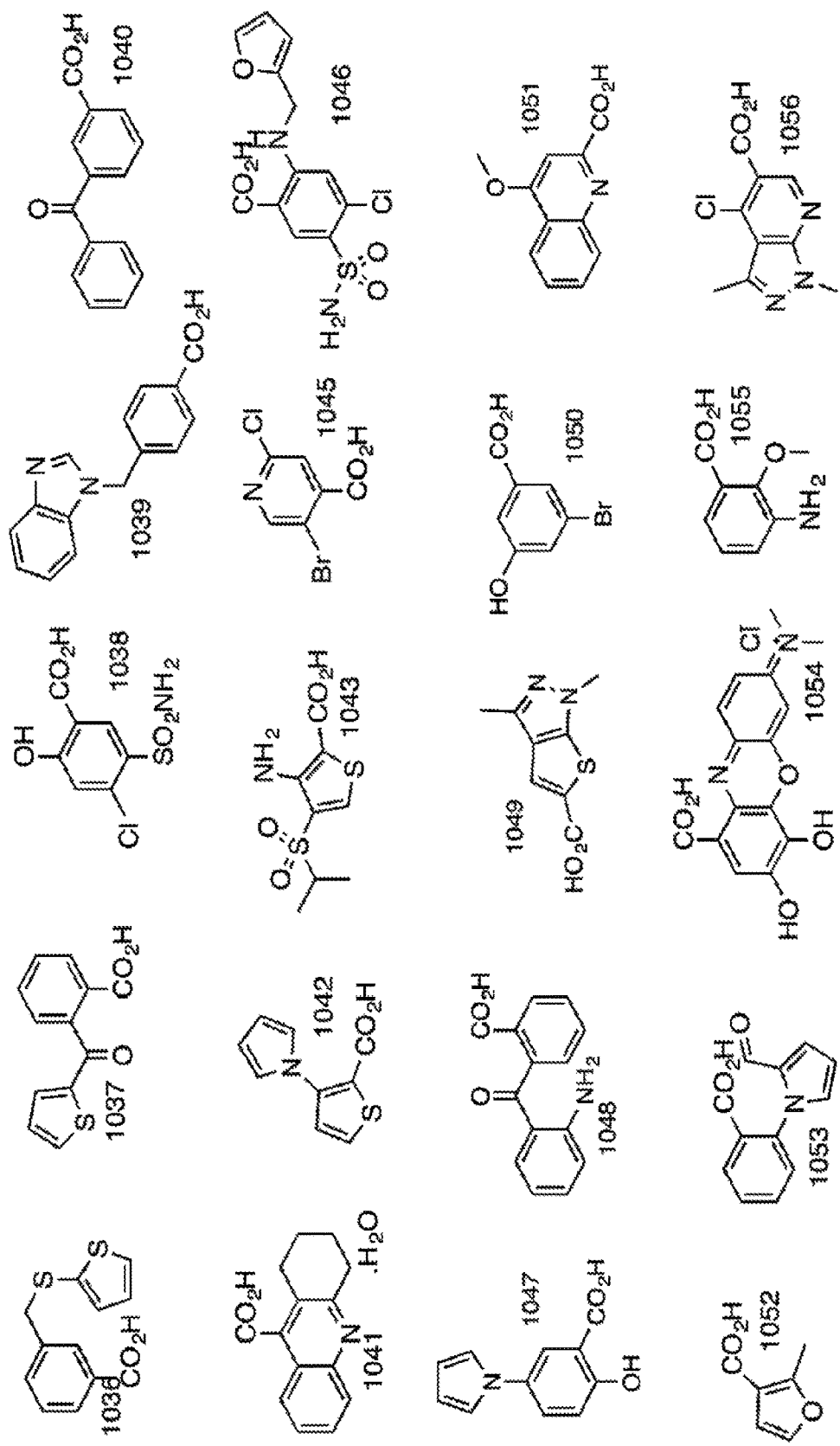
Figure 2:
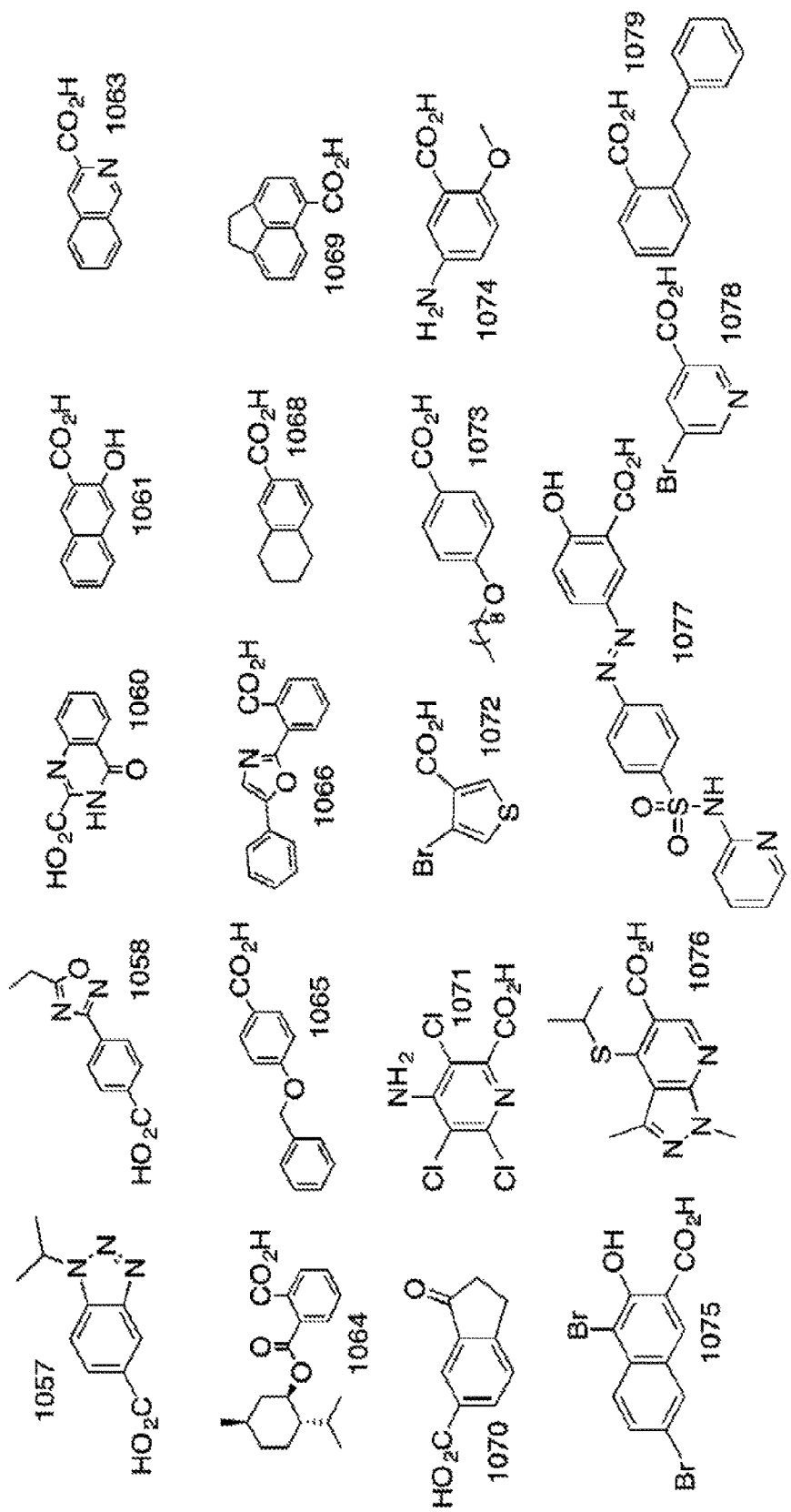
Figure 2:
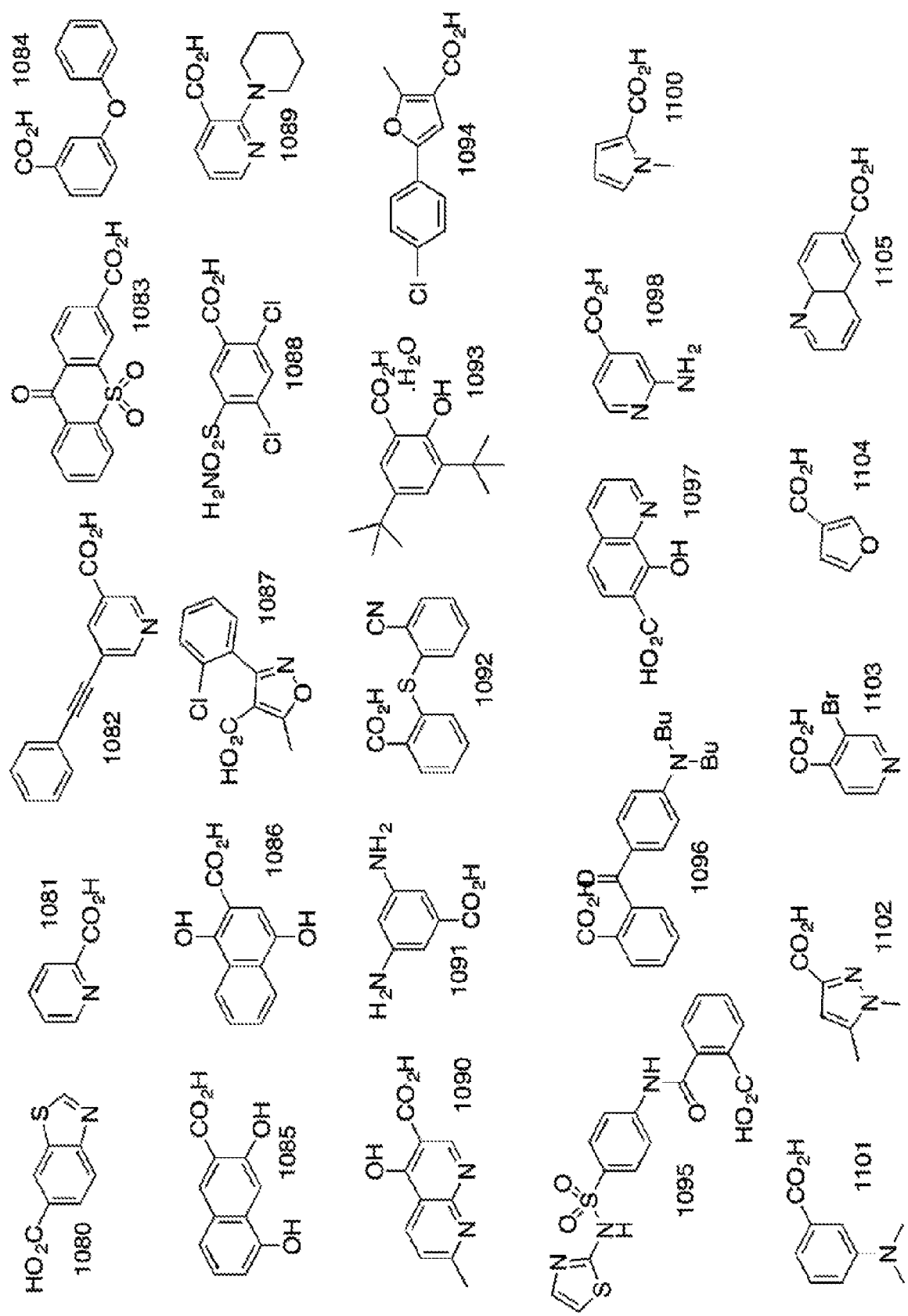
Figure 2:
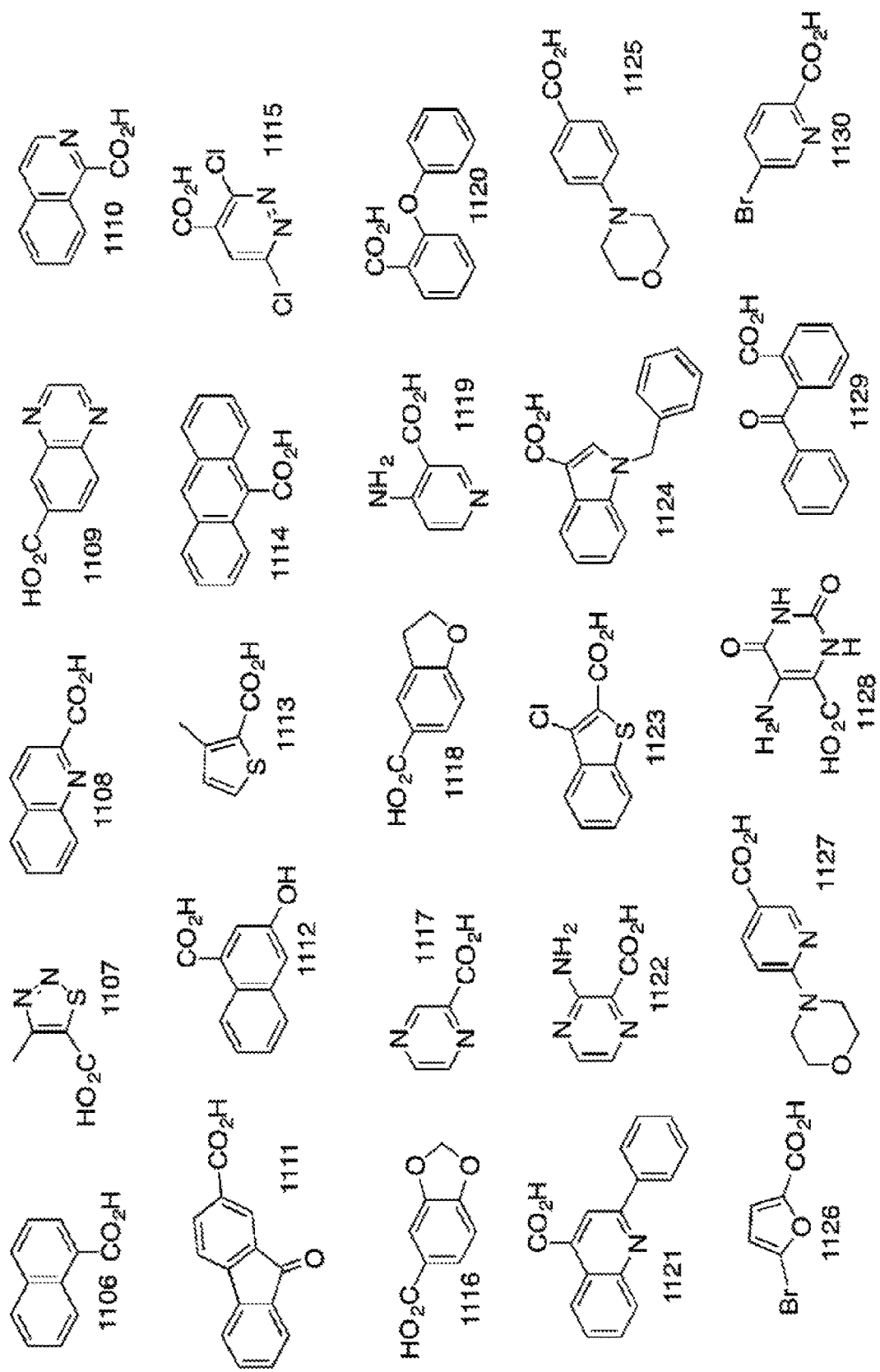
Figure 2:
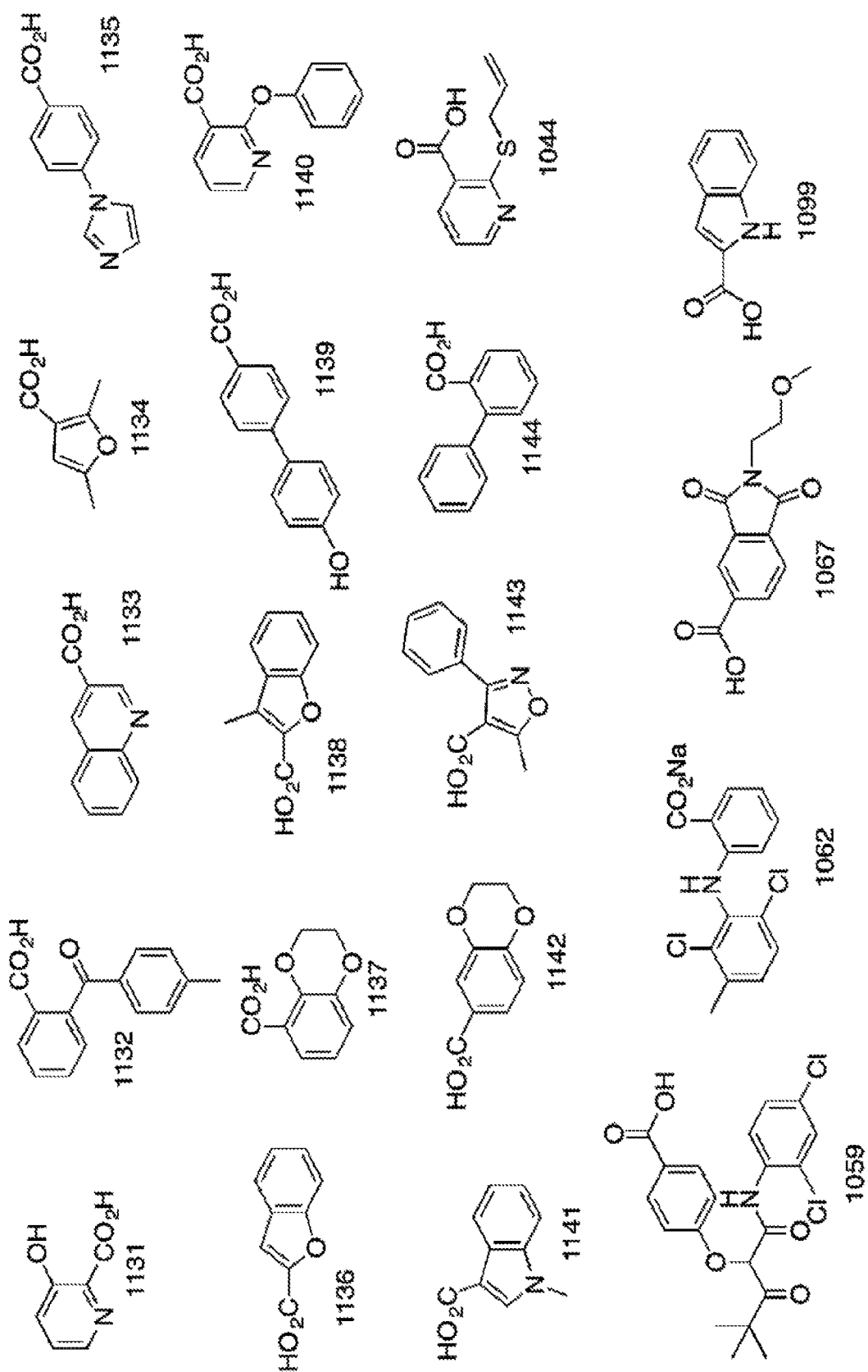
Figure 5:
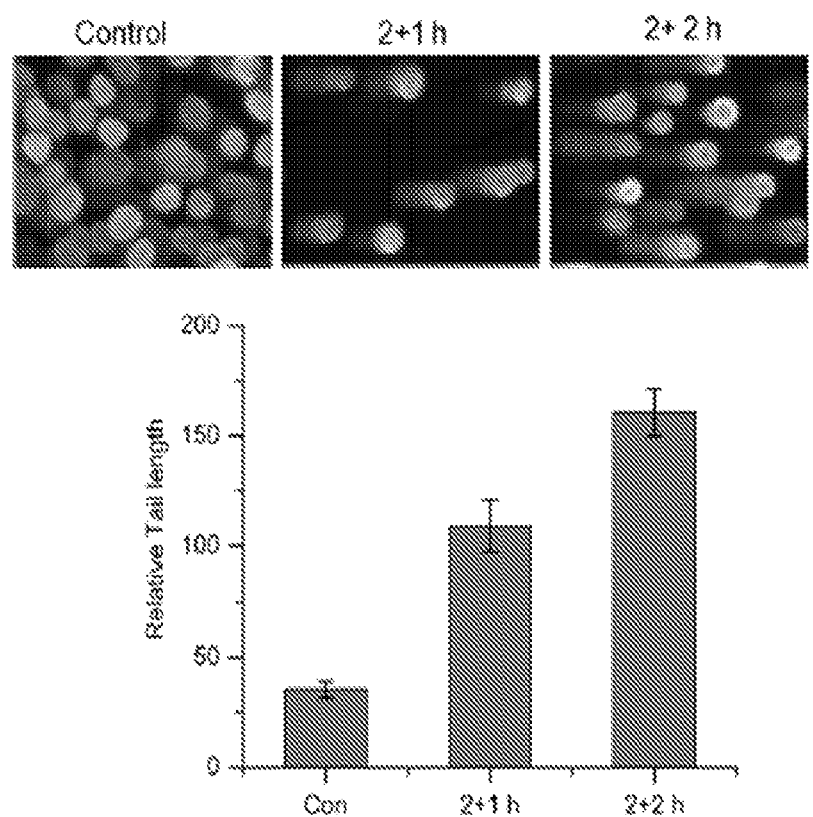
Figure 6:
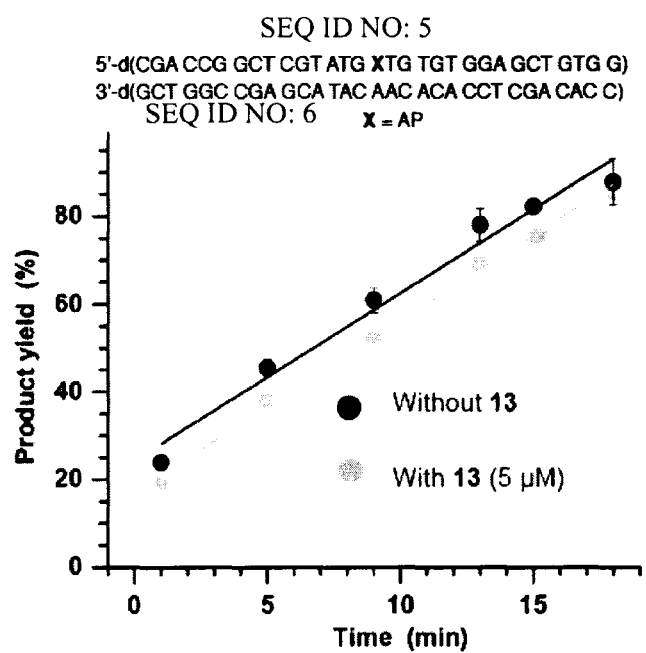
Figure 6:
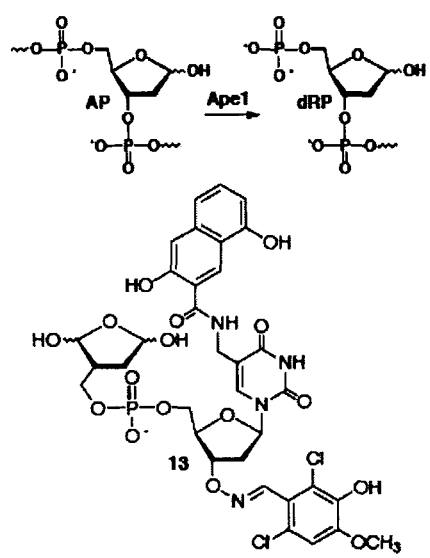
Figure 8:
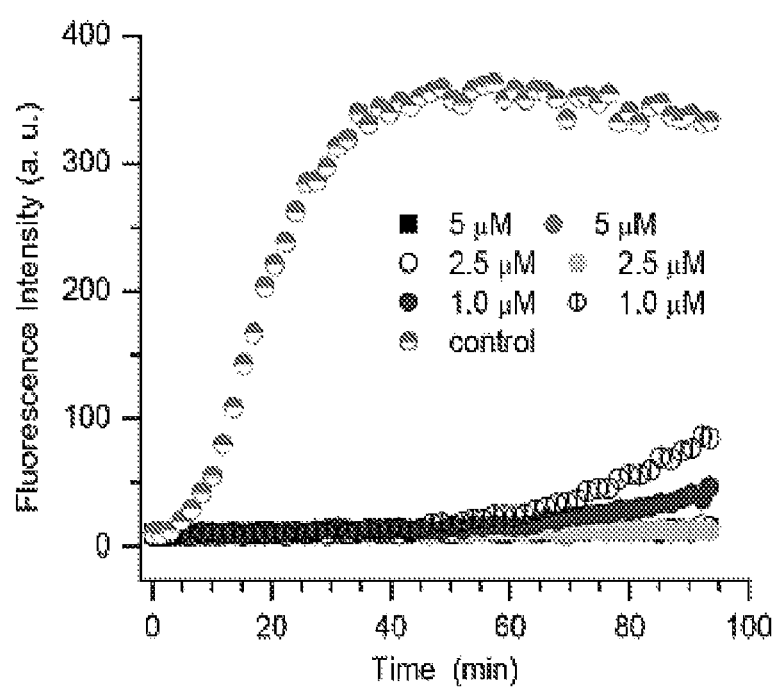
Figure 9:
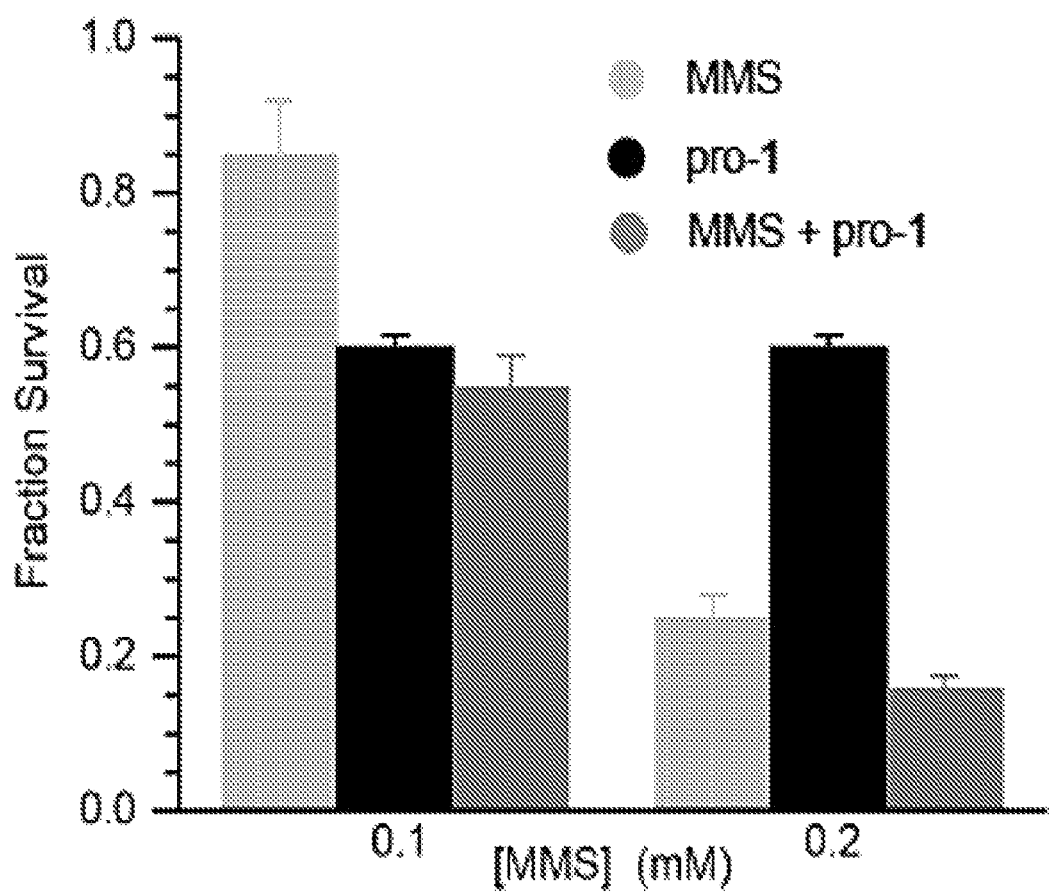
Figure 10:
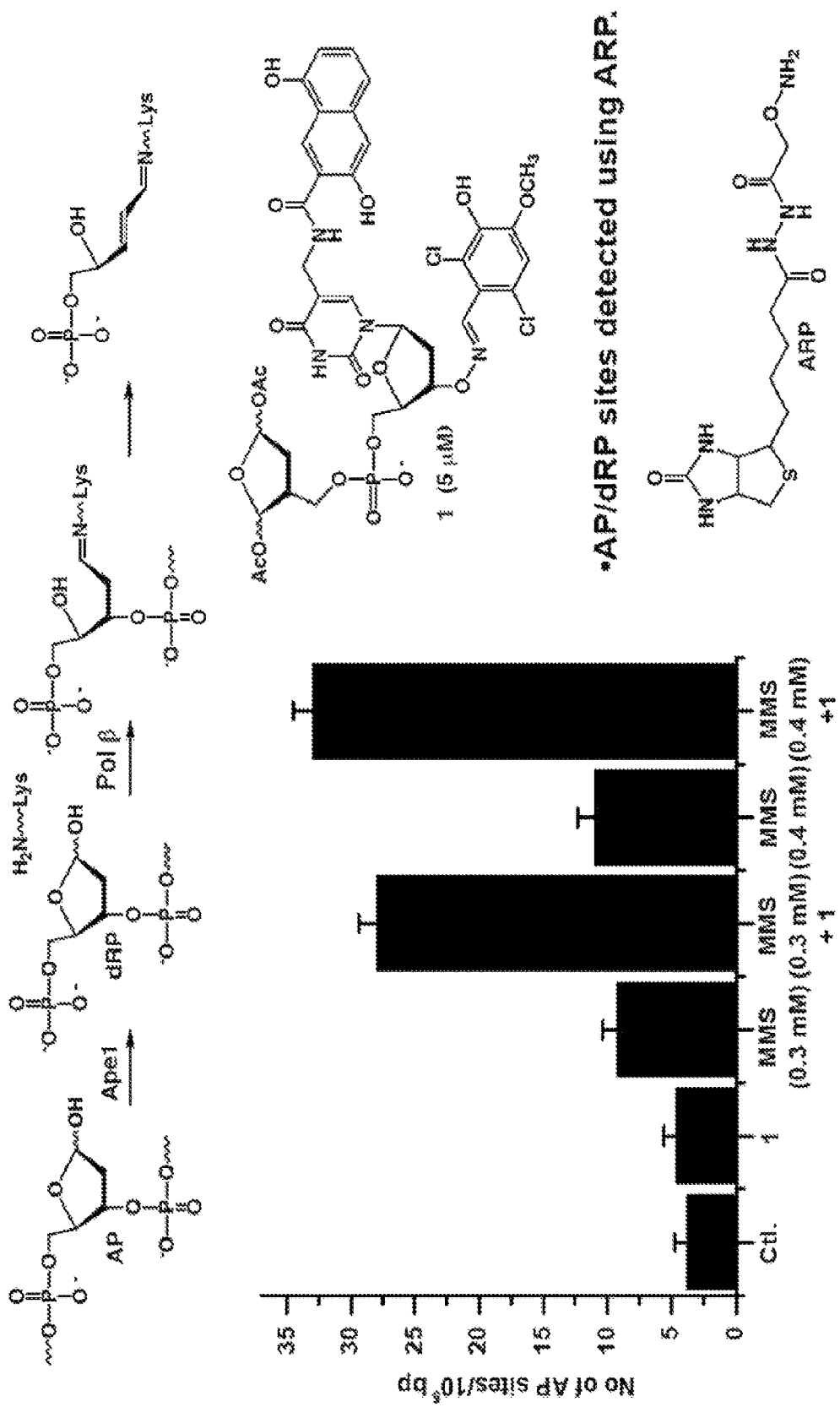

Having thus described the presently disclosed subject matter in general terms, reference will now be made to the accompanying Figures, which are not necessarily drawn to scale, and wherein:

FIG. 1 shows examples of previously reported DNA polymerase beta inhibitors (prior art);

FIG. 2 shows the structures of representative carboxylic acids used to create the presently disclosed library of DNA polymerase beta inhibitors;

FIG. 3A, FIG. 3B, FIG. 3C, and FIG. 3D show irreversible inhibition by 13: (FIG. 3A) normalized lyase activity of Pol β prior to and after dialysis (24 h) following incubation with or without 13 (3 μM); (FIG. 3B) relative Pol β lyase activity as a function of [13] and preincubation time of inhibitor with enzyme; (FIG. 3C) $IC_{50}$ of 13 on Pol β; and (FIG. 3D) $IC_{50}$ of 13 on Pol λ;

FIG. 4A, FIG. 4B, FIG. 4C, and FIG. 4D show potentiation of DNA damaging agent cytotoxicity in HeLa cells by pro-13 (5 μM): (FIG. 4A) MMS (0.1 mM); (FIG. 4B) MMS (0.2 mM); (FIG. 4C) BLM (2 μM); and (FIG. 4D) effect of pro-13 on HeLa cell cytotoxicity during recovery time following removal of the MMS. Black bars: MMS (0.1 mM), 2 h; Light gray bars: MMS (0.1 mM)+pro-13, 2 h; Dark gray bars: MMS (0.1 mM)+pro-13 for 2 h, followed by additional incubation with pro-13 for the recovery time shown. Values shown are the ave.±std. dev. of 3 replicates;

FIG. 5 shows detection of DNA damage in HeLa cells treated with bleomycin. (Top) A representative image showing increase in the tail length due to BLM treatment. (Bottom) Quantification of the relative tail lengths in the HeLa cells incubated with BLM (2 μM) for 2 h followed by 1 h (2+1 h) and 2 h (2+2 h) recovery. (Con: BLM untreated control);

FIG. 6 shows the effect of 13 on Ape1 activity;

FIG. 7A, FIG. 7B, and FIG. 7C demonstrate that ARP reacts with dRP in 15: (FIG. 7A) dRP containing 3'-32P-15; (FIG. 7B) the aldehyde reactive probe (ARP); and (FIG. 7C) 20% Denaturing PAGE gel diagram showing the dRP-ARP adduct formation with other controls;

FIG. 8 shows the concentration dependence of the effect of 13 on strand displacement synthesis in 14 by Pol β measured via fluorescence;

FIG. 9 shows HeLa cell cytoxicity following treatment with MMS and/or pro-13 (5 μM) for 2 h; and FIG. 10 shows abasic site repair is inhibited in HeLa cells by proinhibitor 13.

Figure 11:
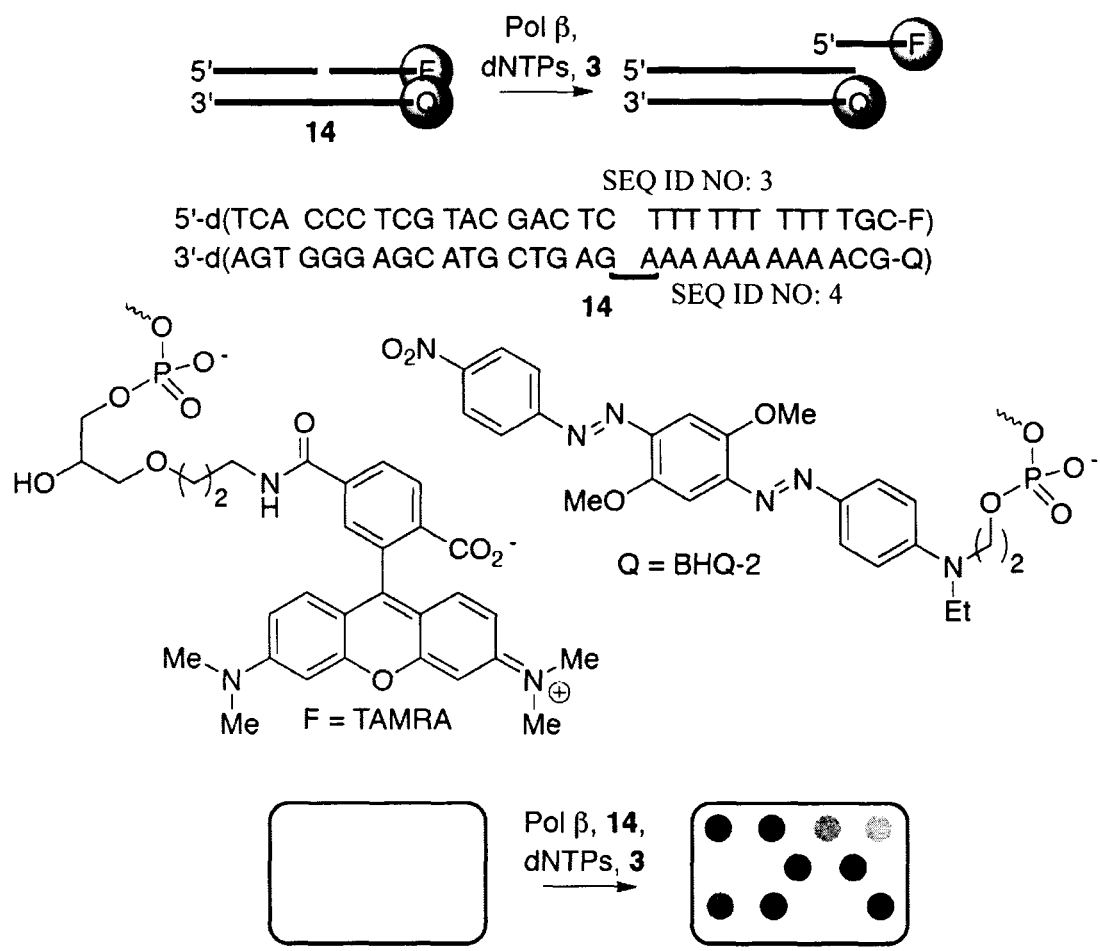

FIG. 11 shows Scheme 9 a fluorescence screen for inhibitors, specifically the identification and characterization of a Pol β Inhibitor (13). Inhibitor candidates (n=130) were screened using a previously reported assay that capitalizes on the ability of Pol β to carry out strand displacement synthesis on substrate 14.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Irreversible Inhibitors of DNA Polymerase Beta

The presently disclosed subject matter provides DNA repair enzyme inhibitors that irreversibly inactivate a DNA repair enzyme. In some embodiments, irreversible inactivation occurs by targeting the lyase active site of the DNA repair enzyme. In particular embodiments, the DNA repair enzyme is DNA polymerase β (Guan and Greenberg, 2010; Guan et al., 2010; Stevens et al., 2013; Jacobs et al., 2011). It is believed that the presently disclosed compounds represent the most potent inhibitors known to target the lyase domain of DNA polymerase β.

As used herein, the term "DNA repair enzyme" includes an enzyme that can repair changes or mutations in DNA and restore the DNA to its original state. The presently disclosed method is applicable for various DNA repair enzymes that possess lyase activity. As used herein, the term "lyase activity" means an activity that involves the removal of a group from a double bond or the addition of a group to a double bond. Accordingly, in some embodiments, the compound inhibits the lyase activity of the DNA repair enzyme.

Non-limiting examples of DNA repair enzymes suitable for use with the presently disclosed methods include DNA polymerase β (UniProt Accession No. P06746, for example), 5'-deoxyribose-5-phosphate lyase Ku70 (UniProt Accession No. P12956, for example), Endonuclease III-like protein 1 (UniProt Accession No. P78549, for example), DNA polymerase λ (Pol λ), DNA polymerase θ (Pol θ), and the like. In some embodiments, the DNA repair enzyme is selected from the group consisting of DNA polymerase β, 5'-deoxyribose-5-phosphate lyase Ku70, and Endonuclease III-like protein 1.

A. Compounds of Formula (I)

In some embodiments, the presently disclosed subject matter provides a compound of formula (I):

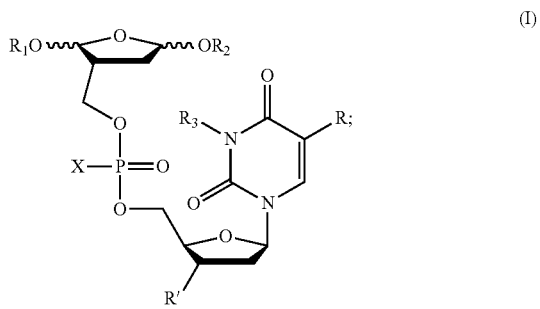

wherein: X is selected from the group consisting of alkyl, alkoxyl, O⁻, and S⁻;

R is selected from the group consisting of —CH₃ and

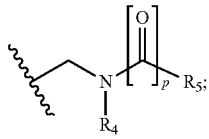

R' is selected from the group consisting of —NR₆R₇

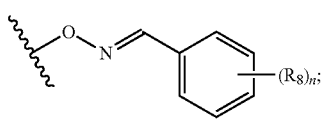

with the proviso that if R is —CH₃, then R' is —NR₆R₇; $R_1$ and $R_2$ are each independently selected from the group consisting of hydrogen and —C(=O)-alkyl; $R_3$ and $R_4$ are each independently selected from the group consisting of hydrogen or $C_1$-$C_6$ alkyl; $R_5$, $R_6$ and $R_7$ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof; each $R_8$ is independently selected from the group consisting of halogen, hydroxyl, alkyl, alkenyl, alkynyl, alkoxyl, sulfhydryl, sulfide, and carboxyl; n is an integer selected from the group consisting of 0, 1, 2, 3, 4, and 5; p is an integer selected from the group consisting of 0 and 1; and pharmaceutically acceptable salts thereof.

In some embodiments, the compound of formula (I) is selected from the group consisting of:

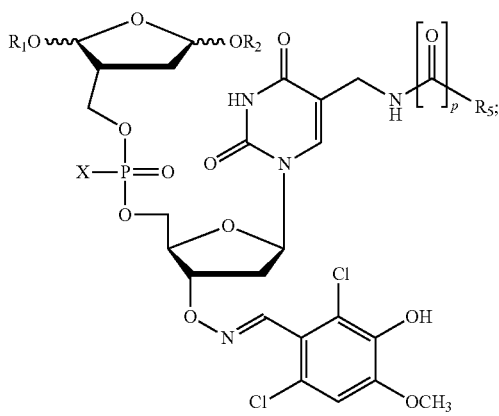

(Ia)

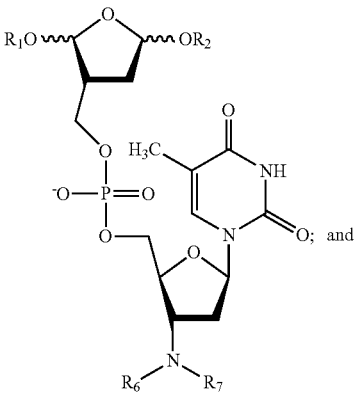

(Ib)

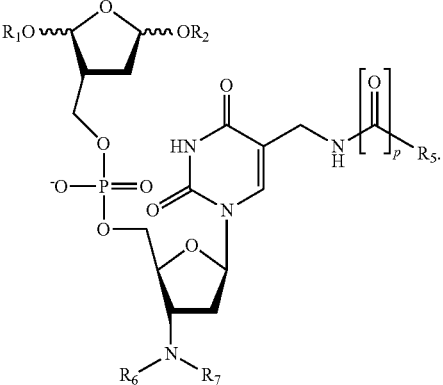

(Ic)

In particular embodiments, $R_5$ is selected from the group consisting of:

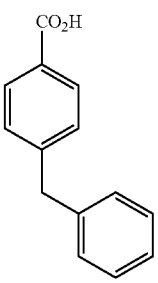

1016

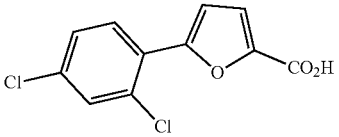

1017

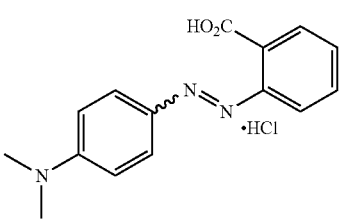

1018

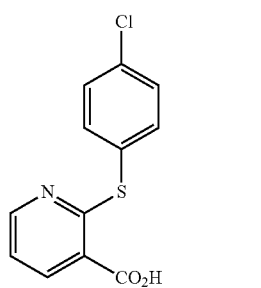
1019
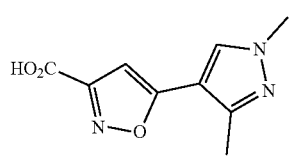
1020
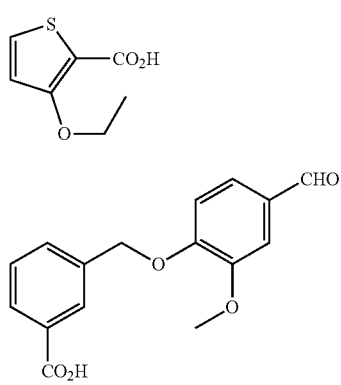
1021
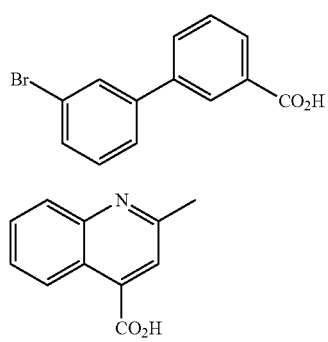
1022
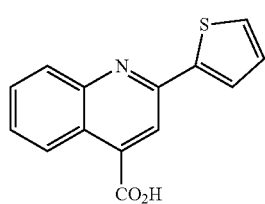
1023
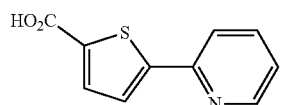
1024
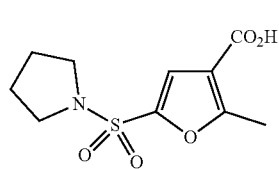
1025
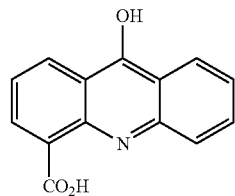
1028
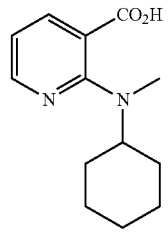
1029
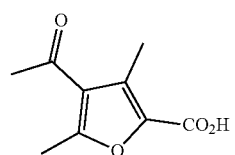
1030
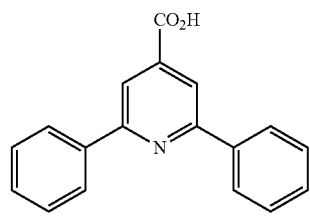
1031
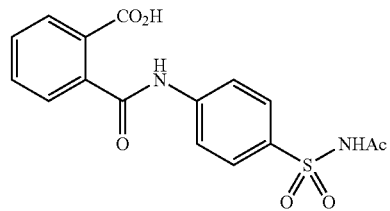
1032
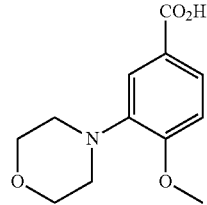
1033
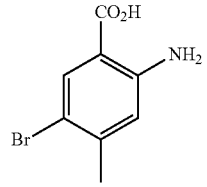
1034
1035

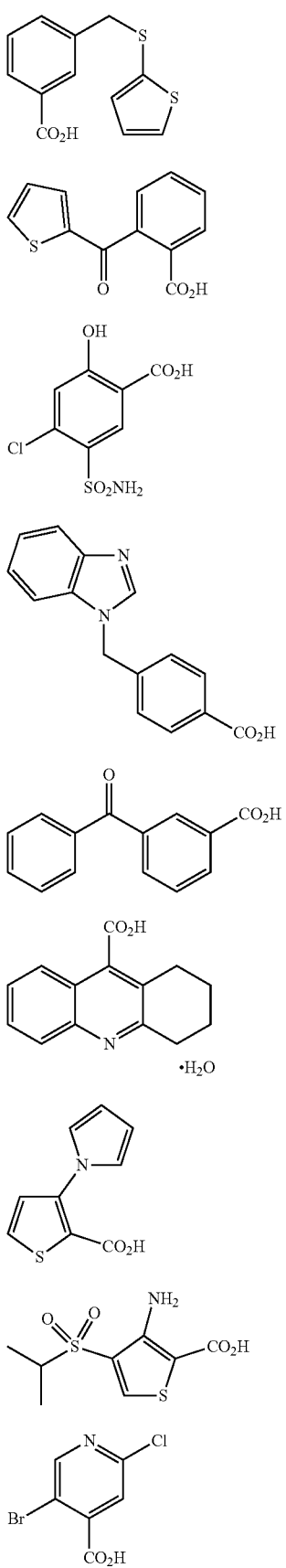
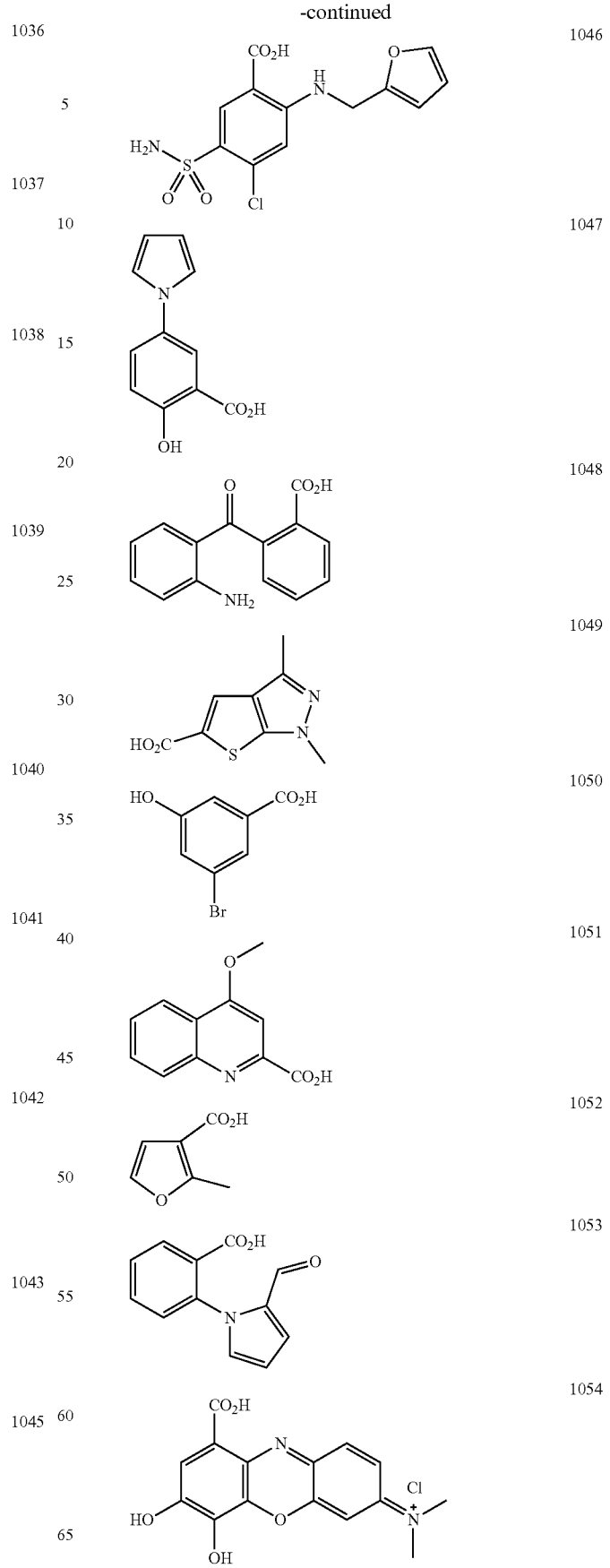

-continued
1055 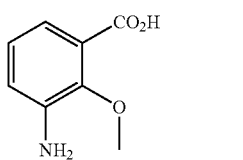
1056 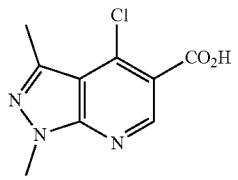
1057 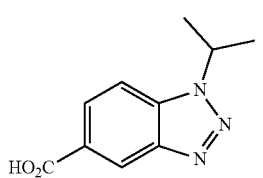
1058 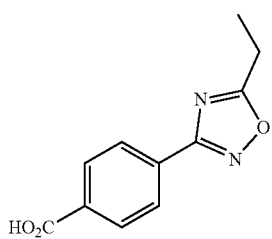
1060 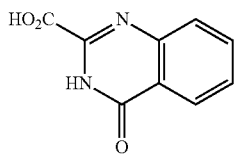
1061 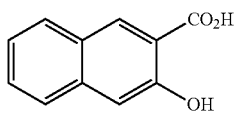
1063 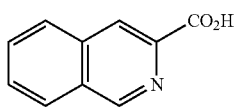
1064 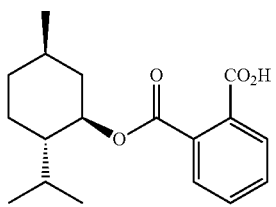
1065 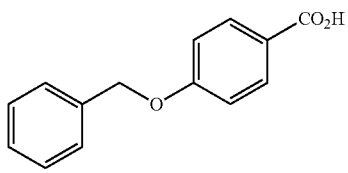
-continued
1066 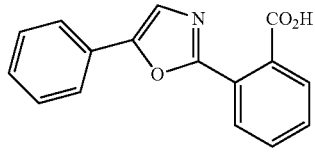
1068 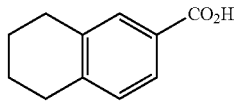
1069 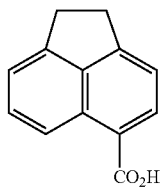
1070 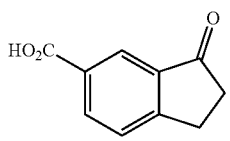
1071 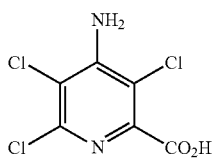
1072 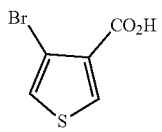
1073 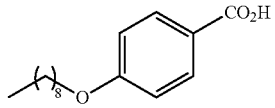
1074 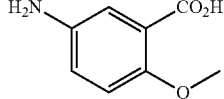
1075 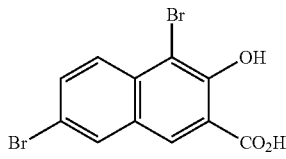
1076 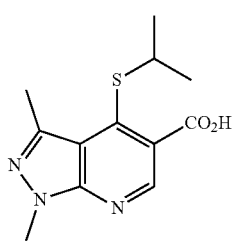

| | |
|---|---|
| 1077 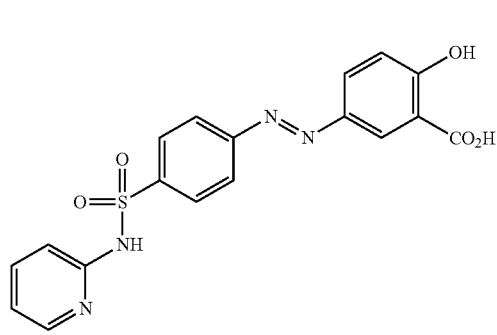 | 1086 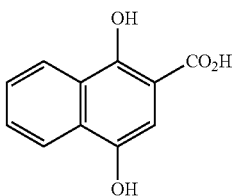 |
| 1078 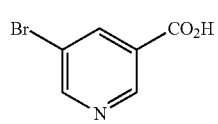 | 1087 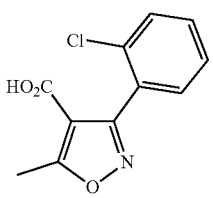 |
| 1079 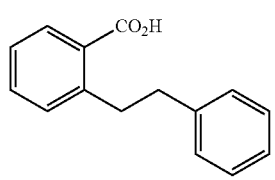 | 1088 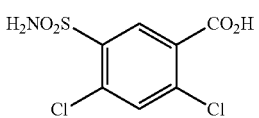 |
| 1080 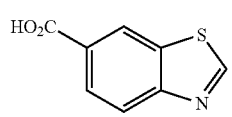 | 1089 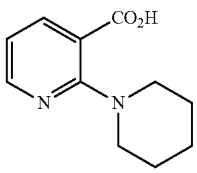 |
| 1081 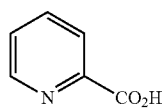 | 1090 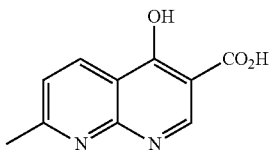 |
| 1082 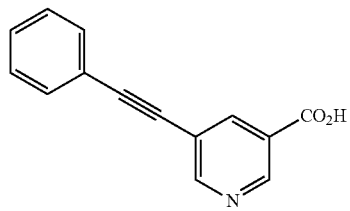 | 1091 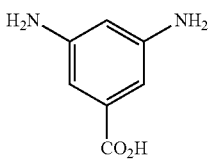 |
| 1083 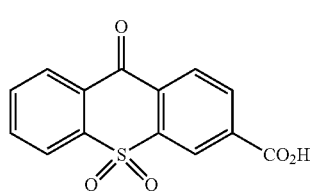 | 1092 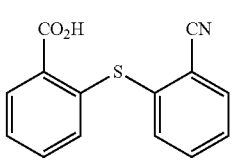 |
| 1084 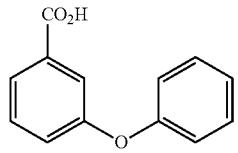 | 1093 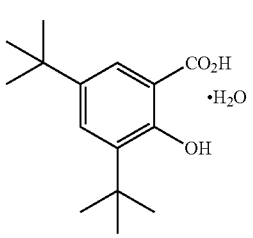 |
| 1085 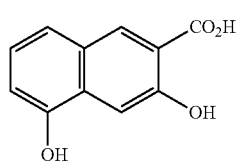 | 1094 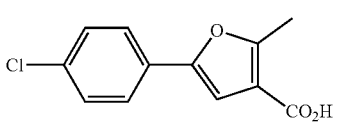 |

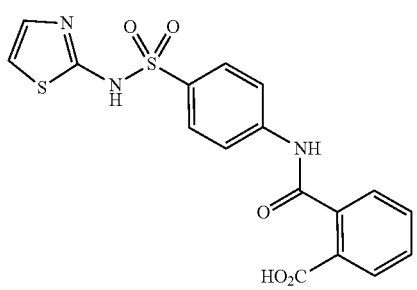
1095
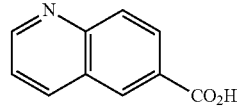
1105
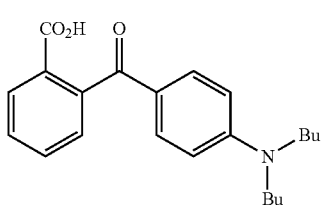
1096
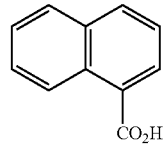
1106
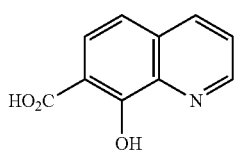
1097
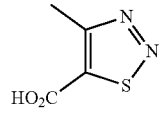
1107
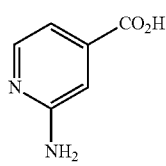
1098
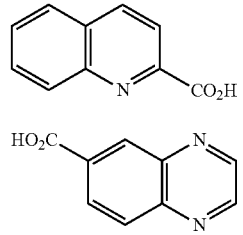
1108
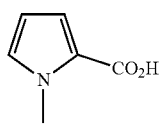
1099
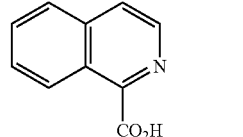
1109
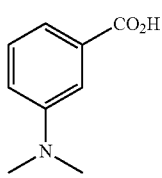
1100
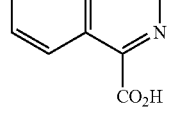
1110
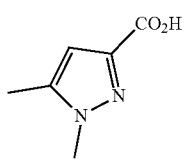
1101
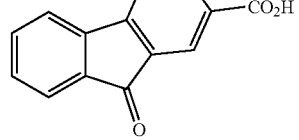
1111
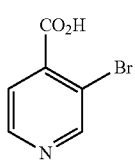
1102
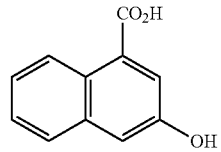
1112
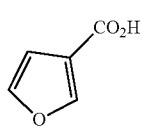
1103
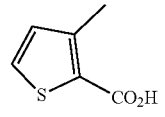
1113
1104
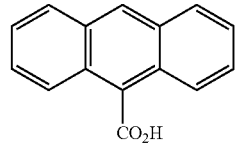
1114
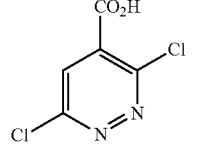
1115

1116 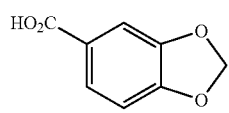
1117 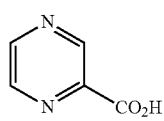
1118 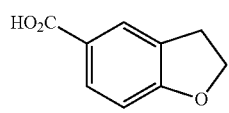
1119 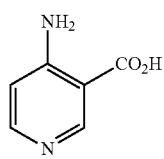
1120 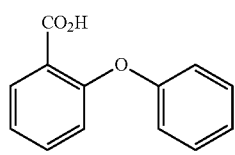
1121 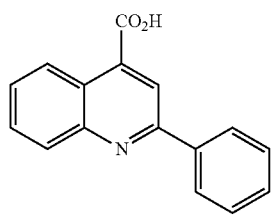
1122 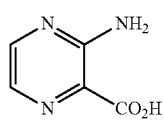
1123 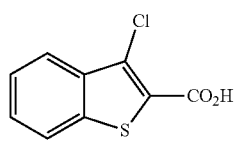
1124 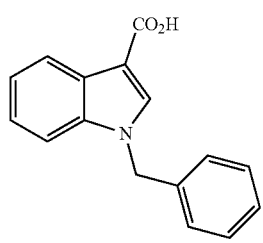
1125 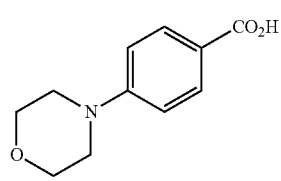
1126 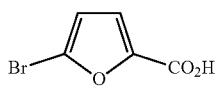
1127 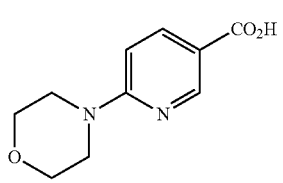
1128 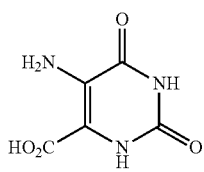
1129 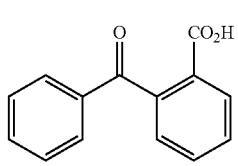
1130 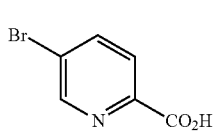
1131 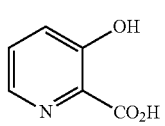
1132 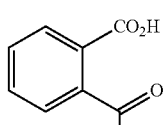
1133 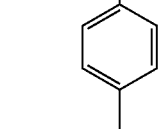
1134 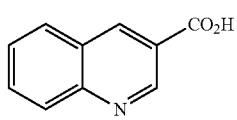
1135 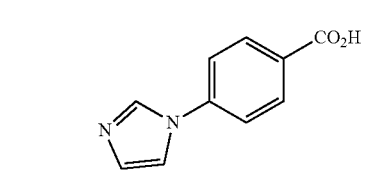

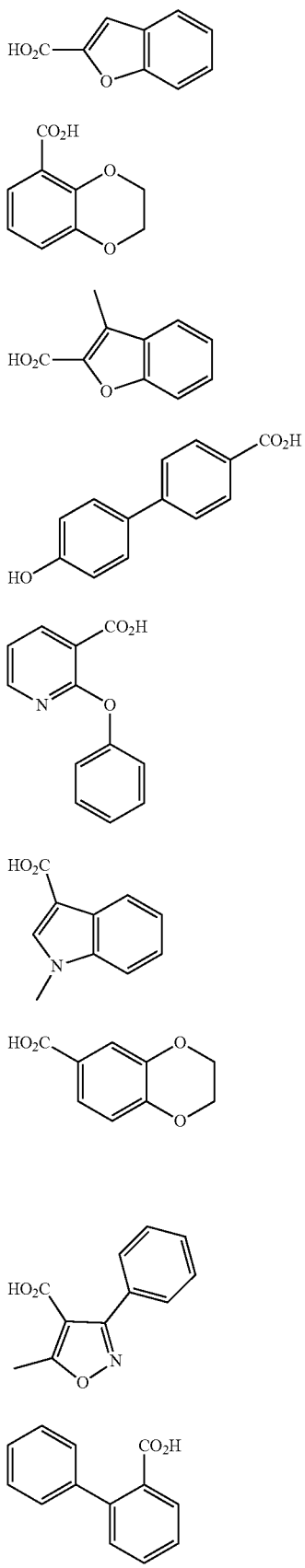
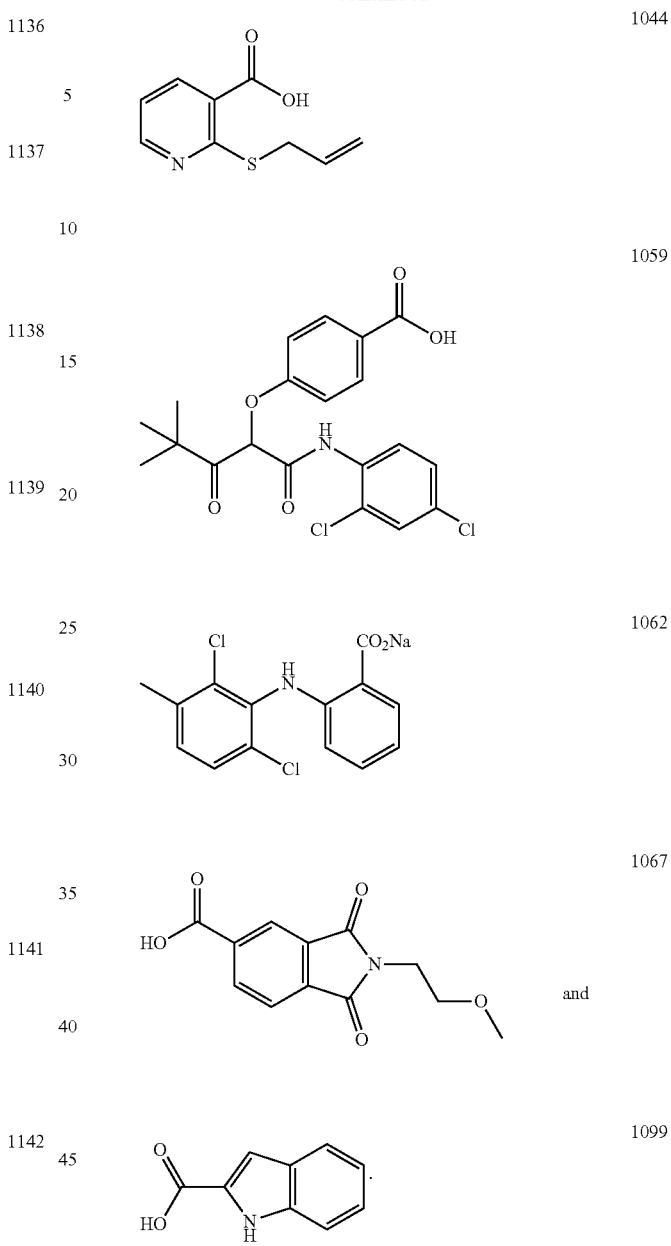
In yet more particular embodiments, the compound of formula (I) is selected from the group consisting of:
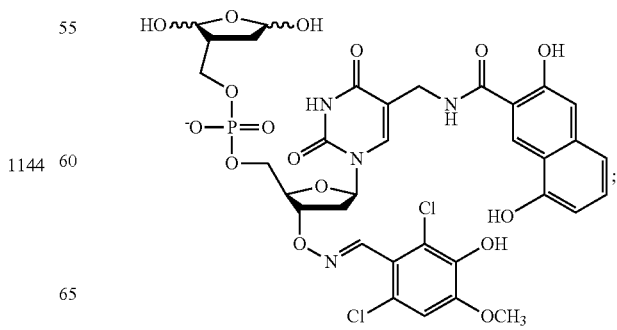

-continued

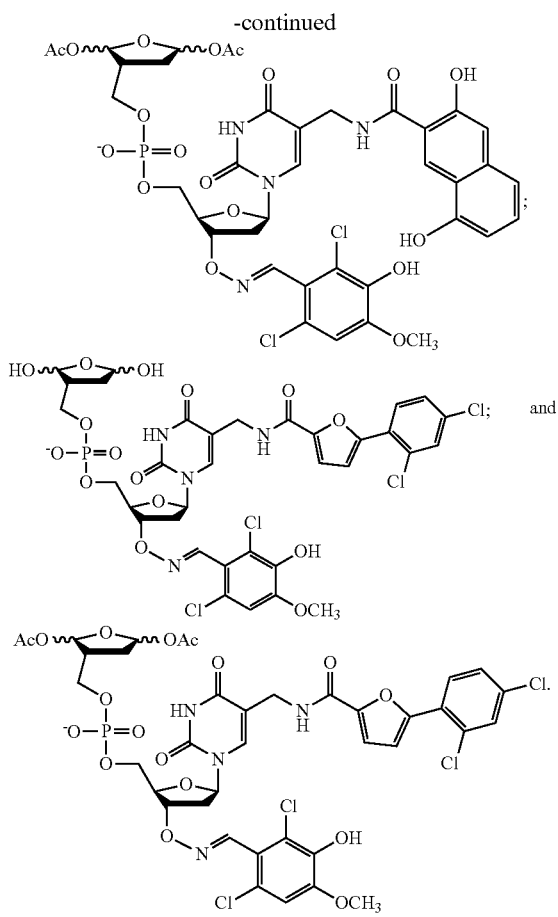

B. Method of Using Compounds of Formula (I)

In other embodiments, the presently disclosed subject matter provides a method for irreversibly inhibiting a DNA repair enzyme that possesses lyase activity in a subject, the method comprising administering to the subject a therapeutically effective amount of a compound of Formula (I).

As used herein, the term "inhibit" or "inhibits" has at least two meanings. It may mean to decrease, suppress, attenuate, diminish, arrest, or stabilize the development or progression of a disease, disorder, or condition, the activity of a biological pathway, or a biological activity such as cancer, e.g., by at least 10%, 20%, 30%, 40%, 50%, 60%, 70%, 80%, 90%, 95%, 98%, 99%, or even 100% compared to an untreated control subject, cell, biological pathway, or biological activity. It will be appreciated that, although not precluded, treating a disease, disorder or condition does not require that the disease, disorder, condition or symptoms associated therewith be completely eliminated. The term "inhibit" or "inhibits" may also mean to decrease, suppress, attenuate, diminish, or arrest the activity of an enzyme, which is a biological molecule that accelerates both the rate and specificity of a metabolic reaction. An "inhibitor" is a molecule that inhibits the activity of an enzyme. An "irreversible inhibitor" usually covalently modifies an enzyme and therefore the inhibition cannot be reversed. Irreversible inhibitors may act at, near, or remote from the active site of an enzyme.

In some embodiments, the subject has cancer. A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Proliferation of a cancer cell can include an increase in the number of cells as a result of cell growth and cell division. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas.

Without wishing to be bound to any one particular theory, it is believed that knocking down Pol β activity can be cytotoxic to a cancer cell. Therefore, in some embodiments, inhibiting the DNA repair enzyme treats, inhibits, delays, or prevents the spread of the cancer in the subject. In other embodiments, the method further comprises treating, inhibiting, delaying, or preventing the spread of the cancer by inhibiting at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, and changes in the levels of an extracellular protease.

In some embodiments, the presently disclosed subject matter provides a method for inhibiting a cancer cell, the method comprising contacting the cancer or noncancerous cell with a compound of Formula (I) in an amount effective to irreversibly inhibit a DNA repair enzyme that possesses lyase activity, thereby inhibiting the cancer cell.

The presently disclosed methods may further comprise administering to the subject a DNA damaging agent in combination with a compound of Formula (I). A "DNA damaging agent" is an agent that damages the DNA structure in some way, such as causing damage in the DNA bases or its sugar phosphate backbone or causing the formation of covalent bonds between the DNA and at least one protein. The DNA damage may affect DNA-histone and DNA-transcription factor interactions and may impact DNA packing, cell division, replication and/or transcription of the DNA.

As provided in more detail herein below, the presently disclosed compounds potentiate the cytotoxicity of a DNA damaging agent whose effects would require repair by Pol β. In particular embodiments, the DNA damaging agent is administered before, simultaneously, or after administration of the compound of Formula (I), or combinations thereof.

A DNA damaging agent may include, for example, an agent that alkylates DNA or oxidatively damages DNA. In particular embodiments, the DNA damaging agent is a methylating agent. In yet more particular embodiments, the methylating agent is methyl methanesulfonate (MMS). Other methylating agents include, but are not limited to, ifosfamide, busulfan, cyclophosphamide, bendamustine, carboplatin, chlorambucil, cisplatin, temozolomide, melphalan, carmustine, lomustine, dacarbazine, oxaliplatin, mechlorethamine, thiotepa, trabectedin, and streptozocin.

By "in combination with" is meant the administration of a compound of Formula (I), or other compounds disclosed herein, with one or more therapeutic agents, e.g., a DNA damaging agent, either simultaneously, sequentially, or a combination thereof. Therefore, a cell or a subject administered a combination of a compound of Formula (I), or other compounds disclosed herein, can receive a compound of Formula (I), or other compounds disclosed herein, and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I), or other compounds disclosed herein, and one or more therapeutic agents are administered simultaneously, they can be administered to the cell or administered to the subject as separate pharmaceutical compositions, each comprising either a compound of Formula (I), or other compounds disclosed herein, or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

In particular embodiments, a compound of Formula (I) and the DNA damaging agent work synergistically to inhibit a cancer cell. As used herein, the terms "synergy," "synergistic," "synergistically" and derivations thereof, such as in a "synergistic effect" or a "synergistic combination" or a "synergistic composition" refer to circumstances under which the biological activity of a combination of a compound of Formula (I) and another agent, e.g., an alkylating agent, such as methyl methanesulfonate (MMS), is greater than the sum of the biological activities of the compound of Formula (I) and the other agent when administered individually.

Synergy, expressed in terms of a "Synergy Index (SI)," generally can be determined by the method described by F. C. Kull, et al., Applied Microbiology 9, 538 (1961), from the ratio determined by:

$Q_a/Q_A+Q_b/Q_B$=Synergy Index (SI)

wherein:

$Q_A$ is the concentration of a component A, acting alone, which produced an end point in relation to component A;

$Q_a$ is the concentration of component A, in a mixture, e.g., a combination of components A and B, which produced an end point in relation to the combination;

$Q_B$ is the concentration of a component B, acting alone, which produced an end point in relation to component B; and $Q_b$ is the concentration of component B, in the mixture, which produced an end point in relation to the combination.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture.

Thus, a "synergistic combination" has an activity higher that what can be expected based on the observed activities of the individual components when used alone. Further, a "synergistically effective amount" of a component refers to the amount of the component necessary to elicit a synergistic effect.

In some embodiments, the presently disclosed method comprises a method for irreversibly inhibiting a DNA repair enzyme that possesses lyase activity in a cell, the method comprising contacting the cell comprising the DNA repair enzyme with a compound of Formula (I), wherein contacting the cell with the compound irreversibly inhibits the DNA repair enzyme.

By "contacting", it is meant any action that results in a therapeutically effective amount of at least one presently disclosed compound physically contacting at least one cell comprising a DNA repair enzyme. The method can be practiced in vitro or ex vivo by introducing, and preferably mixing, the compound and cell comprising a DNA repair enzyme in a controlled environment, such as a culture dish or tube. The method can be practiced in vivo, in which case contacting means exposing at least one cell comprising a DNA repair enzyme in a subject to a therapeutically effective amount of at least one compound of the presently disclosed subject matter, such as administering the compound to a subject via any suitable route. According to the presently disclosed subject matter, contacting may comprise introducing, exposing, and the like, the compound at a site distant to the cell comprising a DNA repair enzyme to be contacted, and allowing the bodily functions of the subject, or natural (e.g., diffusion) or man-induced (e.g., swirling) movements of fluids to result in contact of the compound and cell comprising a DNA repair enzyme(s). In some embodiments, the method may inhibit a DNA repair enzyme in vitro, in vivo, or ex vivo.

In other embodiments, the presently disclosed subject matter provides a pharmaceutical composition including one compound of formula (I), alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate. Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

The additional agents may be administered separately, as part of a multiple dosage regimen, from the inhibitor-containing composition. Alternatively, these agents may be part of a single dosage form, mixed together with the inhibitor in a single composition.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula I are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O) NR', —NR'R", —OR', —SR, and/or —SO₂R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH₂—); ethylene (—CH₂—CH₂—); propylene (—(CH₂)₃—); cyclohexylene (—C₆H₁₀—); —CH=CH—CH=CH—; —CH=CH—CH₂—; —CH₂CH₂CH₂CH₂—, —CH₂CH=CHCH₂—, —CH₂CsCCH₂—, —CH₂CH₂CH (CH₂CH₂CH₃)CH₂—, —(CH₂)_q—N(R)—(CH₂)_r—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH₂—O—); and ethylenedioxyl (—O—(CH₂)₂—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

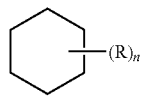

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

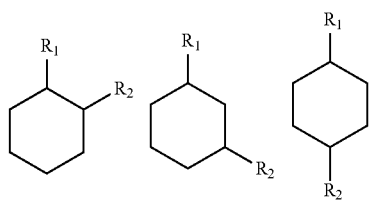

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —$CO_2$R', —C(O)NR'R", —OC(O)NR'R", —NR"C(O)R', —NR'—C(O)NR"R', —NR"C(O)OR', —NR—C(NR'R"R'")=NR"", —NR—C(NR'R")=NR"—S(O)R', —S(O)$_2$R', —S(O)$_2$NR'R", —$NRSO_2$R', —CN and —$NO_2$, —R', —$N_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —$CONH_2$.

"Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Proinhibitors of the compounds described herein are prodrugs that after undergoing chemical changes under physiological conditions, act as inhibitors (molecules that inhibit the activity of an enzyme).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

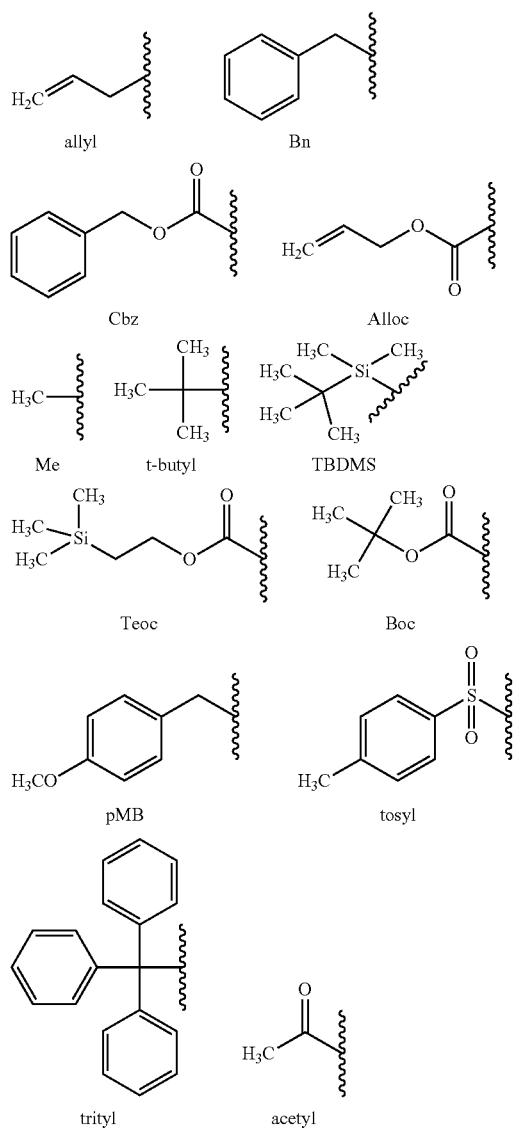

-continued

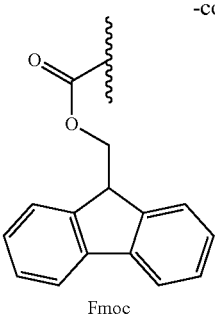

Fmoc

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Design and Synthesis of Irreversible Inhibitors of DNA Polymerase β

Compound 1 (FIG. 1; Scheme 4) which irreversibly inhibits Pol (Arian et al., 2014), and compound pro-1 (FIG. 1), a proinhibitor based on this molecule, and which works synergistically with methyl methanesulfonate (MMS) to kill prostate cancer cells (DU145), have been previously reported in U.S. Pat. No. 9,029,346, the disclosure of which is hereby incorporated by reference herein in its entirety. Pro-1 (20 µM) potentiates MMS about 3 to about 5 fold, depending upon the concentration of the alkylating agent.

Using 1 ($IC_{50}$ about 21 µM) as a starting point (Scheme 4), a library of 130 inhibitor candidates was prepared (see FIG. 2 for representative carboxylic acids used to create the presently disclosed library). This initial process yielded two candidates (13, 4' of Scheme 4) that irreversibly inhibit Pol β significantly more effectively than 1 of FIG. 1, Scheme 4. Compound 13 of Scheme 4 is amongst the most potent inhibitors of Pol β (Barakat et al., 2012b; Gavande et al., 2016).

Scheme 4. Presently disclosed reversible inhibitors of DNA polymerase β obtained using 1 as a starting point.

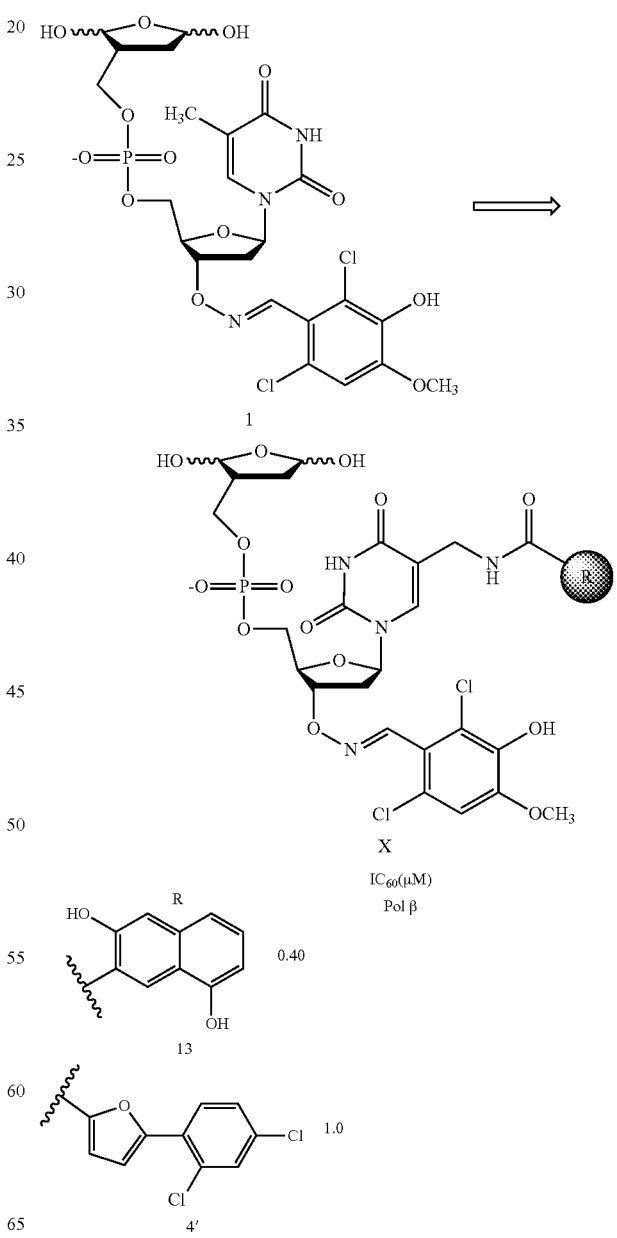

Also using 1 as a starting point, two synthetic routes using reductive amination are disclosed in Scheme 5 to prepare reversible inhibitors of DNA polymerase β of formulae Y, Z, and YZ.

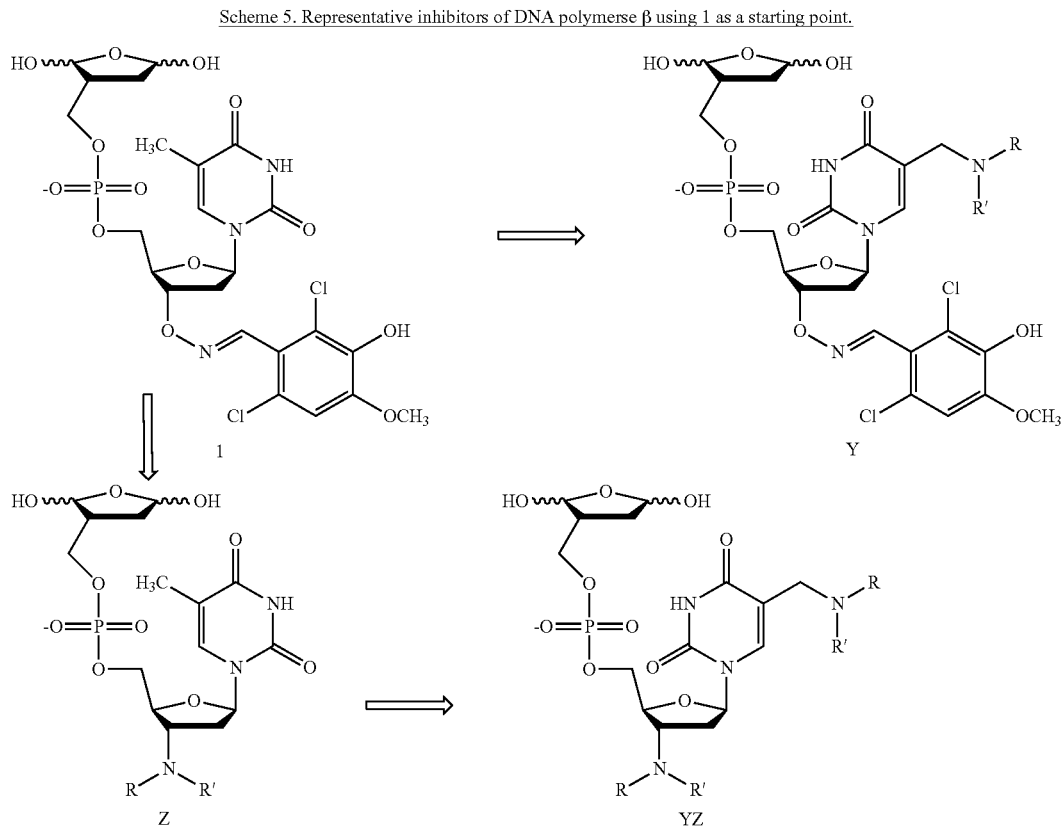

Scheme 5. Representative inhibitors of DNA polymerse β using 1 as a starting point.

Example 2

Synergistic Effects of an Irreversible DNA Polymerase Inhibitor and DNA Damaging Agents on HeLa Cells Abstract DNA repair is vital to maintaining genome integrity, but thwarts the effects of cytotoxic agents that target nucleic acids. Consequently, repair enzymes are potential targets for molecules that modulate cell function and anti-cancer therapeutics. DNA polymerase β (Pol β) is an attractive target because it plays a key role in base excision repair (BER), a primary pathway that repairs the effects of many DNA damaging agents. An irreversible inhibitor of Pol β was previously identified whose design was based upon a DNA lesion that inactivates Pol β and its back up BER enzyme, DNA polymerase λ (Pol λ). Using this molecule as a starting point, an irreversible inhibitor (13) of Pol β ($IC_{50}=0.4$ μM) and Pol λ ($IC_{50}=1.0$ μM) was characterized from a 130-member library of candidates that is approximately 50-fold more effective against Pol β. Pro-13 (5 μM) is only slightly cytotoxic to human cervical cancer cells (HeLa), but potentiates the cytotoxicity of methyl methanesulfonate (MMS). DNA isolated from HeLa cells treated with MMS contain an approximately 3-fold greater amount of abasic sites when pro-13 is present, consistent with inhibition of DNA repair. Proinhibitor pro-13 continues to induce cytotoxicity in DNA damaged cells following MMS removal. HeLa cell cytotoxicity is increased approximately 100-fold following an 8-h incubation with pro-13 after cells that were originally subjected to conditions under which 20% of the cells survive and reproduce. The potentiation of MMS cytotoxicity by pro-13 is greater than any previously reported BER enzyme repair inhibitor.

A variety of potentially cytotoxic endogenous and exogenous agents target DNA and modify its structure. The structural modifications include single strand breaks, modified nucleotides, and abasic sites. Dizdaroglu, 2015; Pitie and Pratviel, 2010. The base excision repair (BER) pathway (see Schemes 1 and 2) mitigates the cytotoxicity of these agents by removing the damage and restoring the DNA to its original structure. Schermerhorn and Delaney, 2014; Dianov and Hubscher, 2013.

While BER is critical for maintaining the genome integrity of healthy cells, it is a hindrance for anti-cancer modalities that target DNA. Liu et al., 2011. Consequently, the enzymes involved in BER are inhibition targets. Gavande et al., 2016; Goellner et al., 2012; Barakat et al., 2012a; Barakat et al., 2012b; Helleday et al., 2008; Wilson et al., 2010; Strittmatter et al., 2011. There are an increasing number of examples of BER enzyme inhibitors that potentiate the effects of cytotoxic DNA damaging agents. Gowda et al., 2017; Donley et al., 2015; Rai et al., 2012; Dorjsuren et al., 2012; Gao et al., 2008. An irreversible inhibitor of DNA polymerase β (Pol β) that works synergistically with methyl methanesulfonate (MMS) to kill HeLa cells is disclosed herein.

Pol β, a member of the X-family of polymerases, is a vital component of the BER pathway (Schemes 1 and 2), and cells lacking functional enzyme are not viable. Beard and Wilson, 2006; Sobol et al., 2000. Pol β is often over expressed in tumor cells and is mutated in ≥30% of human cancers. Donigan et al., 2012. The enzyme is responsible for two steps during BER (Schemes 1 and 2); in addition to filling in nucleotide gaps produced during the repair process, Pol β excises the remnants of AP sites (dRP) following 5'-incision by apurinic endonuclease 1 (Ape1). The lyase activity on dRP protects cells against cytotoxic agents. Lavrik et al., 2002; Horton et al., 2002; Trivedi et al., 2008; Trivedi et al., 2005; Sobol et al., 2003.

The AP sites are themselves produced via glycosidic bond hydrolysis either spontaneously or by one of several BER glycosylases present in cells. Sobol et al., 2000; Horton et al., 2003. The single nucleotide gap produced in DNA by 5'-dRP excision is filled following transfer of the DNA to the polymerase active site. DNA polymerase λ (Pol λ) also is an X-family polymerase. It too possesses 5'-dRP lyase activity, albeit kinetically less efficient than Pol β, and is believed to act as a back up to Pol β. Garcia-Diaz et al., 2001; Braithwaite et al., 2010; Braithwaite et al., 2005; Stevens et al., 2013.

Pol β is an interesting therapeutic target because its expression is up-regulated and/or it is mutated in many tumor cells. For instance, Pol β is mutated in as many as 40% of colon cancers. Donigan et al., 2012. Some mutated forms of Pol β retain activity, providing a possible tumor specific target. The potential benefit of Pol β inhibition has spurred the development of inhibitors, but there is room for improvement. The most effective inhibitors exhibit $IC_{50}$'s in the low micromolar range, and in some instances the selectivity for Pol β over other enzymes is not known and/or whether the molecule targets the polymerase or lyase activity. Goellner et al., 2012; Barakat et al., 2012a; Barakat et al., 2012b.

The approach disclosed herein is consistent with the discovery that lesions produced by anti-tumor agents that oxidatively damage DNA irreversibly inhibit Pol β and Pol λ (Scheme 6). Stevens et al., 2013; Jacobs et al., 2011; Guan and Greenberg, 2010; Guan et al., 2010.

Scheme 6. Pol B inactivation by oxidized abasic sites.

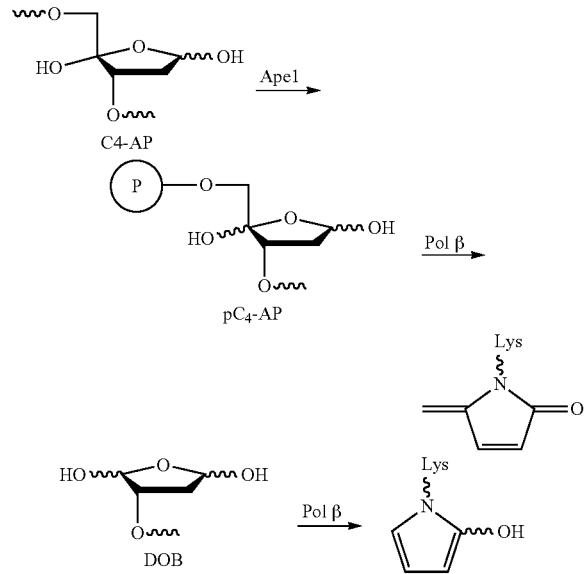

C4-AP and/or DOB are produced by C4'- and C5'-hydrogen atom abstraction, respectively. The polymerases recognize DOB directly and C4-AP (pC4-AP) following DNA incision by Ape1. The lesions contain a common 1,4-dicarbonyl motif, which results in the formation of a covalent adduct with one or more lysine residues within the lyase active sites of Pol β and Pol λ. The 1,4-dioxobutane moiety was incorporated into a library of small molecules that were screened for inhibition of Pol β, resulting in identification of compound 1 that irreversibly inhibits Pol β with an $IC_{50}=21$ μM. Arian et al., 2014.

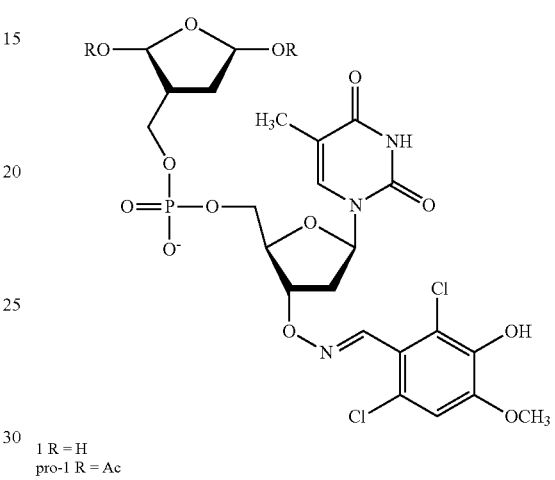

1 R = H
pro-1 R = Ac

In addition, the proinhibitor (pro-1, i.e., the acetate (—OAc)) potentiates the cytotoxicity of the DNA alkylating agent methyl methanesulfonate (MMS). When employed together, pro-1 (20 μM) and MMS (≥0.3 mM) are at least 3-fold more potent against DU145 prostate cancer cells than expected based upon the cytotoxicity of the individual molecules. Irreversible inhibition of Pol β by targeting its lyase active site is a path less traveled in the search for inhibitors, and 1 served as the starting point for the presently disclosed subject matter.

Results and Discussion

Design and Preparation of Second Generation Pol β Inhibitors.

Inhibitor 1 and the corresponding proinhibitor (pro-1) were selected from a molecular library in which structural diversity was introduced at the 3'-terminus of the nucleotide. In the second-generation library of inhibitors described herein the methyl group of thymidine was functionalized with the goal of probing a different region of the protein-binding site. The library was prepared by synthesizing amides from amine 2 (Scheme 7). HBTU activation in the presence of HOBt was used to form the amide bond in pro-3. The acetate protecting groups were then removed using $BF_3 \cdot Et_2O$ in wet (2% $H_2O$) acetonitrile. Quenching the deprotection reaction with phosphate buffered saline was important for preventing inhibitor decomposition. An advantage of using the bis-acetate protecting group over the previously employed pentenyl acetal is it was anticipated that the immediate precursor (pro-3) would be used as the proinhibitor in cells. Arian et al., 2014.

Scheme 7. General library synthesis.

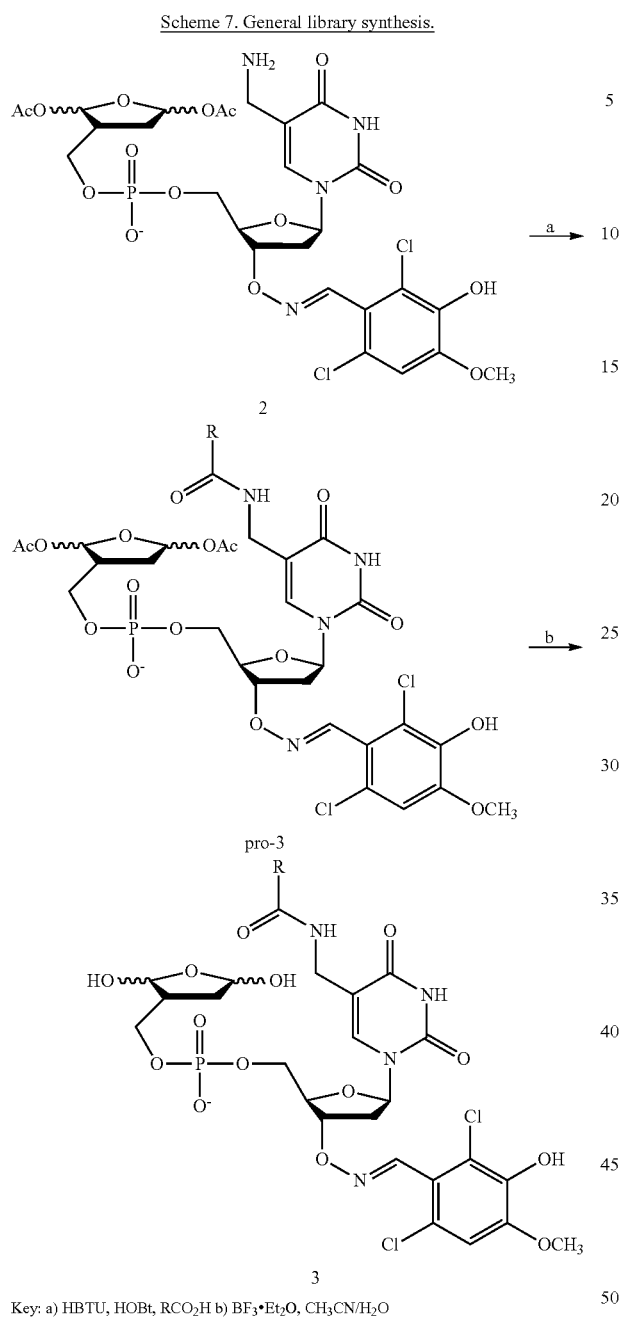

Key: a) HBTU, HOBt, RCO₂H  b) BF₃·Et₂O, CH₃CN/H₂O tion with the azide. The successful coupling of phosphoramidite 11 with azide containing 7, followed by in situ oxidation to the phosphate triester was consistent with previous reports in which these functional groups that could react with one another are successfully combined in oligonucleotide synthesis. Pourceau et al., 2009.

Scheme 8. Synthesis of inhibitor library precursor amine (2).

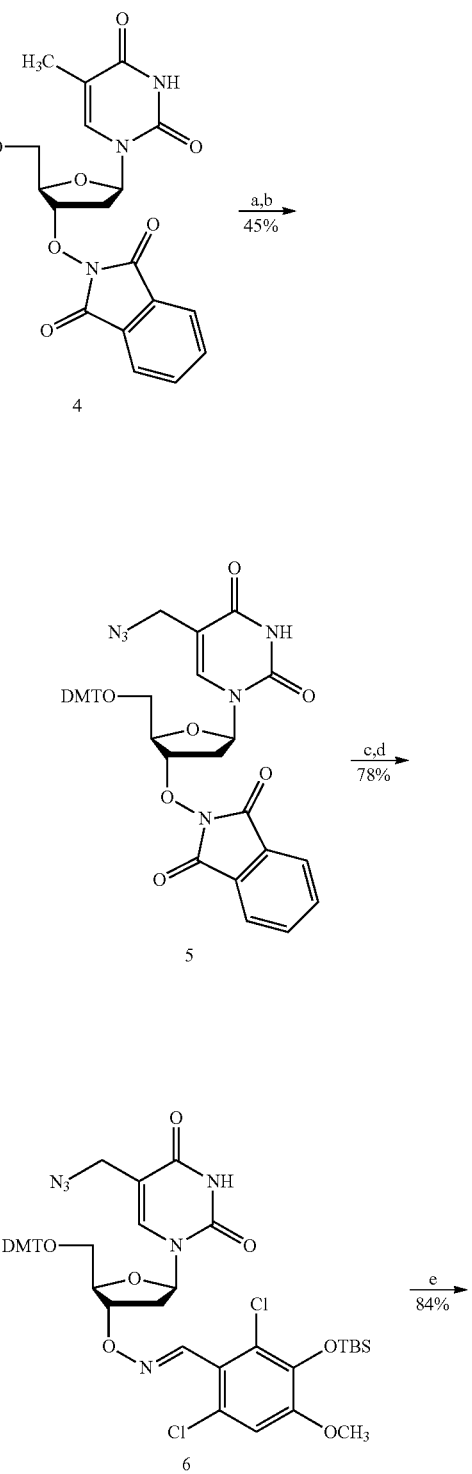

The requisite amine (2) was initially prepared from previously reported 4 (Scheme 8). Arian et al., 2014; Chen et al., 2010. The azide group (5) was introduced in modest yield via the bromide, which was used crude. Hong and Greenberg, 2004; Neef, and Luedtke, 2014. The oxime containing a protected phenol was then introduced (6), followed by detritylation of the primary alcohol to yield 7. The requisite aldehyde (9) used in the preparation of 7 was prepared from 8. It was necessary to protect the phenol hydroxyl of 8 to prevent it from competing with the primary alcohol in 7 during phosphoramidite coupling with 11. The latter was prepared from previously reported 10. Arian et al., 2014.

The phosphoramidite was introduced via the protected dioxobutane component (10) to prevent intramolecular reac-

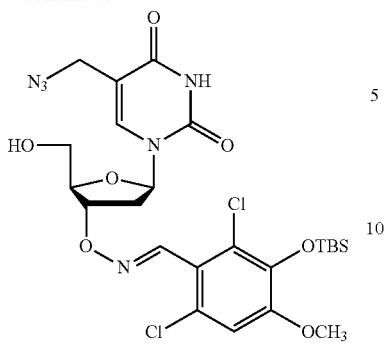
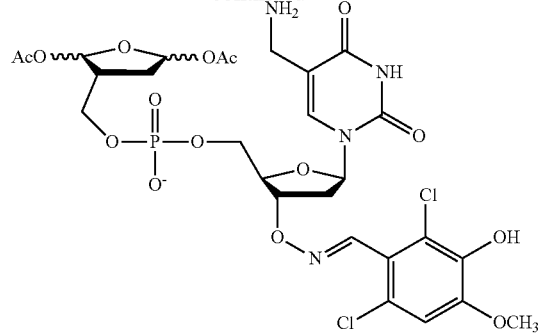

a) NBS, AIBN b) NaN$_3$ c) Hydrazine d) 9 e) AcOH/H$_2$O f) t-BuMe$_2$SiCl g) Phophitylation h) i. S-Ethyl tetrazole ii. t-BuOOH i) Et$_3$N j) H$_2$, Pd/C During the library synthesis the β-cyanoethyl and TBS groups in 12 were cleaved using Et$_3$N base. Azide 12 was the last intermediate that was purified prior to library synthesis, as the amine (2) used for preparing the amides obtained via hydrogenation was used crude. Following identification of a candidate inhibitor (13, below), the final sequence of steps for transforming into the bisacetate protected inhibitor (pro-inhibitor, pro-13) were altered. Reducing the azide first, and cleaving the phosphate and phenol protecting groups after amide formation provided higher yield of more readily purified product that was used in subsequent experiments as a mixture of diastereomers.

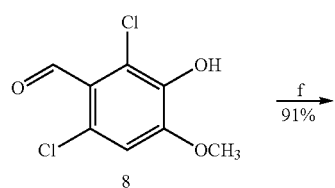
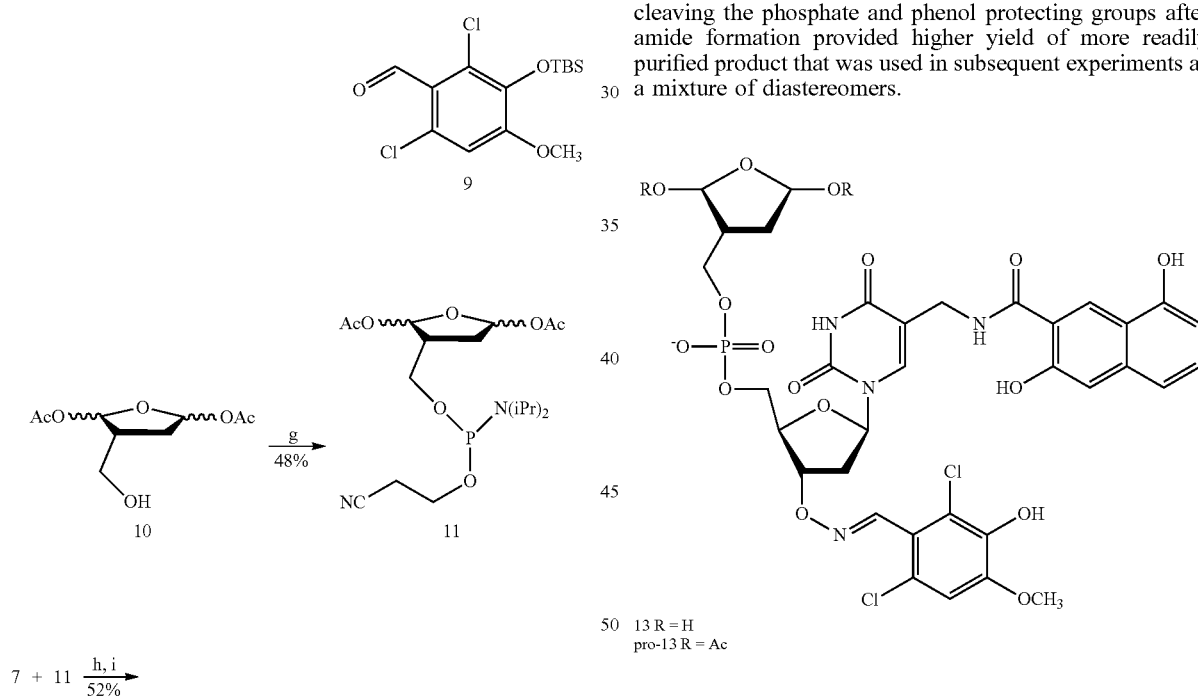

Inhibition of strand displacement synthesis results in decreased fluorescence growth compared to the absence of inhibitor. The screening conditions were the same with the exception of the inhibitor concentration. The oxime library that yielded 1 was screened using 50 μM of candidates, whereas 3 were present at 10 μM. Of the 130 candidates screened, five completely shut down fluorescence growth at 10 μM when preincubated with Pol β (5 nM). The five most promising candidates bore little resemblance to one another other than that they were aromatic carboxylic acids (Scheme 10). Their inhibition of Pol β was examined at as low as 1 μM using the fluorescence assay, which identified 13 as the most promising candidate. Candidate 13 was resynthesized, spectroscopically characterized, and inhibition by it was directly quantified.

Scheme 10. Inhibitor candidates identified from fluorescence screen.

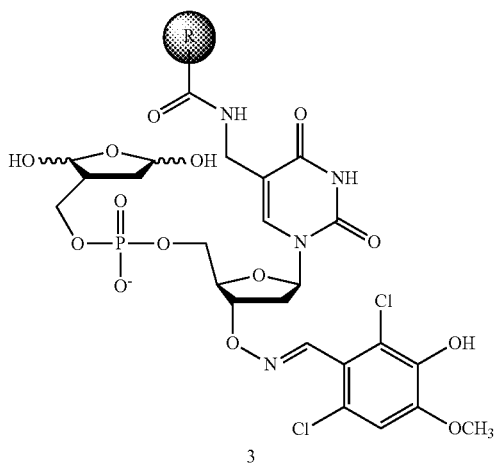

(13)

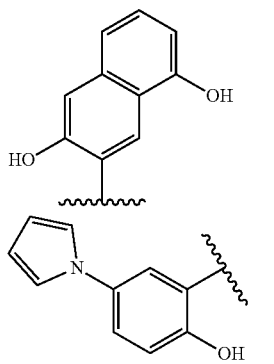

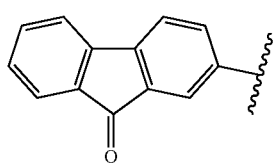

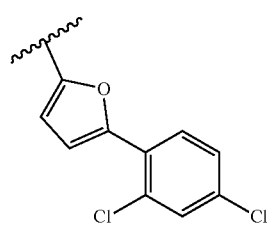

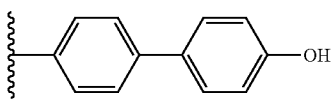

Irreversible inhibition of Pol β lyase activity was determined using 3'-32P-dRP substrate 15. SEQ ID NO: 1

SEQ ID NO: 1
5'-d(TAA TGG CTAACG CAA XAC GTAATG CAG TCT)-$^{32}$P-3'
3'-d(ATT ACC GAT TGC GTT ATG CAT TAC TGC AGA)
SEQ ID NO: 2

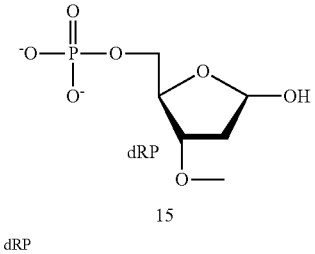

15

X = dRP

Figure 3A:
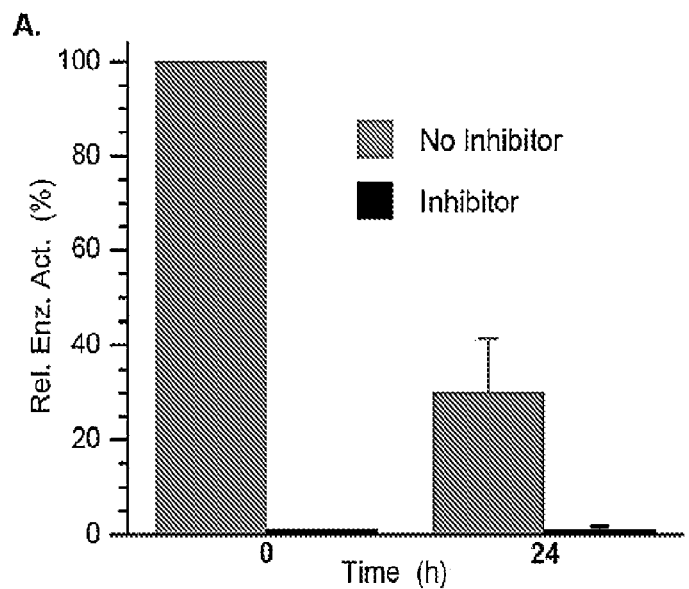
Figure 3B:
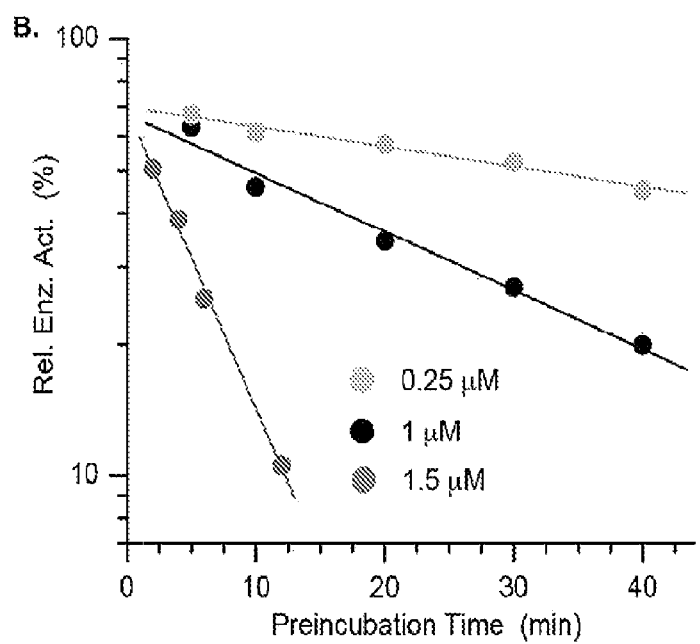

Preincubation of Pol β with 13 (3 μM) for 30 min resulted in 99% loss of lyase activity, which was not recovered following dialysis for 1 day (FIG. 3A). Additional evidence for Pol β inactivation was obtained by examining the remaining lyase activity as a function of preincubation time and concentration of 13 (FIG. 3B). A modest decrease in Pol β activity was observed when the enzyme was preincubated with 0.25 μM 13, but much greater activity loss was observed upon less than 30 min preincubation times in the presence of 1.0 or 1.5 μM inhibitor (FIG. 3B). The data in FIG. 3B indicate that 13 inactivates Pol β significantly more effectively than 1. Arian et al., 2014.

Figure 3C:
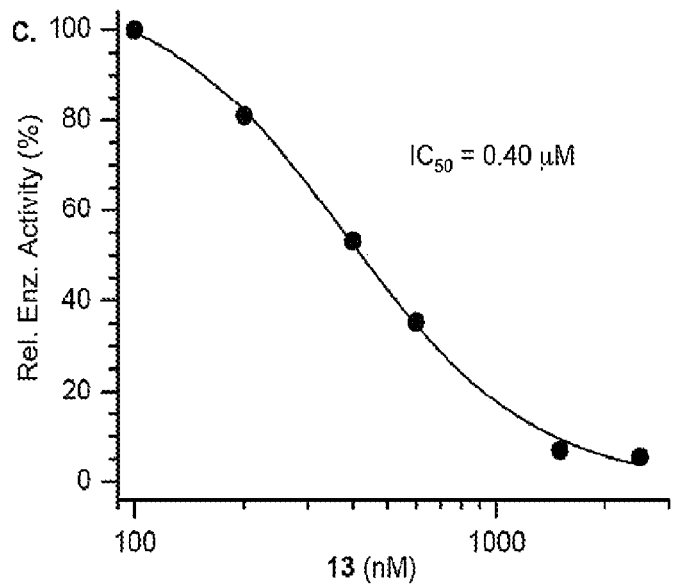
Figure 3D:
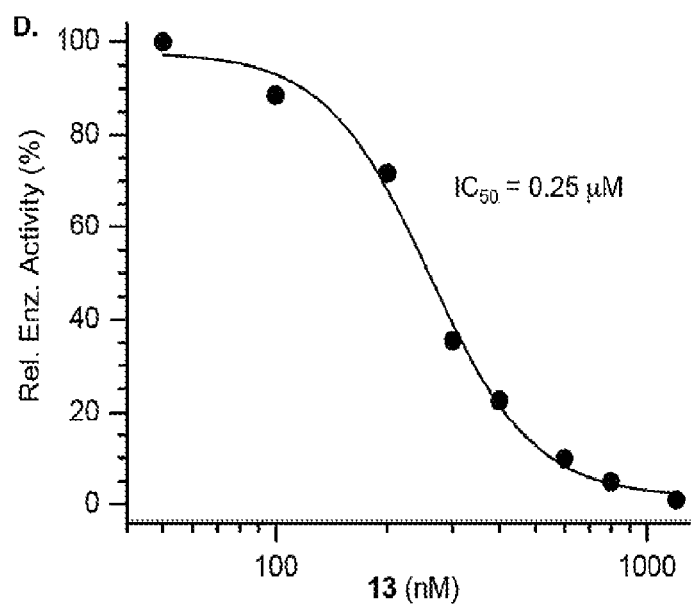

Comparing the $IC_{50}$'s of the respective compounds reinforced this comparison. Upon preincubating 1 (21 μM) or 13 for 30 min with Pol β, the $IC_{50}$ (0.4 μM) of the latter was more than 50-times lower than the previously reported inhibitor (FIG. 3C). In addition, to marking a significant improvement over 1, the activity of 13 against Pol β compares favorably to other previously reported inhibitors, some of which also target the lyase domain. Barakat et al., 2012b. The $IC_{50}$ for Pol λ inactivation by 13 was even lower (0.25 μM, FIG. 3D). Although this result was surprising, it would be helpful in cellular toxicity studies if 13 inactivated Pol β and its back-up repair enzyme.

Potentiation of DNA Damaging Agent Cytotoxicity in HeLa Cells.

Previous studies showed that proinhibitor pro-1 was converted to 1 (presumably by cellular esterases), and was more effective at inhibiting lyase activity on 15 in prostate cancer cell (DU145) lysates. Furthermore, pro-1 (20 μM) yielded more than a 3-fold enhancement in MMS (≥0.2 mM) cytotoxicity. Arian et al., 2014. Herein, the effect of pro-13 on bleomycin (BLM) and MMS cytotoxicity in HeLa cells was examined using a clonogenic assay. BLM oxidatively damages DNA by abstracting hydrogen atoms from the C4'-position of pyrimidines. McGall et al., 1992; Rabow et al., 1990; Sugiyama et al., 1990; Kozarich et al., 1989.

Oxidation results in direct strand breaks and the alkali labile C4-AP oxidized abasic site, a known irreversible inhibitor of Pol β and Pol λ. Stevens et al., 2013; Jacobs et al., 2011. BLM also produces double-strand breaks. Absalon et al., 1995a; Absalon et al., 1995b. In contrast MMS is an alkylating agent, which largely reacts with the N7-position of dG. Fu et al., 2012; Wyatt and Pittman, 2006; Gates et al., 2004. Although BLM and MMS react very differently with DNA, both activate base excision repair, and therefore Pol β is involved.

Figure 4A:
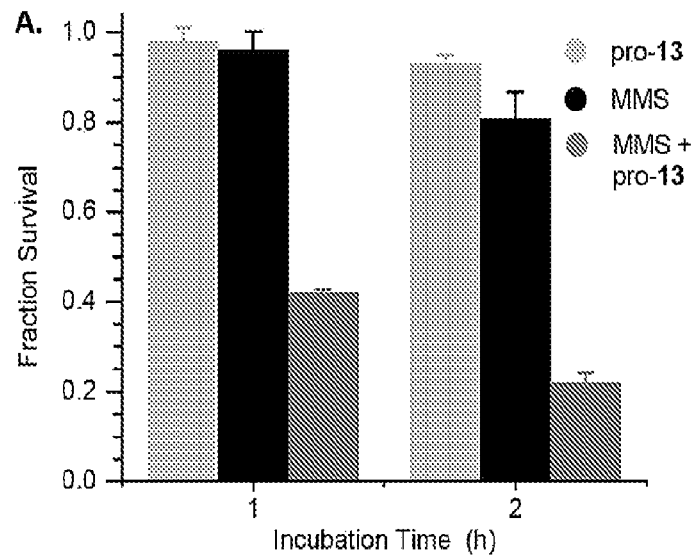
Figure 4B:
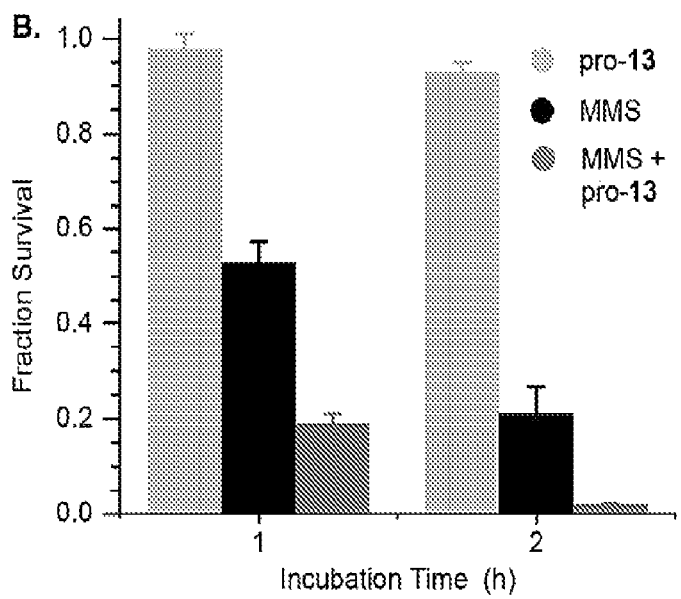
Figure 4C:
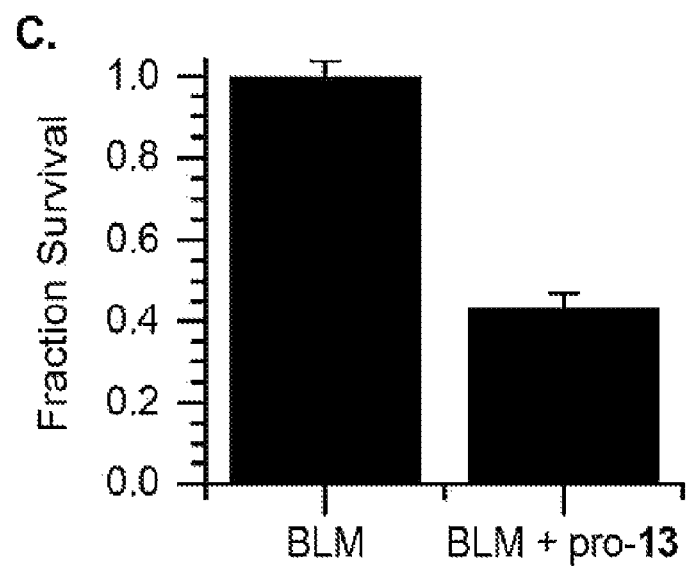

The proinhibitor (pro-13) exhibits modest cytotoxic effects on HeLa cells. Exposing cells to 5 μM pro-13 for 1 h results in 2% cell death and 93% of the cells survive when exposed for 2 h. No observable cell death is detected when HeLa cells are exposed to BLM (2 μM) for 2 h, followed by a 2 h recovery time (FIG. 4C), although a Comet assay confirms DNA damage. In contrast, only 43% of the cells survive, a more than 2-fold decrease in fraction cell survival, when pro-13 (5 μM) and BLM (2 μM) are co-incubated. The potentiation of MMS cytotoxicity by pro-13 was greater in HeLa cells (FIGS. 4A, 4B) when compared to that of BLM. HeLa cells were treated with 0.1 mM (FIG. 4A) or 0.2 mM (FIG. 4B) MMS for 1 or 2 h with and without pro-13 (5 μM). The potentiation of MMS cytotoxicity was greater under all conditions than what was observed using BLM. The cytotoxic effects of MMS and BLM with and without pro-13 were most similar under the mildest conditions (0.1 mM MMS, 1 h, FIG. 4A) examined. Increasing the MMS exposure time to 2 h increased the overall cytotoxicity, but potentiation by pro-13 was greater, as well (FIGS. 4A, 4B). Individual treatment with pro-13 (5 μM) or MMS (0.1 mM) for 2 h resulted in 7% and 15% cell death, respectively (FIG. 4A). The synergistic effects of pro-13 and MMS lead to average fraction survival of 0.23, which is approximately 3.4-fold lower than that expected based upon the cytotoxic effects of the agents used separately. An even greater potentiation of MMS cytotoxicity by pro-13 was observed at longer reaction time when using 0.2 mM of the alkylating agent (FIG. 4B). Fewer than 2% of the HeLa cells survived when pro-13 was included compared to 25% when MMS was used without the proinhibitor, accounting for an almost 13-fold enhancement in cytotoxicity compared to the individual agents. To directly compare the efficacy of pro-13 (5 μM) with the effects of pro-1 (5 μM) on MMS cytotoxicity in HeLa cells, comparable experiments were carried out with the latter. Pro-1 was significantly more cytotoxic, killing 40% of the cells after 2 h incubation. In addition, no synergism was observed with MMS under any of the above concentration and time conditions, indicating that pro-13 is a superior adjuvant to MMS in HeLa cells.

Co-Administration of Pro-13 and MMS Increases AP/dRP Levels in HeLa Cells

Evidence that pro-13 leads to BER inhibition in HeLa cells was obtained by determining its effect on the level of aldehyde reactive probe (ARP) sites (Table 1). ARP is routinely used to quantify AP sites in DNA, and has been employed to validate Ape1 inhibition, but dRP detection via this method was not known. Rai et al., 2012; Dorjsuren et al., 2012; Ide et al., 1993; Asaeda et al., 1998. Inhibitor 13 does not affect Ape1 activity on a duplex containing AP. Hence, any increase in ARP reactive sites would presumably result from reaction with dRP. Inhibition of Pol β (and/or Pol λ) should lead to a build-up of dRP sites instead of AP, which would be indistinguishable from AP using ARP (Scheme 11). Although it was assumed that the more labile dRP reacts with ARP, it was demonstrated that this is indeed the case using a ternary complex containing the former (15). The level of AP/dRP sites in the genomic DNA isolated from HeLa cells treated with MMS, pro-13 or a combination, was subsequently measured. Following treatment with the DNA damaging agent (1 h), the medium was replaced with fresh medium with or without pro-13 (5 μM), and the cells were incubated an additional 23 h. The level of ARP reactive sites increased approximately 3-fold when cells were treated with a combination of MMS and pro-13 compared to just the alkylating agent (Table 1), consistent with the inhibition of BER in cells treated with the proinhibitor.

Scheme 11. AP and dRP detection by ARP.

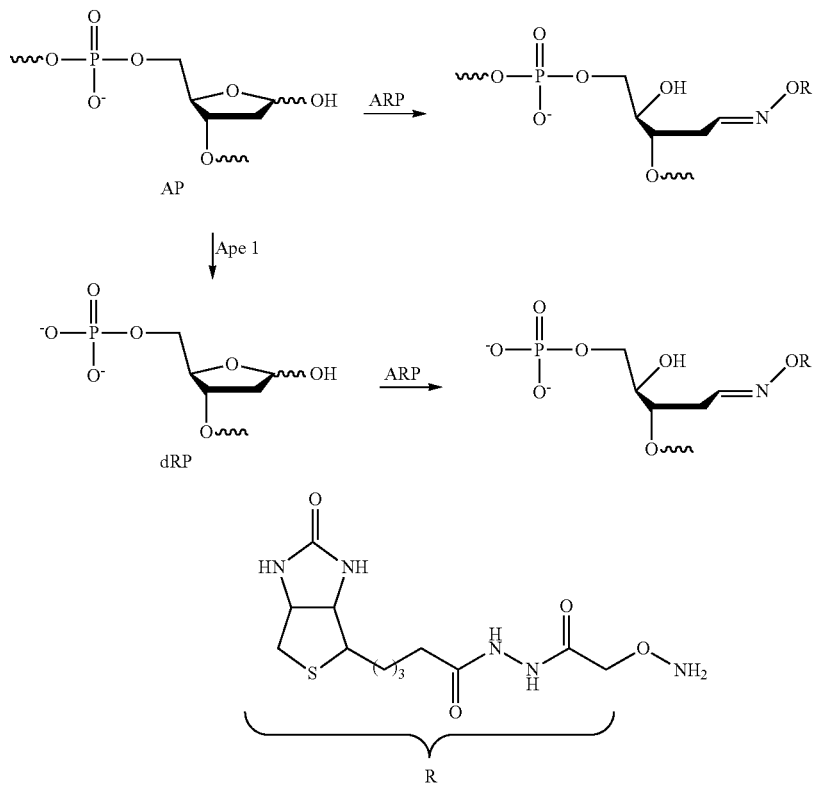

TABLE 1

Increased AP/dRP content in DNA from HeLa cells treated with MMS and pro-13.

| MMS (mM) | pro-13 (μm) | AP/dRP sites/$10^5$ bp[a] |
|---|---|---|
| — | — | 3.8 ± 0.9 |
| — | 5 | 4.6 ± 1.0 |
| 0.3 | — | 9.2 ± 1.2 |
| 0.3 | 5 | 28.0 ± 1.4 |
| 0.4 | — | 11.0 ± 1.5 |
| 0.4 | 5 | 33.0 ± 1.5 |

[a]Average ± std. dev. of 3 independent experiments

DNA Repair Inhibition After Removing MMS Increases Cell Death.

Figure 4D:
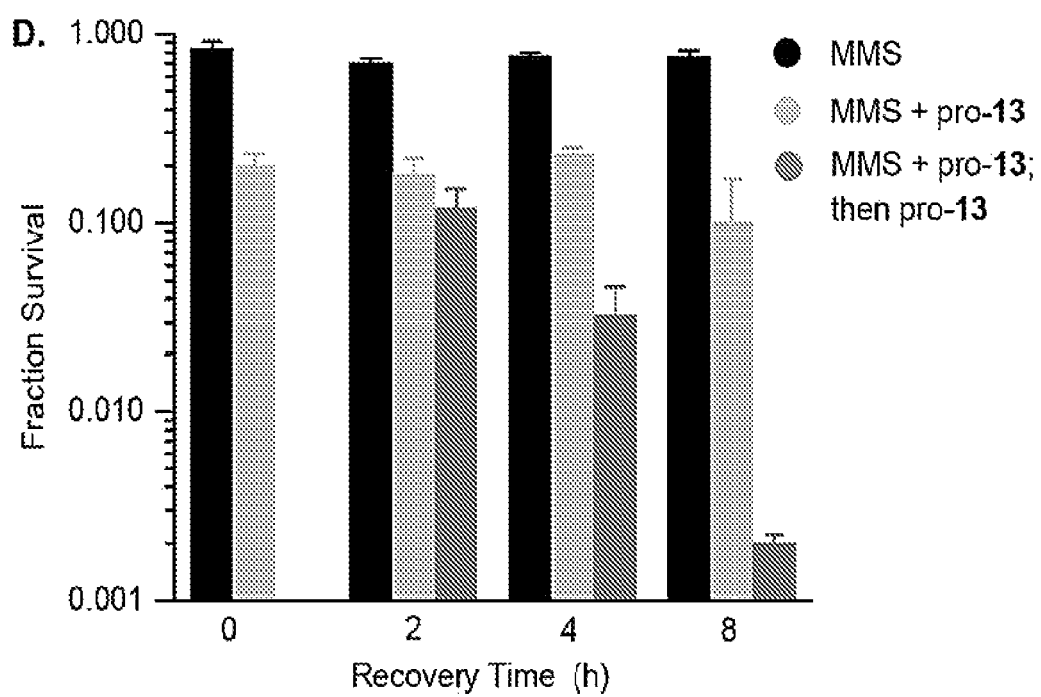

The AP/dRP detection in genomic DNA isolated from HeLa cells (Table 1) suggests that the inhibitor significantly prolongs the lifetime of these lesions in cells. Without wishing to be bound to any one particular theory, it was thought that unrepaired lesions would induce cell death in the absence of DNA damaging agent. Consequently, HeLa cells were treated with MMS (0.1 mM) for 2 h, with or without pro-13 (5 μM) (FIG. 4D). These conditions produce modest levels of cell death (FIG. 4A); even with inhibitor the survival fraction is 0.21±0.04. After 2 h, the media from cells treated with MMS was replaced with media lacking the alkylating agent. Samples containing cells treated with MMS and pro-13 were treated similarly. However, the replacement media for a third set of cells that were treated with the above mixture of MMS and proinhibitor contained pro-13 (5 μM). The 3 sets of cells were then incubated for up to 8 h before plating for the clonogenic assay (FIG. 4D). No significant additional cell death occurs if the replacement media lacks pro-13, regardless of whether the cells were initially treated with MMS or proinhibitor and alkylating agent. However, the fraction of surviving cells continually decreases as the incubation period increases when the replacement media contains pro-13 (5 μM). After 4 h additional incubation with the proinhibitor, the fraction cell survival is ⅕th as much as those incubated in the absence of pro-13. Finally, following 8 h of additional incubation, only 0.20±0.02% of the cells survive when incubated in the presence of pro-13. This is a 100-fold smaller fraction of cells that survive following initial co-treatment with MMS and pro-13.

SUMMARY

Disrupting the base excision repair pathway sensitizes cells to DNA damaging agents. DNA repair enzyme inhibitors that can be used as adjuvants to nucleic acid damaging molecules are potentially useful as therapeutic agents. Trivedi et al., 2008; Trivedi et al., 2005; Sobol et al., 2003. DNA polymerase β is an attractive target because this enzyme is required for cell viability. A structurally diverse group of Pol β inhibitors have been identified. Goellner et al., 2012; Barakat et al., 2012b. Some of these molecules target the polymerase active site, while others such as the molecule examined here inhibit the enzyme's lyase activity. Comparison of inhibitors from independent studies is challenging due to different cell types, DNA damaging agents employed, and inhibition mechanism. Barakat et al., 2012b; Gowda et al., 2017; Gao et al., 2008. Nucleic acid lesions produced by highly cytotoxic DNA damaging agents that inactivate Pol β (and Pol λ) have provided the inspiration for the design of the small libraries of irreversible inhibitors disclosed herein. Inhibitors that target the lyase activity of Pol β are less common than those that affect the polymerase site. Barakat et al., 2012b. Irreversible inhibitors are even more rare. Inhibiting Pol β lyase activity results in concomitant build-up of cytotoxic dRP, increasing the attractiveness of such inhibitors. Sobol et al., 2000.

Inhibitor 13, which is 50-fold more effective at inactivating Pol β than a first generation molecule (1) based on this approach, was identified in the presently disclosed subject matter. Arian et al., 2014. Using previous studies comparing the effects of 1 and pro-1 in cells as a guide, experiments in HeLa cells were carried out using a proinhibitor of 13 (pro-13). Pro-13 (5 μM) is itself only weakly cytotoxic, but exerts synergistic effects on MMS cytotoxicity. Pro-13 potentiated MMS cytotoxicity in HeLa cells as much as approximately 13-fold. The previously reported proinhibitor (pro-1) showed no synergistic effect with MMS in HeLa cells under identical conditions. Furthermore, administration of pro-13 in fresh media to cells previously co-treated with MMS and the proinhibitor under conditions that result in modest toxicity increases cell death approximately 100-fold, yielding 0.2% HeLa cell survival. The extent of this potentiation of MMS cytotoxicity by pro-13 is greater than any previously reported BER enzyme repair inhibitor that we are aware of. Furthermore, the concentration at which pro-13 is effective in HeLa cells is comparable to or superior to even the most recent reported Pol β inhibitors. Goellner et al., 2012; Barakat et al., 2012b; Gowda et al., 2017. These observations indicate that Pol β inactivation is a promising approach for potentiating DNA damaging agents.

Methods

General Methods.

All reactions were run in Pol β reaction buffer: 50 mM HEPES (pH=7.5), 5 mM $MgCl_2$, 0.2 mM EDTA, 50 mM KCl and 0.01% Tween 20 and analyzed by 20% denaturing PAGE. Quantitative analysis was carried out using a Storm 840 phosphorimager and ImageQuant TL software.

Library Synthesis (Pro-3).

A solution of 12 in water (0.1 mL, 45 mM, 4.5 μmol) was diluted with 1:1 methanol-ethanol (2 mL). Pd/C (2.2 mg) was added and the mixture was stirred under a blanket of $H_2$ for 3 h. The suspension was filtered through a pad of celite (1×2 cm) and washed with methanol. The combined filtrate and washings were concentrated under reduced pressure and the amine (2) was dissolved in 0.1 mL $H_2O$; HRMS (ESI) m/z calculated for $C_{27}H_{32}N_4O_{15}PCl_2$ (M−H)− 753.0979, observed 753.0943). The crude amine was used to prepare the library. Carboxylic acids (10 μL, 0.1 M in DMF, 1.0 μmol) were activated in 96 well plates by adding HOBT (2.9 μL, 0.4 M in DMF, 1.16 μmol), HBTU (4.5 μL, 0.2 M in DMF, 0.9 μmol) and 20% DIPEA in DMF (2.7 μL) to a well. The wells were capped and the plate was incubated at room temperature for 3 h. Aliquots (2.5 μL, 50 mM, 0.12 μmol) from the activated acid solutions were then added to a different 96 well plate 2 (7.5 μL, 13.5 mM in DMF, 0.1 μmol) in each well and mixed. The plate was covered with an aluminum lid and incubated at room temperature overnight. The reaction mixtures were then quenched by adding 0.1 mL/well $H_2O$ and evaporated to dryness in vacuo to obtain pro-3, which was used directly in the next step without purification.

Deprotection to Produce 3 for Library Screening.

The plate containing the library of pro-3 was treated with ACN containing 2% $H_2O$ (30 μL/well) and a solution of $BF_3*Et_2O$ in ACN (3 μL, 0.56 M, 1.7 μmol) and contents of each well were mixed. The plate was covered with an aluminum lid and incubated at room temperature for 1.5 h.

The reaction mixture in each well was diluted to 150 μL with phosphate buffer (20 mM, pH 7.2) containing NaCl (0.2 μM). These solutions (0.675 mM) were used in the fluorescence screening assay and stored at −20° C.

Screening of the Inhibitors.

A working solution of Pol β (125 nM, 200 μL) was prepared in 1× Pol β reaction buffer (50 mM HEPES buffer pH=7.5, 5 mM MgCl$_2$, 0.2 mM EDTA, 50 mM KCl and 0.01% Tween 20), containing BSA (0.1 mg/mL), and 30% glycerol (in autoclaved water). Pol β (8.0 μL, 125 nM) was added to each well of a 96 well fluorescence spectrometer plate containing a solution of a different inhibitor (11.6 μM, 172 μL) in 1× Pol β reaction buffer and the mixtures were per-incubated for 25 min at room temperature. The pre-incubation mixtures were subsequently diluted with a solution (20 μL) containing 14 (500 nM) and dTTP (1 mM) in 1× Pol β reaction buffer and fluorescence was monitored for approximately 100 min.

Time Dependent Inactivation of Pol β by 13.

A working solution of Pol β (12.5 nM) was prepared in 1× Pol β reaction buffer containing 30% glycerol and kept at 0° C. during the experiment. Pol β (2 nM) was pre-incubated with 13 (0, 0.25, 1.0, 1.5 μM) in 1× Pol β reaction buffer at room temperature. Aliquots (24 μL) were withdrawn at the appropriate time intervals depending on the concentration of 13, and added to 15 (2 μL, 2.5 μM) in 1× Pol β reaction buffer to start the lyase reactions. Aliquots (4 μL) were removed from the individual reactions at the indicated time points (2, 5, 10, 15, 20, 25 min) and stabilized by reducing unreacted 15 with NaBH$_4$ solution (2 μL, 0.5 μM). The aliquots were kept at 4° C. for 1 h and at room temperature for 3 h before mixing with loading buffer (6 μL) and separating by 20% denaturing PAGE.

Effect of Dialysis on Pol β Inactivated by 13.

Pol β (3 nM) in 1× reaction buffer was preincubated in the absence or presence of 13 (3 μM) for 30 min at room temperature. The Pol β lyase activity of each sample was immediately measured using 15 as described above. Three aliquots (500 μL) were dialyzed in reaction buffer (2×1 L; buffer was exchanged after 12 h) containing 10% glycerol for 24 h. The remaining lyase activity of the enzyme was measured (24 μL aliquots, after 0 and 1 day) using 15 (2 μL, 2.5 μM) as described above. Aliquots (4 μL) were removed at indicated time points (2, 5, 10, 15, 20, 25 min) and stabilized with NaBH$_4$ solution (2 μL, 0.5 M). The aliquots were kept at 4° C. for 1 h and at room temperature for 3 h before mixing with loading buffer (6 μL) and separating by 20% denaturing PAGE. IC$_{50}$ value for Pol f. A working solution of Pol β (62.5 nM) was prepared in 1× Pol β reaction buffer containing 30% glycerol and kept at 0° C. during the experiment. Pol β (2.5 nM) was preincubated with 13 (0, 0.2, 0.4, 0.6, 0.8, 1.0, 1.5, 2.0, 3.0 μM) for 30 min in 1× Pol β reaction buffer. All of the reaction mixtures contained 0.75% acetonitrile by volume. Aliquots (24 μL) were mixed with 15 (2 μL, 2.5 μM) in 1× Pol β reaction buffer to start the lyase reactions. Aliquots (4 μL) were removed from the individual reactions at the indicated time points (2, 5, 10, 15, 20, 25 min) and stabilized by reducing unreacted 15 with NaBH$_4$ solution (2 μL, 0.5 μM). The aliquots were kept at 4° C. for 1 h and at room temperature for 3 h before mixing with loading buffer (6 μL) and separating by 20% denaturing PAGE. The relative activities were fit to the following sigmoidal equation: Relative Activity=A2+[(A1−A2)/(1+(x/x0)^P)], where x=concentration of inhibitor, A2=minimum enzyme activity, A1=maximum enzyme activity, x0=IC$_{50}$, and p-Hill slope, which characterizes the slope of the curve at its midpoint. The data were fit iteratively using Origin 6.1.

IC$_{50}$ value for 13 against Pol λ.

A working solution of Pol λ (125 nM) was prepared in 1× Pol β reaction buffer containing 30% glycerol and kept at 0° C. during the experiment. Pol λ (15 nM) was pre-incubated with 13 (0, 0.05, 0.1, 0.2, 0.3, 0.4, 0.6, 0.8, 1.2 μM) for 30 min in 1× Pol β reaction buffer. All of the reaction mixtures contained 0.25% acetonitrile by volume. Aliquots (24 μL) were mixed with 15 (2 μL, 2.5 μM) and reactions and analysis were carried out as described above for Pol β.

General Methods

Preparation of DMT-Azide 5.

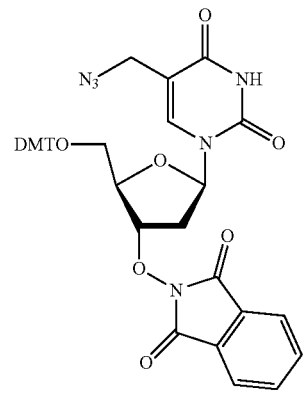

5

Phthalimide 4, Chen et al., 2010, (0.6 g, 0.87 mmol) was azetropically dried (3×3 mL) and resuspended in dry benzene (13 mL). N-Bromosuccinimide (245 mg, 1.38 mmol) and AIBN (30 mg, 0.18 mmol) were added and the mixture was stirred at 85° C. for 1 h at which time silica TLC indicated most (approximately 80%) of 4 was consumed. The reaction mixture was concentrated under reduced pressure. The residue was dissolve in dry DMF (8 mL) and NaN$_3$ (350 mg, mmol) was added. The mixture was stirred at room temperature overnight. The reaction was diluted with EtOAc (80 mL), washed with sat. aq. NaHCO$_3$ solution (40 mL), brine (30 mL), dried over Na$_2$SO$_4$, and concentrated under reduced pressure. The residue was purified by flash column chromatography on a silica gel column (25×3 cm). Elution with 1:2→2:3→1:1 ethyl acetate-hexane gave 5 (285 mg, 45%) as a colorless foam. Silica gel TLC R$_f$=0.60 (1:10:10 methanol-ethyl acetate-hexane); $^1$H NMR (CDCl$_3$) δ 8.85 (s, 1H), 7.90-7.67 (m, 5H), 7.37-7.26 (m, 3H), 7.26-7.14 (m, 6H), 6.81 (dd, J=9.0, 1.0 Hz, 4H), 6.59 (dd, J=8.5, 5.6 Hz, 1H), 5.11 (d, J=6.0 Hz, 1H), 4.53 (d, J=2.0 Hz, 1H), 3.78 (s, 6H), 3.58-3.29 (m, 4H), 2.87 (dt, J=13.0, 6.0 Hz, 1H), 2.35 (ddd, J=14.5, 8.5, 6.0 Hz, 1H); $^{13}$C NMR (CDCl$_3$) δ 177.9, 163.8, 162.58, 162.57, 159.2, 158.82, 158.79, 149.8, 144.1, 138.7, 135.1, 135.0, 134.8, 130.1, 130.0, 128.7, 128.7, 128.10, 128.08, 127.3, 123.9, 113.4, 110.0, 88.0, 87.22, 87.22, 85.4, 84.9, 82.7, 63.5, 62.8, 55.2, 47.0, 46.6, 44.9, 37.5, 35.4, 31.6, 30.2, 29.6, 22.6, 21.0, 14.1; HRMS (ESI-TOF) C$_{39}$H$_{34}$N$_6$O$_9$Na (M+Na)+ calcd. m/z 753.2285, found 753.2272.

Preparation of TBS-Aldehyde 9.

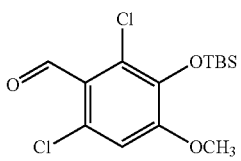

9

N,N-Dimethylaminopyridine (25 mg, 0.2 mmol) followed by TBSCl (101 mg, 0.67 mmol) were added to a solution of 8, Arian et al., 2014, (115 mg, 0.53 mmol) in dry $CH_2Cl_2$ (3 mL) containing triethylamine (0.5 mL, 0.36 g, 3.59 mmol) at 0° C. and the mixture was stirred at room temperature overnight. The reaction was diluted with $CH_2Cl_2$ (30 mL), washed with sat. aq. $NH_4Cl$ solution (20 mL), brine (20 mL), dried over $Na_2SO_4$, and concentrated under reduced pressure. The residue was purified by flash column chromatography on a silica gel column (15×2 cm). Elution with 1:9-1:4 ethyl acetate-hexane gave 9 (162 mg, 91%) as a colorless foam. Silica gel TLC $R_f$=0.64 (1:9 ethyl acetate-hexane); $^1H$ NMR (CDCl$_3$) δ 10.40 (s, 1H), 6.84 (s, 1H), 3.88 (s, 3H), 1.16-0.92 (m, 9H), 0.19 (s, 6H); $^{13}C$ NMR (CDCl$_3$) δ 188.6, 154.8, 141.7, 130.1, 129.0, 123.2, 112.3, 55.9, 25.9, 19.0, –3.8; HRMS (EI-magnetic sector instrument) $C_{14}H_{21}N_3O_3Cl_2Si$ (M+H)+ calcd. m/z 335.0637, found 335.0639.

Preparation of DMT-TBS-Oxime 6.

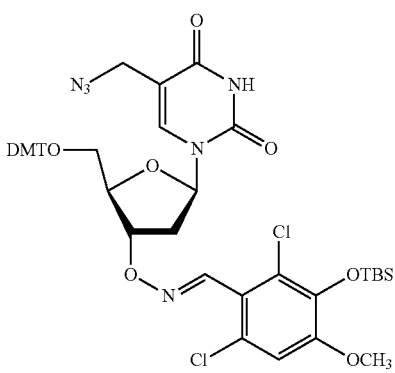

6

An aq. solution (8%) of methylamine (0.5 mL) was added to a solution of 5 (300 mg, 0.41 mmol) in THF (6 mL) and the resulting solution was stirred at room temperature for 2 h. The reaction mixture was concentrated and the residue was coevaporated with MeOH (3×5 mL). The residue was suspended in MeOH (2.4 mL) and a solution of 9 (150 mg, 0.45 mmol) in THF (0.6 mL) was added, followed by AcOH (approximately 25 μL). The reaction mixture was stirred at room temperature overnight and concentrated. The residue was purified by flash column chromatography on a silica gel column (25×2 cm). Elution with 1:3→1:2 ethyl acetate-hexane gave 6 (296 mg, 78%) as a colorless foam. Silica gel TLC $R_f$=0.87 (1:10:10 methanol-ethyl acetate-hexane); $^1H$ NMR (CDCl$_3$) δ 9.71 (d, J=16.1 Hz, 1H), 8.30 (s, 1H), 7.92 (d, J=4.7 Hz, 1H), 7.46-7.37 (m, 2H), 7.35-7.25 (m, 7H), 6.92-6.82 (m, 5H), 6.53 (dt, J=14.2, 7.1 Hz, 1H), 5.15 (d, J=6.4 Hz, 1H), 4.41 (d, J=2.0 Hz, 1H), 3.79 (dd, J=7.5, 4.1 Hz, 9H), 3.62-3.41 (m, 3H), 3.27 (t, J=15.6 Hz, 1H), 2.80 (dd, J=13.2, 5.8 Hz, 1H), 2.50-2.35 (m, 1H), 1.05-1.01 (m, 9H), 0.20-0.18 (m, 6H); $^{13}C$ NMR (101 MHz, CDCl$_3$) δ 162.7, 158.8, 158.8, 151.8, 150.1, 146.9, 144.2, 141.3, 139.2, 135.3, 135.1, 130.2, 130.1, 128.2, 128.1, 127.3, 126.7, 126.1, 120.9, 113.4, 111.8, 110.0, 87.1, 85.1, 83.7, 83.6, 64.0, 55.6, 55.27, 55.26, 46.5, 38.4, 25.9, 18.9, –4.0; HRMS (ESI-TOF) $C_{45}H_{50}C_2N_6O_9SiNa$ (M+Na)+ calcd. m/z 939.2683, found 939.2665.

Preparation of TBS-Oxime 7.

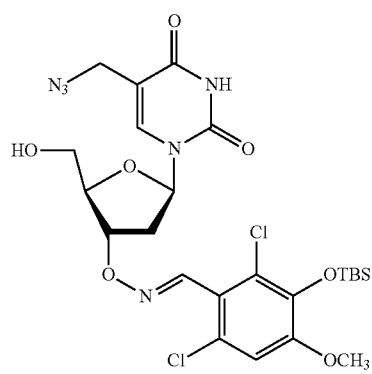

7

A solution of 6 (392 mg, 0.43 mmol) in 85% aq. AcOH (15 mL) was stirred at room temperature for 1.5 h and diluted with MeOH (20 mL). The reaction mixture was concentrated under reduced pressure and the residue was purified by flash column chromatography on a silica gel column (20×2 cm). Elution with 1:3→1:2→2:3 ethyl acetate-hexane gave 7 (220 mg, 84%) as a colorless oil. Silica gel TLC $R_f$=0.72 (1:10:10 methanol-ethyl acetate-hexane); $^1H$ NMR (CDCl$_3$) δ 8.46 (s, 1H), 8.30 (s, 1H), 7.87 (s, 1H), 6.85 (s, 1H), 6.32 (dd, J=7.9, 6.0 Hz, 1H), 5.03 (d, J=6.7 Hz, 1H), 4.39 (d, J=2.2 Hz, 1H), 4.20-4.14 (m, 2H), 3.98 (dt, J=11.8, 10.5 Hz, 2H), 3.83 (s, 3H), 2.67 (dd, J=14.1, 4.0 Hz, 1H), 2.53-2.37 (m, 1H), 1.02 (s, 9H), 0.20 (d, J=3.0 Hz, 6H); $^{13}C$ NMR (CDCl$_3$) δ 162.7, 151.9, 150.2, 146.9, 141.5, 139.7, 126.7, 126.2, 121.0, 111.9, 109.9, 87.4, 85.1, 83.1, 63.2, 55.7, 47.4, 37.7, 26.0, 19.0, -3.9; HRMS (ESI-TOF) $C_{24}H_{33}C_{12}N_6O_7Si$ (M+H)+ calcd. m/z 615.1557, found 615.1552.

Preparation of Phosphoramidite 11.

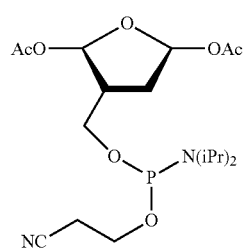

11

Alcohol 10, Arian et al., 2014, (110 mg, 0.50 mmol) was dried under vacuum overnight, dissolved in anhydrous $CH_2Cl_2$ (4 mL), and cooled to 0° C. N,N-Diisopropylethylamine (0.37 g, 0.5 mL, 2.89 mmol), followed by 2-cyanoethyl N,N-diisopropylchlorophosphoramidite (159 mg, 150 μL, 0.67 mmol) were added. The mixture was stirred at 0° C. for 15 min and at room temperature for 1 h. The reaction mixture was diluted with EtOAc (50 mL) and sat. aq. NaHCO$_3$ solution (20 mL). The organic layer was separated, washed with brine (15 mL), dried over anhydrous Na$_2$SO$_4$ and concentrated under reduced pressure. The residue was purified by flash column chromatography on a silica gel column (20×1 cm). Elution with 1:3→1:2 ethyl acetate-hexane gave 11 (100 mg, 48%) as a colorless foam. Silica gel TLC R$_f$=0.79 (1:10:10 methanol-ethyl acetate-hexane); $^1$H NMR (CDCl$_3$) δ 6.43-6.17 (m, 2H), 3.90-3.38 (m, 6H), 2.81-2.33 (m, 4H), 2.15-1.95 (m, 6H), 1.81 (ddt, J=13.4, 11.1, 4.6 Hz, 1H), 1.12 (dt, J=7.1, 3.7 Hz, 12H); $^{31}$P NMR (CDCl$_3$) δ 148.3, 148.0.

Preparation of the TBS-Phosphate Triester Precursor to 12.

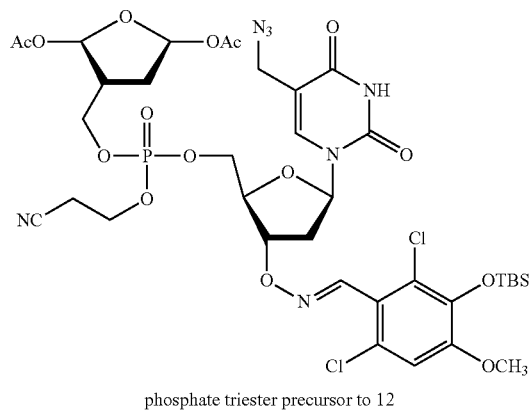 [SMILES: COc1cc(Cl)c(/C=N/O[C@@H]2C[C@H](n3cc(CN=[N+]=[N-])c(=O)[nH]c3=O)O[C@@H]2COP(=O)(OCCC#N)OC[C@@H]2C[C@H](OC(C)=O)O[C@@H]2OC(C)=O)c(Cl)c1O[Si](C)(C)C(C)(C)C]

phosphate triester precursor to 12

Alcohol 7 (280 mg, 0.46 mmol) was azeotropically dried with pyridine (3×3 mL) and dissolved in the activator solution (5.5 mL, 0.25 M Sethyltetrazole in THF, 1.4 mmol). This solution was then added to a reaction flask containing 11 (192 mg, 0.46 mmol) under argon and the mixture was stirred at room temperature for 30 min. A solution of tert-butyl hydroperoxide in decane (0.2 mL, 7 M, 1.4 mmol) was added and the mixture was stirred at room temperature for 1 h. The reaction mixture was concentrated, diluted with EtOAc (60 mL), and washed with sat. aq. NaHCO$_3$ (15 mL), H$_2$O (20 mL), and brine (15 mL). The EtOAc layer was dried over Na$_2$SO$_4$ and concentrated under reduced pressure. The residue was purified by flash column chromatography on a silica gel column (25×2 cm). Elution with 1:2 ethyl acetate-hexane→0.1:3:2 methanol-ethyl acetate-hexane gave the phosphate triester precursor to 12 (270 mg, 62%) as a colorless foam. Silica gel TLC R$_f$=0.28 (1:10:10 methanol-ethyl acetate-hexane); $^1$H NMR (CDCl$_3$) δ 9.77 (t, J=13.0 Hz, 1H), 8.27 (s, 1H), 7.77 (s, 1H), 6.83 (s, 1H), 6.48-6.19 (m, 3H), 5.04-4.78 (m, 1H), 4.52-4.10 (m, 9H), 3.81 (d, J=5.9 Hz, 3H), 2.98-2.34 (m, 5H), 2.25 (dd, J=13.5, 6.1 Hz, 1H), 2.11-2.01 (m, 6H), 1.92-1.75 (m, 1H), 0.98 (s, 9H), 0.15 (s, 6H); $^{31}$P NMR (CDCl$_3$) δ −1.8, −1.9, −2.0; HRMS (ESI-TOF) C$_{36}$H$_{48}$N$_7$O$_{15}$SiNaPCl$_2$ (M+Na)+ calcd. m/z 970.1990, found 970.1947.

Preparation of 12.

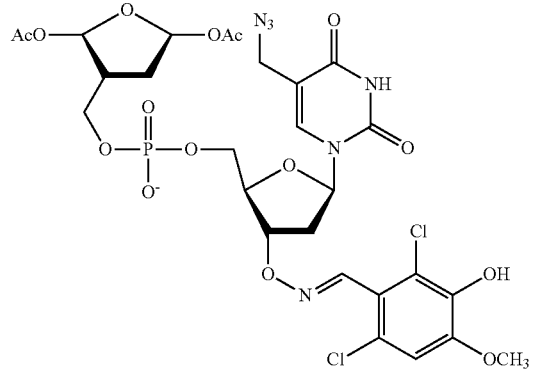 [SMILES: COc1cc(Cl)c(/C=N/O[C@@H]2C[C@H](n3cc(CN=[N+]=[N-])c(=O)[nH]c3=O)O[C@@H]2COP(=O)([O-])OC[C@@H]2C[C@H](OC(C)=O)O[C@@H]2OC(C)=O)c(Cl)c1O]

The phosphate triester precursor to 12 (22 mg, 23 μmol) was dissolved in 1:3 mixture of CH$_2$Cl$_2$-Et$_3$N (4 mL) and the mixture was heated to 60° C. for 16 h. The reaction mixture was concentrated under reduced pressure and the residue was diluted with H$_2$O (8 mL), washed with CH$_2$Cl$_2$ (2×5 mL), and EtOAc (5 mL). The aqueous layer was lyophilized to obtain 12 (15 mg, 83%) as a light yellow solid. TLC R$_f$=0.72 (0.1:1:9 triethylamine-methanol-dichloromethane); $^1$H NMR (D$_2$O) δ 8.22 (s, 1H), 7.96 (s, 1H), 6.92 (s, 1H), 6.30 (s, 1H), 6.21-6.04 (m, 2H), 4.96 (s, 1H), 4.39 (s, 1H), 4.16-3.85 (m, 6H), 3.78 (s, 3H), 2.77-2.21 (m, 4H), 2.04-1.90 (m, 6H), 1.76 (m, 1H); $^{31}$P NMR (D2O) δ −0.2; HRMS (ESI-TOF) 27H30N6O15PCl2 (M−H)− calcd. m/z 779.0841, found 779.0884.

Preparation of Pro-13 from the TBS-Phosphate Triester Precursor to 12 (Scheme 12).

pro-13

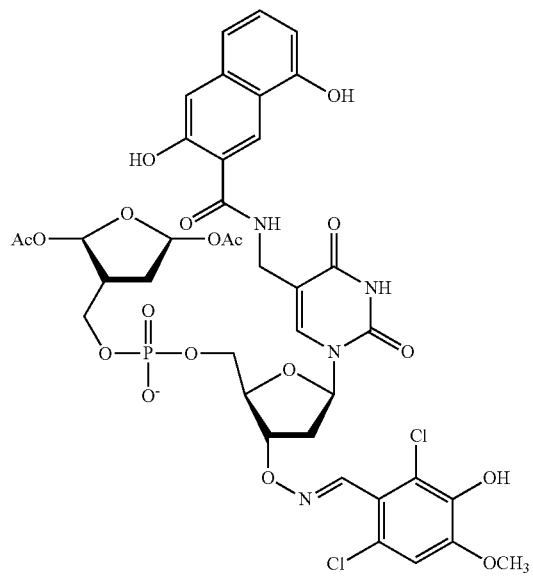

AcOH (50 μL) and palladium on carbon (5 mg, 10% by wt.) were added to a solution containing the phosphate triester protected precursor of 12 (9 mg, 9.5 μmol). The resulting suspension was bubbled with H$_2$ for 10 min and then stirred at room temperature for 2 h under H$_2$. The reaction mixture was filtered and concentrated to obtain protected amine (S1), see Scheme 12, which was used for the next step without any purification; yield 7.5 mg (85%).

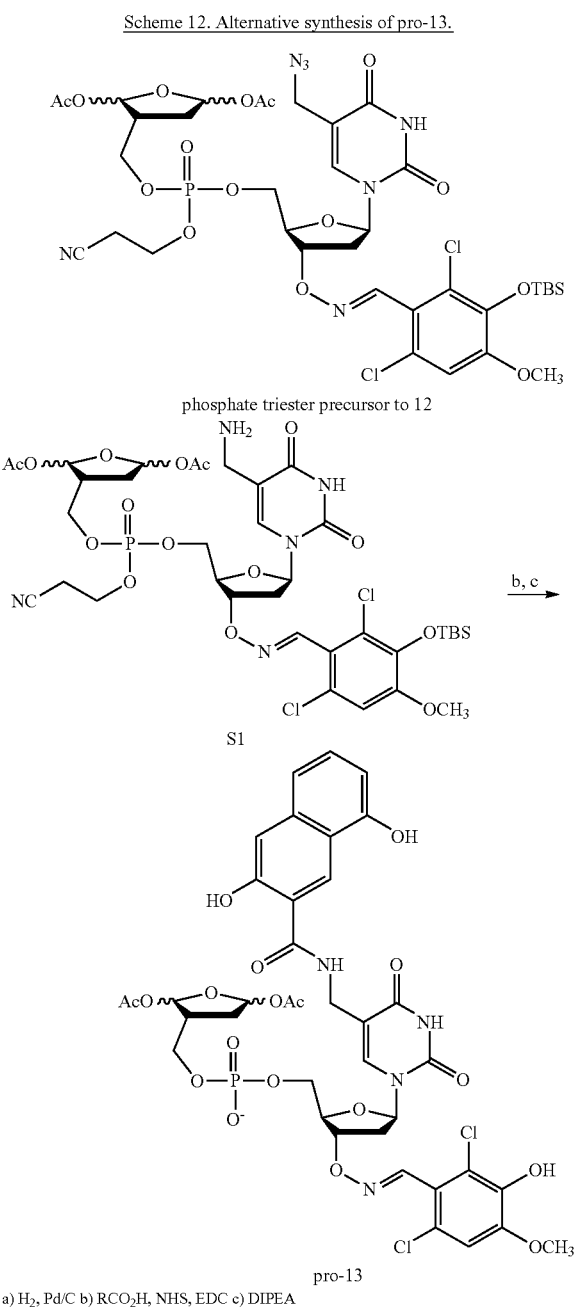

Scheme 12. Alternative synthesis of pro-13.

a) H₂, Pd/C  b) RCO₂H, NHS, EDC  c) DIPEA

Dihydroxy naphthalene carboxyl acid (100 µL, 0.2 M, 20 µmol in DMF), N-hydroxysuccinimide (200 µL, 0.2 M, 20 µmol in DMF), and 1-ethyl-3-(3-dimethylaminopropyl)carbodiimide (100 µL, 0.2 M, 20 µmol in DMF) was incubated at room temperature for 2 h. The solution containing the activated acid was then treated with a solution of Si (7.5 mg, 8.1 µmol) in DMF (0.9 mL) and phosphate buffer (pH 7.2, 10 mM, 1 mL). The mixture was incubated at room temperature overnight. The mixture was subsequently concentrated to approximately 0.2 mL and treated with a solution of DIPEA in DMF (33% by vol., 1.5 mL). The mixture was incubated 55° C. for 4 h, and purified by reverse phase HPLC on a C18 column, Waters Delta Pak 300×7.8 mm. A gradient of 5→40% ACN in 0.1 M aq. ammonium acetate over 15 min and a second gradient of 40→100% ACN in 0.1 M aq. ammonium acetate over 2 min was employed at a flow rate of 5 mL/min. The peak at 14.0 min was collected and lyophilized to obtain pro-13 (1.5 mg, 19%) as a yellow solid. $^1$H NMR (CD$_3$CN-D$_2$O, a few drops of D$_2$O) δ 8.51-8.47 (m, 1H), 8.37-8.17 (m, 2H), 7.93 (s, 1H), 7.54-7.34 (m, 1H), 7.14-6.80 (m, 2H), 6.32-6.10 (m, 4H), 4.97 (br s, 1H), 4.49-4.16 (m, 4H), 4.06-3.87 (m, 7H), 3.85 (m, 6H), 2.63-2.47 (m, 1H), 2.38-2.30 (m, 2H), 2.11-2.09 (m, 1H), 2.02-1.96 (m, 6H); $^{31}$P NMR (CD$_3$CN-D$_2$O, a few drops of D$_2$O) δ −0.7; HRMS (ESITOF) C$_{38}$H$_{38}$Cl$_2$N$_4$O$_{18}$P (M−H)− calcd. m/z 939.1296, found 939.1304.

Preparation of 13.

A suspension of pro-13 (1.0 mg, 0.94 µmol) in ACN containing 2% H$_2$O (1 mL) was treated with a solution of BF$_3$-Et$_2$O in ACN (100 µL, 0.4 M, 0.04 mmol) at room temperature for 1.0 h at which time analysis by C18-HPLC analysis showed complete disappearance of pro-13 and formation of 13. The reaction mixture was diluted with phosphate buffer (1 mL, 10 mM, pH 7.2) and concentrated to approximately 0.5 mL. The crude mixture was purified by a C18 silica plug in a Pasteur pipette (2 inches). Elution with 0%→20% ACN in H$_2$O gave of 13 (0.4 mg, 44%). $^1$H NMR (DMSO-d$_6$) δ 8.45-8.20 (m, 2H), 8.03-7.80 (m, 1H), 7.64-7.23 (m, 1H), 7.98-6.65 (m, 3H), 6.45-5.98 (m, 2H), 5.35-4.81 (m, 3H), 4.01-3.65 (m, 8H), 3.15-2.69 (m, 3H), 2.15-1.77 (m, 4H); $^{31}$P NMR (CD$_3$CN-D$_2$O) δ 0.45; HRMS (ESI-TOF) C$_{34}$H$_{34}$C$_{12}$N$_4$O$_{16}$P (M−H)− m/z calcd. 855.1055, found 855.1030.

Deoxyribose Phosphate (dRP)—Aldehyde Reactive Probe (ARP) Adduct Formation.

To study the reactivity of ARP towards deoxyribose phosphate (dRP), the photochemical precursor to 15 (~20,000 cpm) was diluted to 30 L in 1×PBS. Arian et al., 2014. A 6 µL of solution was removed as unphotolyzed control. The remaining solution (24 µL) was photolyzed (350 nm in a Rayonet photoreactor) for 10 min at room temperature. Immediately after photolysis, two aliquots (6 µL) were removed from the reaction. One aliquot was treated with 0.1 N NaOH at 37° C. for 30 min and the other with NaBH$_4$ (0.1 µM) for 1 h at 4° C. The NaOH treated sample was then neutralized with 0.1 N HCl. The other two aliquots (6 μL each) were treated with 10 L of ARP solution (from DNA damage quantification kit from Dojindo Molecular Technologies (DK02-12)). One of the reactions was quenched with $NaBH_4$ (0.1 M, final concentration). All of the aliquots were then analyzed directly by 20% denaturing PAGE (40×32×0.04 cm). The gel was run under limiting power (55 W) until the bromophenol blue band migrated to the bottom.

Cell Culture.

HeLa (human cervical carcinoma) cells were maintained in Dulbecco's Modified Eagle's Medium (DMEM), supplemented with 10% fetal bovine serum (FBS), 100 U $mL^{-1}$ of penicillin and 100 μg $mL^{-1}$ of streptomycin at 37° C. in a humidified incubator at 5% $CO_2$. The adherent cultures were grown as a monolayer and passaged once after 3-4 days by trypsinizing with 0.25% Trypsin-EDTA. At 90% confluency, there are around $1.5 \times 10^7$ cells in one dish of 150 mm×25 mm. Cell viability assay. Approximately 106 HeLa cells were plated in each well of a 6 well culture plate (well size; 35 mm×18 mm) in DMEM containing 10% FBS (2 mL) and kept for 24 h at 37° C. in a $CO_2$ incubator. After the indicated time, the medium was removed from the cell culture by aspiration, and washed once with PBS. A stock solution of bleomycin sulphate (1 mM) in DMSO was diluted in the culture medium to 2 μM and then added to the plates keeping the quantity of DMSO constant at 1% for all tests. Cells were then incubated for 2 h at 37° C. in a $CO_2$ incubator. The medium was then subsequently replaced with fresh DMEM-FBS and incubation was continued for an additional 1 or 2 h at 37° C. in a $CO_2$ incubator. After the indicated time, cells were trypsinized with 0.25% w/v Trypsin-EDTA (100 μL in each well, 2 min incubation at 37° C.) and the cell suspension was prepared in 1 mL PBS. A portion (10 μL) of the cell suspension was thoroughly mixed with 10 μL of 0.4% solution of trypan blue in PBS (pH 7.2 to 7.3), and placed on a counting slide (BIO-RAD) to count the % of live cells using a TC20 automated cell counter (BIO-RAD). A control experiment without treating with bleomycin sulphate was carried out in parallel. All the experiments were carried out at least 3 times, and each experiment consisted of 3 replicates.

Comet Assay to Visualize DNA Damage in Bleomycin Treated Cells.

Bleomycin sulphate treatment of HeLa cells was carried out exactly in the same way as described above. The only difference was that approximately $2 \times 10^7$ HeLa cells were plated in each well of the 6 wells culture plate. After the required incubation steps, the medium was aspirated from the cell culture, and washed with PBS (3×) by adding 5 mL of PBS to each well, scratching with a cell scraper (3 cm blade) and transferring the cells to a 15 mL Falcon tube. Cells were pelleted by centrifuging at 3000 g for 10 min at room temperature. Cells were resuspended in PBS and pelleted again. For the comet assay, cells were suspended in 2 mL PBS/well and counted (generally approximately $1 \times 10^7$/mL). An aliquot (10 μL) of the cell suspension was diluted to $1 \times 10^5$ cells/mL using PBS and used in an Oxiselect™ Comet Assay Kit (Cell Biolabs, INC. Catalog number STA-350) according to the product manual (www.cellbiolabs.com/sites/default/files/STA-350-comet-assay-kit.pdf). In brief, cell samples were combined with Comet Agarose at 1:10 ratio (v/v), titrurated with a pipette to mix, and immediately pipette 75 μL/well onto the OxiSelect™ Comet Slide. Ensure complete well coverage by spreading the suspension over the well with the pipette tip (Note: For multiple samples, maintain suspensions at 37° C. in a water bath to avoid gelation). Maintaining the slide horizontally, transfer the slide to 4° C. in the dark for 15 min. Carefully transfer the slide to a container containing pre-chilled lysis buffer (from the Kit; approximately 25 mL/slide). Immerse the slide in the buffer for 60 min at 4° C. in the dark. Carefully, aspirate the lysis Buffer from the container and replace with pre-chilled alkaline solution (from the Kit), pH>13 (approximately 25 mL/slide). Immerse the slide in the solution for 30 min at 4° C. in the dark. Maintaining the slide horizontally, carefully transfer the slide from the alkaline solution to a horizontal electrophoresis chamber. Fill the chamber with cold alkaline electrophoresis solution (300 mM NaOH, 1 mM EDTA, pH>13) until the buffer level covers the slide. Apply voltage to the chamber for 30 min at 1 volt/cm electrode distance. In addition, adjust the volume of alkaline electrophoresis solution to produce a current of 300 mA. Maintaining the slide horizontally, carefully transfer the slide from the electrophoresis chamber to a clean and small container containing pre-chilled $H_2O$ (approximately 25 mL/slide). Immerse the slide for 2 min, aspirate, and then repeat twice more. Aspirate the final water rinse and replace with cold 70% ethanol solution for 5 min. Maintaining the slide horizontally, remove the slide from the 70% ethanol solution and allow to air dry. Once the agarose and slide are completely dry, add 100 μL/well of 1× Vista Green DNA Dye (from the Kit). Incubate at room temperature for 15 min. View slides by a fluorescence microscopy using a FITC filter. A control experiment without any bleomycin sulphate treatment was carried out in parallel. All the experiments were carried at least 3 times each consisting of 3 replicates. The relative tail lengths were determined with Open Comet software.

Clonogenic Assay for Cell Survival.

HeLa cells ($2 \times 10^5$) were seeded in each well of a 24 well culture plate (well size; 15.5 mm×18 mm) in 1 mL Dulbecco's Modified Eagle Medium (DMEM) growth medium supplemented with 10% FBS. After overnight incubation at 37° C. in a humidified atmosphere of 5% $CO_2$, cells were subjected to the appropriate DNA damaging conditions (or controls). For alkylation experiments, cells were incubated with MMS (0, 0.1, or 0.2 mM), with or without pro-13 (5 μM) for 1 or 2 h. For experiments involving recovery after MMS treatment, the medium containing MMS and/or pro-13 was replaced after 2 h with fresh medium with or without pro-13 (5 μM) and incubation continued for 2-8 h. For BLM experiments, cells were incubated with BLM (2 μM), with or without pro-13 (5 μM) for 2 h, at which time the medium was replaced with fresh medium containing only pro-13 (5 μM) and incubation was continued for 2 h. The growth medium was then removed from each well and the cells were washed with PBS (2×1 mL). The cells were treated for 2 min with 0.25% Trypsin-EDTA (50 μL in each well) at 37° C. to detach them from the plates and then diluted in DMEMFBS medium (0.5 mL/well). The single cell suspensions were collected in 1.6 mL tubes and counted using a Bio-Rad TC20 Automated Cell Counter. Stock solutions of single cell suspensions were made in two groups for each concentration with 500 cells/mL (for untreated control) and 1500 cells/mL (for treated cells), respectively. These cells were seeded in 6 well plates (well size; 35 mm×18 mm) in 2 mL of 10% DMEM-FBS. The plates were incubated in humidified atmosphere with 5% $CO_2$ for 7 days. After 7 days, the growth medium was discarded and the attached cells were treated with 0.2% w/v crystal violet solution. The excess dye was washed with water and the colonies were counted under a stereomicroscope. Plating efficiencies (PE) and survival fractions (SF) were calculated as follows: PE=number of colonies+number of cells seeded; SF=PE+PE (control).

AP/dRP Site Accumulation in Genomic DNA of HeLa Cells.

HeLa cells (approximately $1 \times 10^7$) were plated in 150 mm×25 mm dishes and treated with DMSO (1% final concentration), MMS (0.3 or 0.4 mM), or pro-13 (5 µM) alone or with a combination of MMS (0.3 or 0.4 mM), and pro-13 (5 µM) for 1 h at 37° C. The cellular medium was then replaced with fresh DMEM-FBS and incubation was continued for 23 h at 37° C. in a $CO_2$ incubator in the absence or presence of pro-13 (5 µM). Cells were then harvested with 0.25% Trypsin-EDTA, and the genomic DNA of each sample was isolated according to Dojindo Genomic DNA isolation kit (www.dojindo.com/TechnicalManual/Manual_GKO3.pdf). The concentration of genomic DNA was measured at 260 nm and adjusted to 100 ng/µL. An aliquot of purified DNA (1 µg) was labeled with 10 µL of aldehyde reactive probe (ARP) reagent (N'-aminooxymethylcarbonylhydrazino-D-biotin), and AP/dRP sites were determined using the DNA damage quantification kit from Dojindo Molecular Technologies (DK02-12) by measuring the absorbance at 650 nm using an ELISA microplate reader (BioRad).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Absalon, M. J., Wu, W., Kozarich, J. W., and Stubbe, J. (1995a) Sequence-specific doublestrand cleavage of DNA by Fe-bleomycin. 2. Mechanism and dynamics, *Biochemistry* 34, 2076-2086.

Absalon, M. J., Kozarich, J. W., and Stubbe, J. (1995b) Sequence specific double-strand cleavage of DNA by Fe-bleomycin. 1. The detection of sequence-specific double-strand breaks using hairpin oligonucleotides, *Biochemistry* 34, 2065-2075.

Albertella, M. R.; Lau, A.; O'Connor, M. J. *DNA Repair* (2005), 4, 583.

Arian, D., Hedayati, M., Zhou, H., Bilis, Z., Chen, K., DeWeese, T. L., and Greenberg, M. M. (2014) Irreversible inhibition of DNA polymerase β by small-molecule mimics of a DNA lesion, *J. Am. Chem. Soc.* 136, 3176-3183.

Asaeda, A., Ide, H., Terato, H., Takamori, Y., and Kubo, K. (1998) Highly sensitive assay of DNA abasic sites in mammalian cells-optimization of the aldehyde reactive probe method, *Anal. Chim. Acta* 365, 35-41.

Barakat, K., Gajewski, M., and Tuszynski, J. A. (2012a) DNA repair inhibitors: the next major step to improve cancer therapy, *Curr. Top. Med. Chem.* 12, 1376-1390.

Barakat, K. H., Gajewski, M. M., and Tuszynski, J. A. (2012b) DNA polymerase beta (Pol β) inhibitors: A comprehensive overview, *Drug Discovery Today* 17, 913-920.

Beard, W. A., and Wilson, S. H. (2006) Structure and mechanism of DNA polymerase β, *Chem. Rev.* 106, 361-382.

Boeckman, R. K.; Miller, J. R. (2009) *Org. Lett.*, 11, 4544-4547.

Bournaud, C.; Marchal, E.; Quintard, A.; Sulzer-Mossé, S.; Alexakis, A. (2010) *Tet. Asym.*, 21, 1666-1673.

Braithwaite, E. K., Kedar, P. S., Stumpo, D. J., Bertocci, B., Freedman, J. H., Samson, L. D., and Wilson, S. H. (2010) DNA Polymerases β and λ mediate overlapping and independent roles in base excision repair in mouse embryonic fibroblasts, *PLoS One* 5, e12229.

Braithwaite, E. K., Prasad, R., Shock, D. D., Hou, E. W., Beard, W. A., and Wilson, S. H. (2005) DNA polymerase lambda mediates a back-up base excision repair activity in extracts of mouse embryonic fibroblasts, *J. Biol. Chem.* 280, 18469-18475.

Chen, F., Gaucher, E. A., Leal, N. A., Hutter, D., Havemann, S. A., Govindarajan, S., Ortlund, E. A., and Benner, S. A. (2010) Reconstructed evolutionary adaptive paths give polymerases accepting reversible terminators for sequencing and SNP detection, *Proc. Natl. Acad. Sci. USA* 107, 1948-1953.

Chung, S.; Parker, J. B.; Bianchet, M.; Amzel, L. M.; Stivers, J. T. (2009) *Nat. Chem. Biol.*, 5, 407-413.

Deterding, L. J.; Prasad, R.; Mullen, G. P.; Wilson, S. H.; Tomer, K. B. (2000) *J. Biol. Chem.*, 275, 10463-10471.

Dianov, G. L., and Hubscher, U. (2013) Mammalian base excision repair: the forgotten archangel, *Nucleic Acids Res.* 41, 3483-3490.

Dzdaroglu, M. (2015) Oxidatively induced DNA damage and its repair in cancer, *Mutat. Res. Rev. Mutagenesis* 763, 212-245.

Donigan, K. A.; Hile, S. E.; Eckert, K. A.; Sweasy, J. B. (2012a) *DNA Repair*, 11, 381-390.

Donigan, K. A., Sun, K.-W., Nemec, A. A., Murphy, D. L., Cong, X., Northrup, V., Zelterman, D., and Sweasy, J. B. (2012b) Human POLB gene is mutated in high percentage of colorectal tumors, *J. Biol. Chem.* 287, 23830-23839.

Donley, N., Jaruga, P., Coskun, E., Dizdaroglu, M., McCullough, A. K., and Lloyd, R. S. (2015) Small molecule inhibitors of 8-oxoguanine DNA glycosylase-1 (OGG1), *ACS Chem. Biol.* 10, 2334-2343.

Dorjsuren, D., Kim, D., Vyjayanti, V. N., Maloney, D. J., Jadhav, A., Wilson, D. M., III, and Simeonov, A. (2012) Diverse small molecule inhibitors of human apurinic/apyrimidinic endonuclease APE1 identified from a screen of a large public collection, *PLoS One* 7, e47974.

Dorjsuren, D., Wilson, D. M., Beard, W. A., McDonald, J. P., Austin, C. P., Woodgate, R., Wilson, S. H., and Simeonov, A. (2009) A real-time fluorescence method for enzymatic characterization of specialized human DNA polymerases, *Nucleic Acids Res.* 37, e128-e128.

Feng, J.-A.; Crasto, C. J.; Matsumoto, Y. (1998) *Biochemistry*, 37, 9605-9611.

Friedberg, E. C.; Walker, G., C.; Siede, W.; Wood, R. D.; Schultz, R. A.; Ellenberger, T. *DNA Repair and Mutagenesis;* 2nd ed.; ASM Press: Washington, D.C., 2006.

Fu, D., Calvo, J. A., and Samson, L. D. (2012) Balancing repair and tolerance of DNA damage caused by alkylating agents, *Nat. Rev. Cancer* 12, 104-120.

Gao, Z., Maloney, D. J., Dedkova, L. M., and Hecht, S. M. (2008) Inhibitors of DNA polymerase beta: Activity and mechanism, *Bioorg. & Med. Chem.* 16, 4331-4340.

Garcia-Diaz, M., Bebenek, K., Kunkel, T. A., and Blanco, L. (2001) Identification of an intrinsic 5'-deoxyribose-5-phosphate lyase activity in human DNA polymerase λ, *J. Biol. Chem.* 276, 34659-34663.

Gavande, N. S., VanderVere-Carozza, P. S., Hinshaw, H. D., Jalal, S. I., Sears, C. R., Pawelczak, K. S., and Turchi, J. J. (2016) DNA repair targeted therapy: The past or future of cancer treatment?, *Pharmacol. Ther.* 160, 65-83.

Gates, K. S., Nooner, T., and Dutta, S. (2004) Biologically relevant chemical reactions of N7-alkylguanine residues in DNA, *Chem. Res. Toxicol.* 17, 839-856.

Goellner, E. M., Svilar, D., Almeida, K. H., and Sobol, R. W. (2012) Targeting DNA polymerase β for therapeutic intervention, *Curr. Mol. Pharmacol.* 5, 68-87.

Goldberg, I. H. (1991)*Acc. Chem. Res.,* 24, 191-198.

Gowda, A. S. P., Suo, Z., and Spratt, T. E. (2017) Honokiol inhibits DNA polymerases β and λ and increases bleomycin sensitivity of human cancer cells, *Chem. Res. Toxicol.* 30, 715-725.

Guan, L., and Greenberg, M. M. (2010) Irreversible inhibition of DNA polymerase β by an oxidized abasic lesion, *J. Am. Chem. Soc.* 132, 5004-5005.

Guan, L., Bebenek, K., Kunkel, T. A., and Greenberg, M. M. (2010) Inhibition of short Patch and long patch base excision repair by an oxidized abasic site, *Biochemistry* 49, 9904-9910.

Helleday, T., Petermann, E., Lundin, C., Hodgson, B., and Sharma, R. A. (2008) DNA repair pathways as targets for cancer therapy, *Nat. Rev. Cancer* 8, 193-204.

Hong, I. S., and Greenberg, M. M. (2004) Mild generation of 5-(2'-deoxyuridinyl)methyl radical from a phenyl selenide precursor, *Org. Lett.* 6, 5011-5013.

Horton, J. K., Baker, A., VandeBerg, B. J., Sobol, R. W., and Wilson, S. H. (2002) Involvement of DNA polymerase β in protection against the cytotoxicity of oxidative DNA damage, *DNA Repair* 1, 317-333.

Horton, J. K., Joyce-Gray, D. F., Pachkowski, B. F., Swenberg, J. A., and Wilson, S. H. (2003) Hypersensitivity of DNA polymerase β null mouse fibroblasts reflects accumulation of cytotoxic repair intermediates from site-specific alkyl DNA lesions, *DNA Repair* 2, 27-48.

Horton, J. K.; Watson, M.; Stefanick, D. F.; Shaughnessy, D. T.; Taylor, J. A.; Wilson, S. H. (2008) *Cell Res.,* 18, 48-63.

Husain, I.; Arteaga, C. L.; Srivastava, D. K.; Wilson, S. H. (1999) *Carcinogenesis,* 20, 1049-1054.

Ide, H., Akamatsu, K., Kimura, Y., Michiue, K., Makino, K., Asaeda, A., Takamori, Y., and Kubo, K. (1993) Synthesis and damage specificity of a novel probe for the detection of abasic sites in DNA, *Biochemistry* 32, 8276-8283.

Jacobs, A. C., Kreller, C. R., and Greenberg, M. M. (2011) Long patch base excision repair compensates for DNA Polymerase β inactivation by the C4'-oxidized abasic site, *Biochemistry* 50, 136-143.

Jessen, H. J.; Schulz, T.; Balzarini, J.; Meier, C. (2008) *Angew. Chem. Int. Ed.,* 47, 8719-8722.

Jiang, Y. L.; Krosky, D. J.; Seiple, L.; Stivers, J. T. (2005) *J. Am. Chem. Soc.,* 127, 17412-17420.

Kodama, T.; Greenberg, M. M. (2005) *J. Org. Chem.,* 70, 9916-9924.

Kozarich, J. W., Worth, L., Frank, B. L., Christner, D. F., Vanderwall, D. E., and Stubbe, J. (1989) Sequence-specific isotope effects on the cleavage of DNA by bleomycin, *Science* 245, 1396-1399.

Kuriyama, I.; Miyazaki, A.; Tsuda, Y.; Yoshida, H.; Mizushina, Y. (2013) *Bioorg. & Med. Chem.,* 21, 403-411.

Kwarcinski, F. E.; Fox, C. C.; Steffey, M. E.; Soellner, M. B. (2012) *ACS Chemical Biology,* 7, 1910-1917.

Lavrik, O. I., Kolpashchikov, D. M., Prasad, R., Sobol, R. W., and Wilson, S. H. (2002) Binary system for selective photoaffinity labeling of base excision repair DNA polymerases, *Nucleic Acids Res.* 30, e73.

Lindahl, T. in Progress in *Nucleic Acid Research* and Molecular Biology, Vol. 68 (Ed.: K. Moldave), Academic Press, San Diego, 2001, pp. xvii.

Liu, Q.; Sabnis, Y.; Zhao, Z.; Zhang, T.; Buhrlage, S. J.; Jones, L. H.; Gray, N. S. (2013) *Chemistry & Biology,* 20, 146-159.

Liu, J.; Wong, C.-H. (2002) *Tetrahedron Lett.,* 43, 4037-4039.

Liu, S., Lai, Y., Zhao, W., Wu, M., and Zhang, Z. (2011) Links between DNA polymerase beta expression and sensitivity to bleomycin, *Toxicology* 281, 63-69. Matsumoto, Y.; Kim, K. (1995) *Science,* 269, 699-702.

Matsumoto, Y.; Kim, K.; Katz, D. S.; Feng, J.-A. (1998) *Biochemistry,* 37, 6456-6464.

McGall, G. H., Rabow, L. E., Ashley, G. W., Wu, S. H., Kozarich, J. W., and Stubbe, J. (1992) New insight into the mechanism of base propenal formation during bleomycin mediated DNA degradation, *J. Am. Chem Soc.* 114, 4958-4967.

Mootoo, D. R.; Date, V.; Fraser-Reid, B. (1988) *J. Am. Chem. Soc.,* 110, 2662-2663.

Nakamura, R.; Takeuchi, R.; Kuramochi, K.; Mizushina, Y.; Ishimaru, C.; Takakusagi, Y.; Takemura, M.; Kobayashi, S.; Yoshida, H.; Sugawara, F.; Sakaguchi, K. (2007) *Org. & Biomol. Chem.,* 5, 3912-3921.

Neef, A. B., and Luedtke, N. W. (2014) An azide-modified nucleoside for metabolic labeling of DNA, *ChemBioChem* 15, 789-793.

Nemec, A. A.; Donigan, K. A.; Murphy, D. L.; Jaeger, J.; Sweasy, J. B. (2012) *J. Biol. Chem.,* 287, 23840-23849.

Ora, M.; Taherpour, S.; Linna, R.; Leisvuori, A.; Hietamiki, E.; Poijirvi-Virta, P.; Beigelman, L.; Lonnberg, H. (2009) *J. Org. Chem.,* 74, 4992-5001.

Pascucci, B.; Maga, G.; Hilbscher, U.; Bjoras, M.; Seeberg, E.; Hickson, I. D.; Villani, G.; Giordano, C.; Cellai, L.; Dogliotti, E. (2002) *Nucleic Acids Res.,* 30, 2124.

Pitié, M., and Pratviel, G. (2010) Activation of DNA carbon, hydrogen bonds by metal complexes, *Chem. Rev.* 110, 1018-1059.

Polosina, Y. Y.; Rosenquist, T. A.; Grollman, A. P.; Miller, H. (2004) *DNA Repair,* 3, 1469-1474.

Pourceau, G., Meyer, A., Vasseur, J.-J., and Morvan, F. (2009) Azide solid support for 3'-conjugation of oligonucleotides and their circularization by click chemistry, *J. Org. Chem.* 74, 6837-6842.

Prasad, R.; Batra, V. K.; Yang, X. P.; Krahn, J. M.; Pedersen, L. C.; Beard, W. A.; Wilson, S. H. (2005) *DNA Repair,* 4, 1347-1357.

Prasad, R.; Beard, W. A.; Chyan, J. Y.; Maciejewski, M. W.; Mullen, G. P.; Wilson, S. H. (1998) *J. Biol. Chem.,* 273, 11121-11126.

Prasad, R.; Beard, W. A.; Strauss, P. S.; Wilson, S. H. (1998) *J. Biol. Chem.,* 273, 15263-15270.

Rabow, L. E., Stubbe, J., and Kozarich, J. W. (1990) Identification and quantitation of the lesion accompanying base release in bleomycin-mediated DNA degradation, *J. Am. Chem. Soc.* 112, 3196-3203.

Rai, G., Vyjayanti, V. N., Dorjsuren, D., Simeonov, A., Jadhav, A., Wilson, D. M., and Maloney, D. J. (2012)

Synthesis, biological evaluation, and structure-activity relationships of a novel class of apurinic/apyrimidinic endonuclease 1 inhibitors, *J. Med. Chem.* 55, 3101-3112.

Schermerhorn, K. M., and Delaney, S. (2014) A chemical and kinetic perspective on base excision repair of DNA, *Acc. Chem. Res.* 47, 1238-1246.

Silverman, R. B. The Organic Chemistry of Enzyme-Catalyzed Reactions; Academic Press: San Diego, 2000.

Singh, J.; Petter, R. C.; Baillie, T. A.; Whitty, A. (2011) *Nat. Rev. Drug Discov.,* 10, 307-317.

Sobol, R. W.; Horton, J. K.; Kuhn, R.; Gu, H.; Singhal, R. K.; Prasad, R.; Rajewsky, K.; Wilson, S. H. (1996) *Nature,* 379, 183.

Sobol, R. W., Prasad, R., Evenski, A., Baker, A., Yang, X. P., Horton, J. K., and Wilson, S. H. (2000) The lyase activity of the DNA repair protein β-polymerase protects from DNA damage-induced cytotoxicity, *Nature* 405, 807-810.

Sobol, R. W., Kartalou, M., Almeida, K. H., Joyce, D. F., Engelward, B. P., Horton, J. K., Prasad, R., Samson, L. D., and Wilson, S. H. (2003) Base excision repair intermediates induce p53-independent cytotoxic and genotoxic responses, *J. Biol. Chem.* 278, 39951-39959.

Starcevic, D.; Dalal, S.; Sweasy, J. B. (2004) *Cell Cycle,* 3, 998-1001.

Stevens, A. J., Guan, L., Bebenek, K., Kunkel, T. A., and Greenberg, M. M. (2013) DNA polymerase λ inactivation by oxidized abasic sites, *Biochemistry* 52, 975-983.

Stivers, J. T.; Jiang, Y. L. (2003) *Chem. Rev.,* 103, 2729-2759.

Strittmatter, T., Bareth, B., Immel, T. A., Huhn, T., Mayer, T. U., and Marx, A. (2011) Small molecule inhibitors of human DNA polymerase β, *ACS Chem. Biol.* 6, 314-319.

Strittmatter, T.; Brockmann, A.; Pott, M.; Hantusch, A.; Brunner, T.; Marx, A. (2013) *ACS Chem. Biol.,* doi: 10.1021/cb4007562.

Sugiyama, H., Kawabata, H., Fujiwara, T., Dannoue, Y., and Saito, I. (1990) Specific detection of C-4' hydroxylated abasic sites generated by bleomycin and neocarzinostatin in DNA, *J. Am. Chem. Soc.* 112, 5252-5257.

Trivedi, R. N., Wang, X.-h., Jelezcova, E., Goellner, E. M., Tang, J.-b., and Sobol, R. W. (2008) Human methyl purine DNA glycosylase and DNA polymerase β expression collectively predict sensitivity to temozolomide, *Mol. Pharmacol.* 74, 505-516.

Trivedi, R. N., Almeida, K. H., Fornsaglio, J. L., Schamus, S., and Sobol, R. W. (2005) The role of base excision repair in the sensitivity and resistance to temozolomide-mediated cell death, *Cancer Res.* 65, 6394-6400.

Wilson, S. H., Beard, W. A., Shock, D. D., Batra, V. K., Cavanaugh, N. A., Prasad, R., Hou, E. W., Liu, Y. A., Asagoshi, K., Horton, J. K., Stefanick, D. F., Kedar, P. S., Carrozza, M. J., Masaoka, A., and Heacock, M. L. (2010) Base excision repair and design of small molecule inhibitors of human DNA Polymerase β, *Cell. Mol. Life Sci.* 67, 3633-3647.

Wyatt, M. D., and Pittman, D. L. (2006) Methylating agents and DNA repair responses: methylated bases and sources of strand breaks, *Chem. Res. Toxicol.* 19, 1580-1594.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

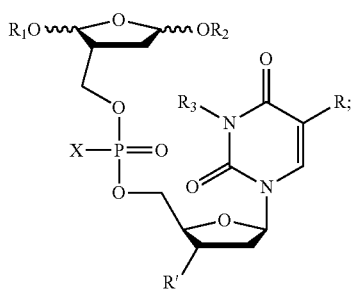

wherein:

X is selected from the group consisting of alkyl, alkoxyl, O$^-$, and S$^-$;

R is selected from the group consisting of —CH$_3$ and

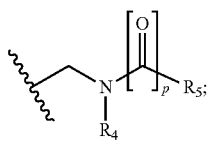

R' is selected from the group consisting of —NR$_6$R$_7$ and

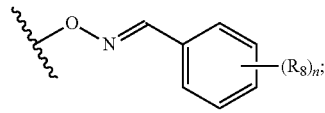

with the proviso that if R is —CH$_3$, then R' is —NR$_6$R$_7$;

R$_1$ and R$_2$ are each independently selected from the group consisting of hydrogen and —C(=O)-alkyl;

R$_3$ and R$_4$ are each independently selected from the group consisting of hydrogen or C$_1$-C$_6$ alkyl;

R$_5$, R$_6$ and R$_7$ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof;

each R$_8$ is independently selected from the group consisting of halogen, hydroxyl, alkyl, alkenyl, alkynyl, alkoxyl, sulfhydryl, sulfide, and carboxyl;

n is an integer selected from the group consisting of 0, 1, 2, 3, 4, and 5;

p is an integer selected from the group consisting of 0 and 1; and pharmaceutically acceptable salts thereof.

2. The compound of claim 1, wherein the compound of formula (I) is selected from the group consisting of:

(Ia)
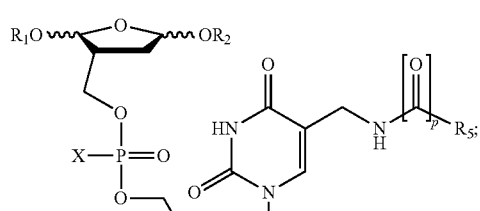
(Ib)
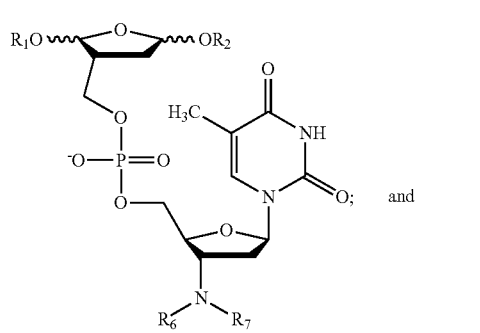
(Ic)
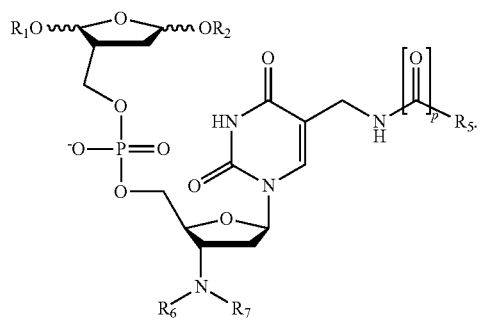
3. The compound of claim 1, wherein $R_5$ is selected from the group consisting of:
1016
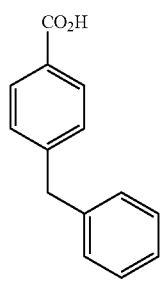
1017
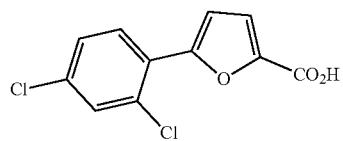
1018
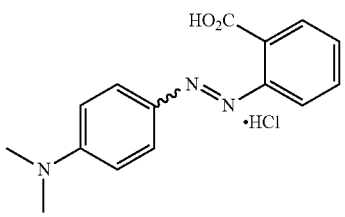
1019
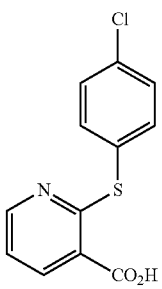
1020
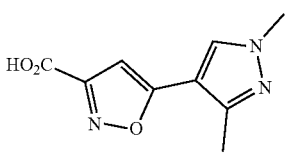
1021
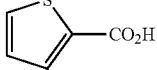
1022
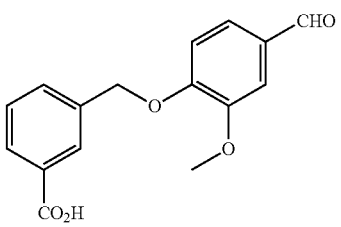
1023
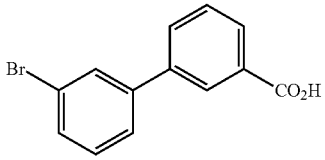
1024
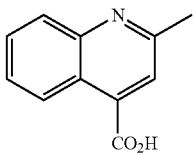
1025
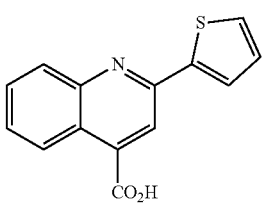

| | |
|---|---|
| 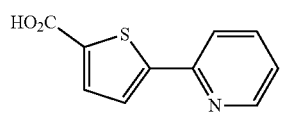 | 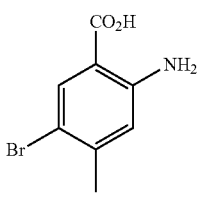 1034 |
| 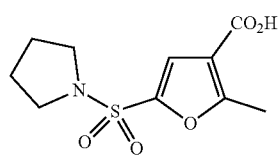 | 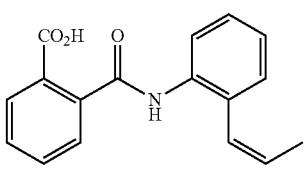 1035 |
| 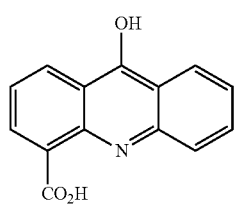 | 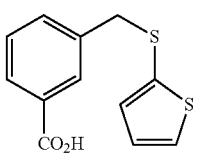 1036 |
| 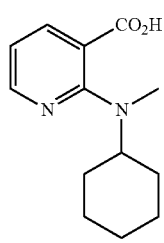 | 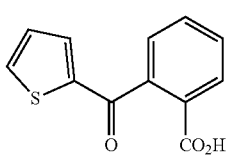 1037 |
| 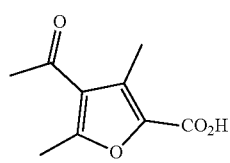 | 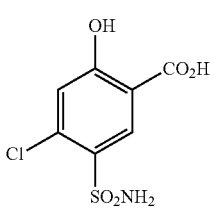 1038 |
| 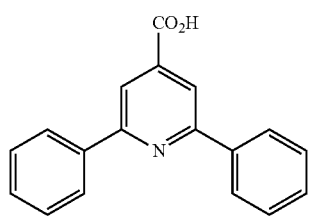 | 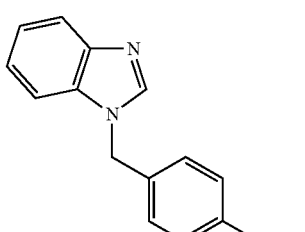 1039 |
| 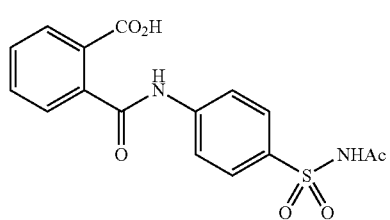 | 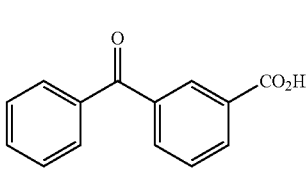 1040 |
| 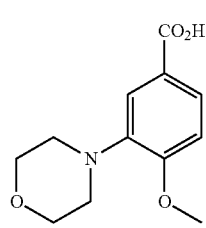 | 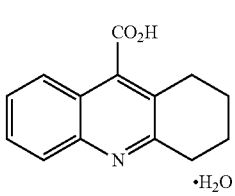 1041 |

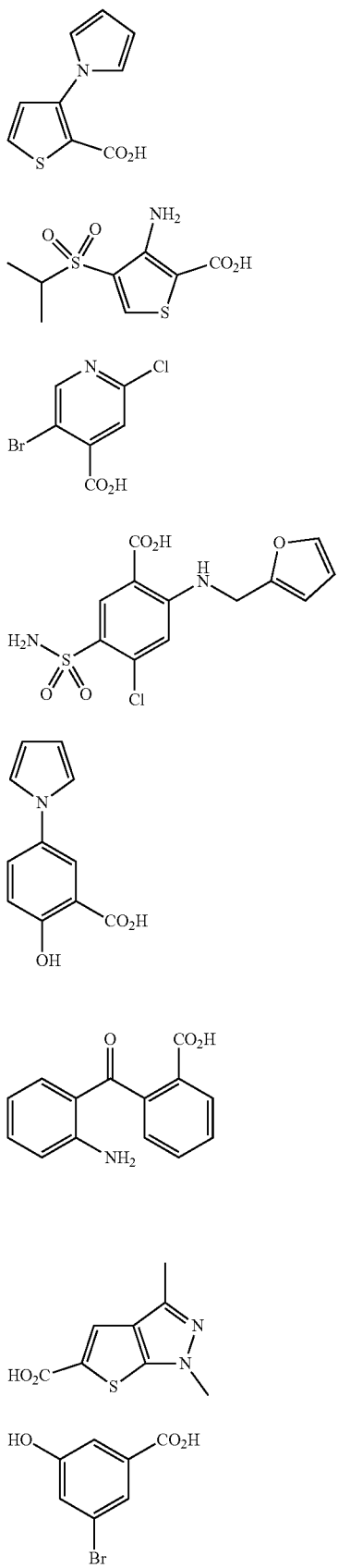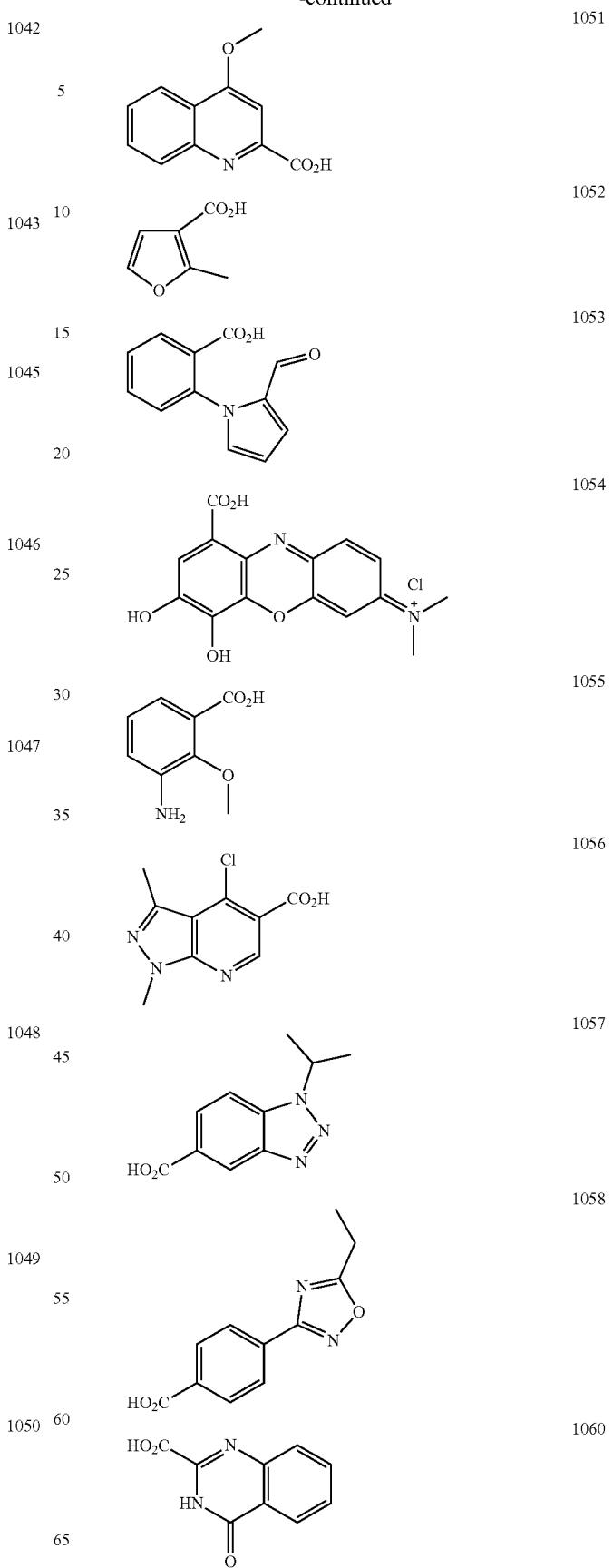

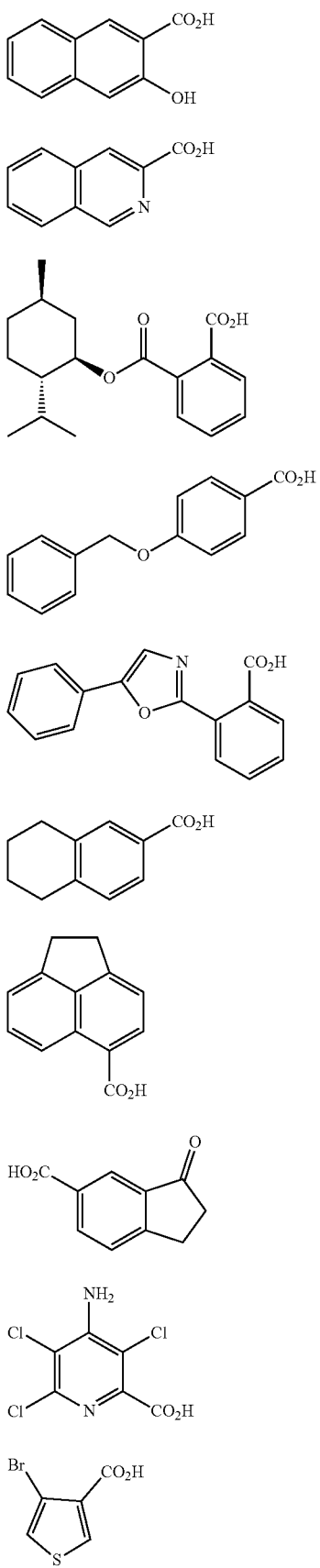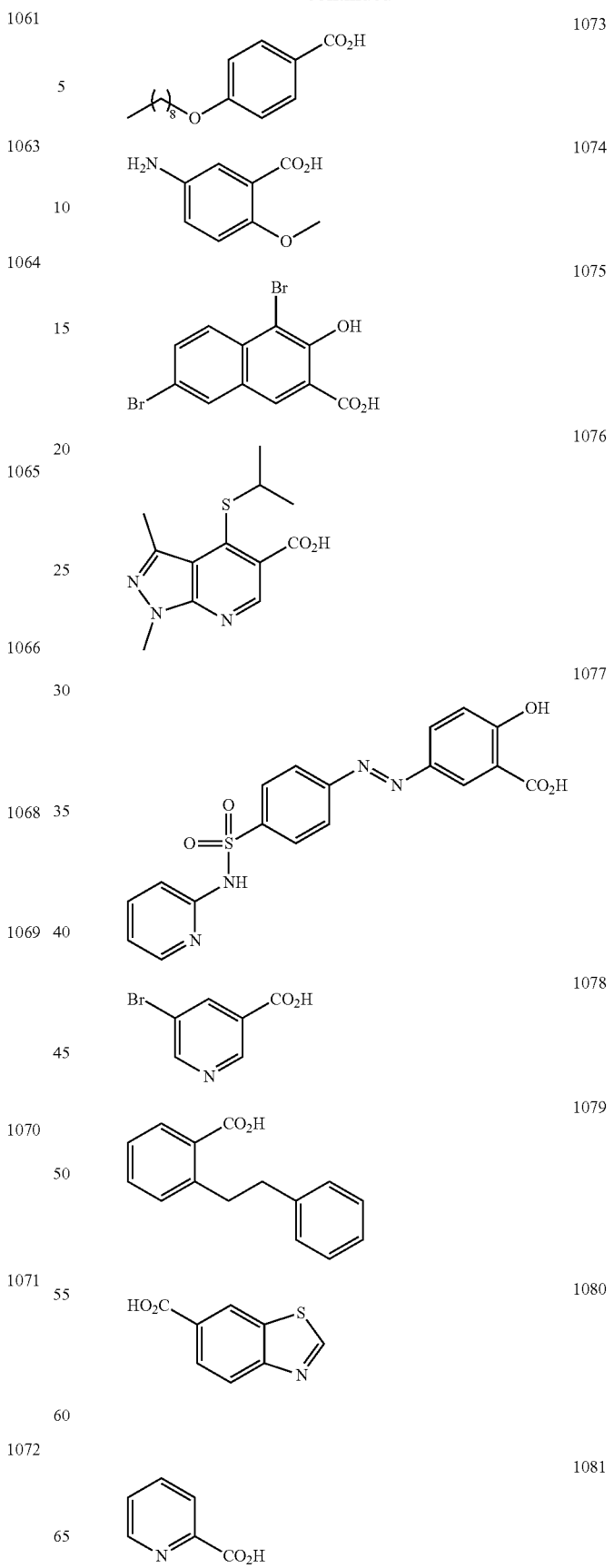

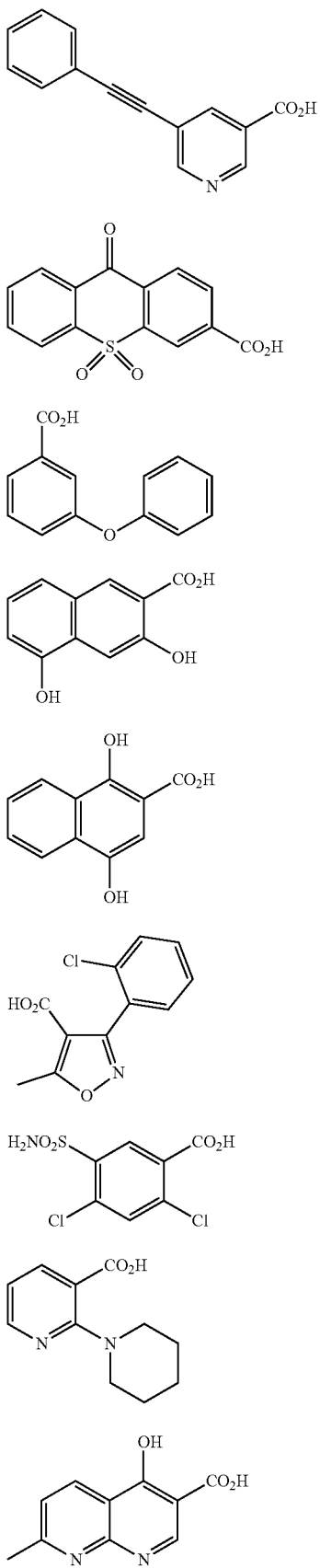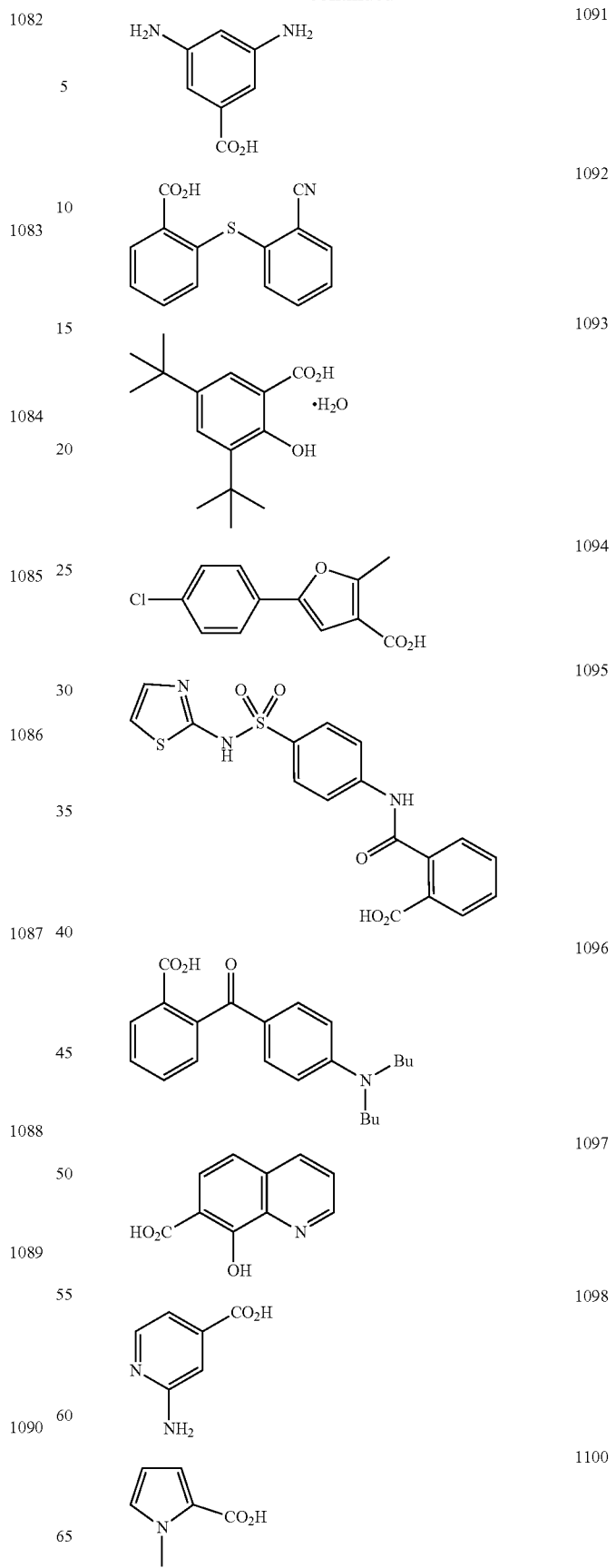

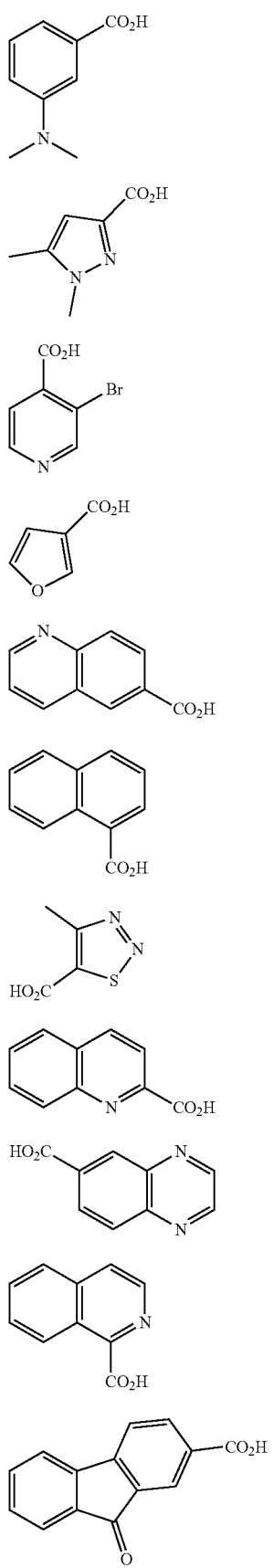
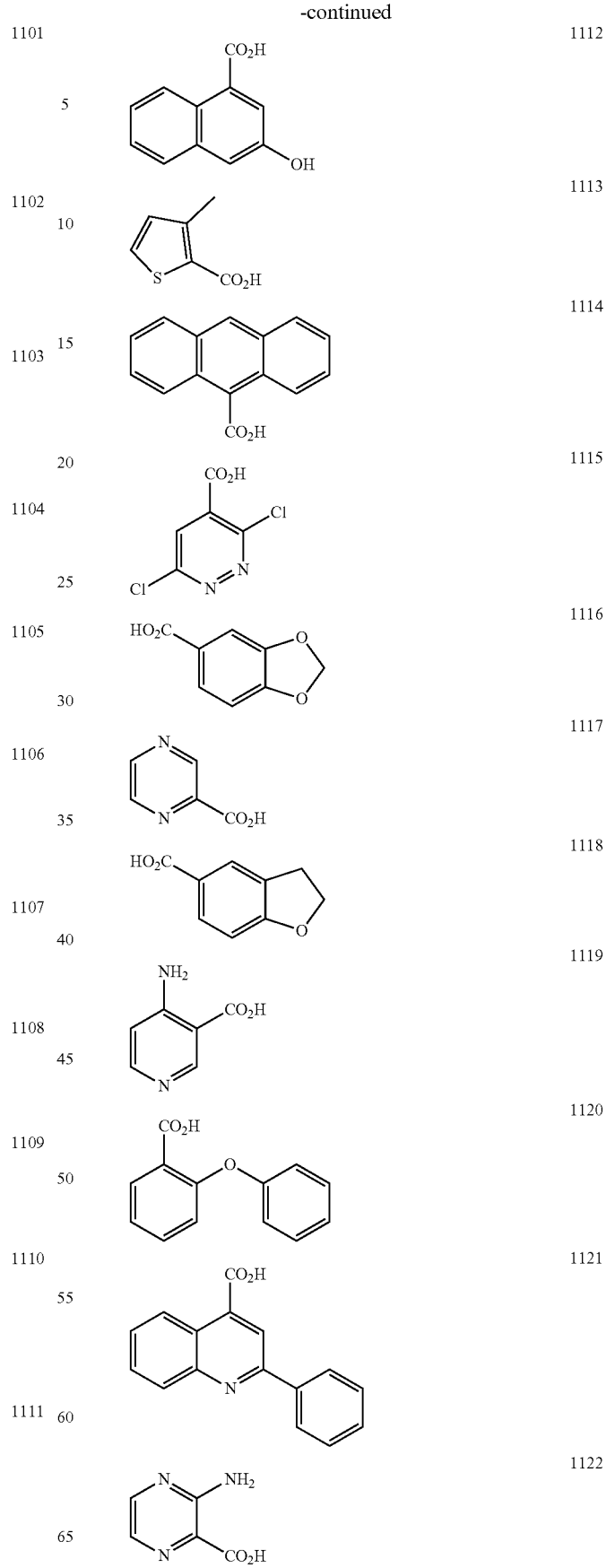

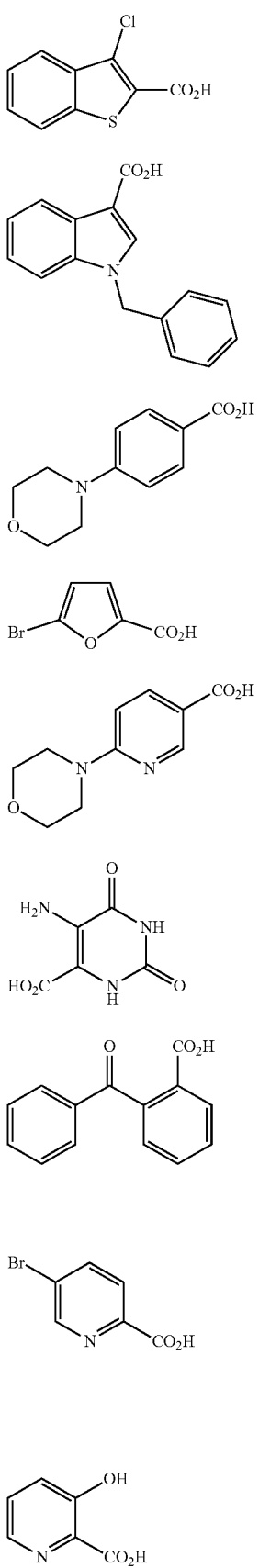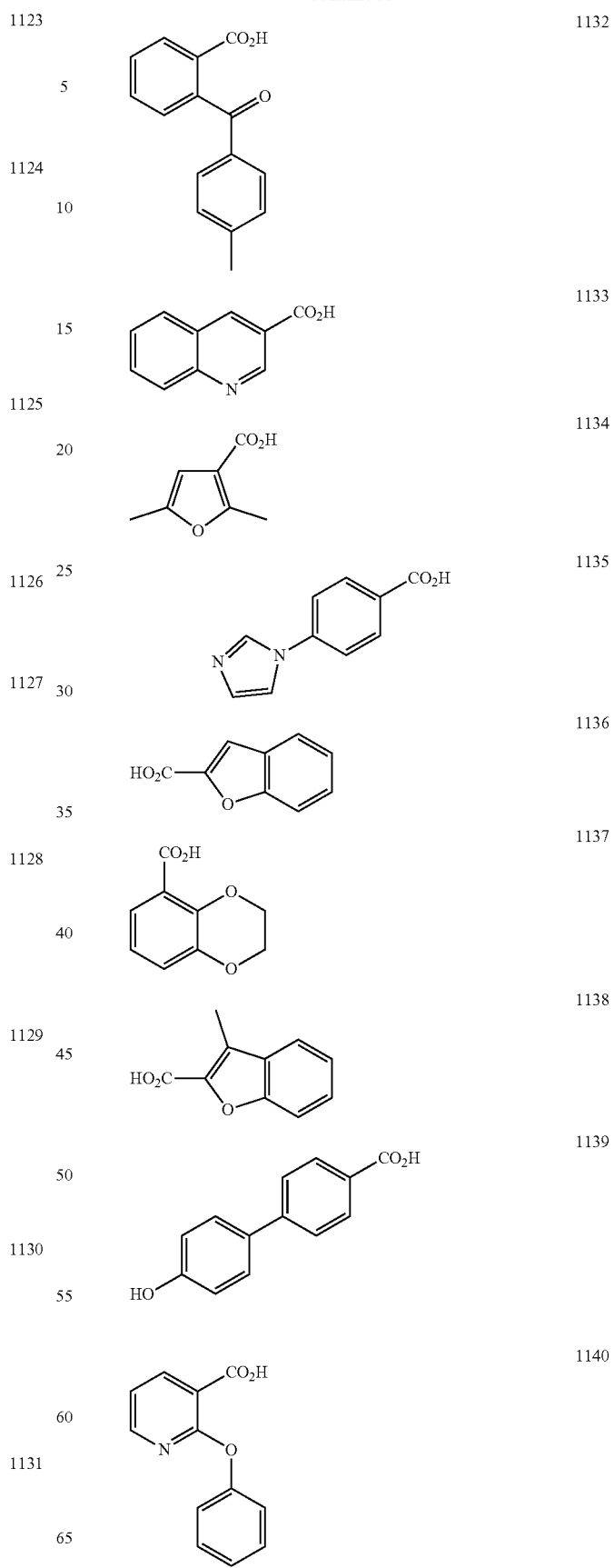

-continued
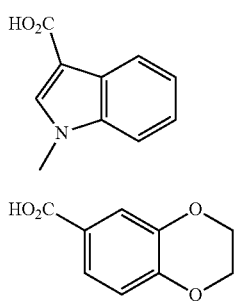
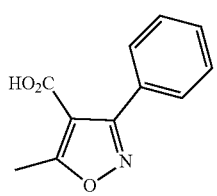
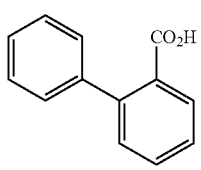
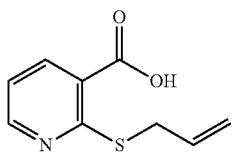
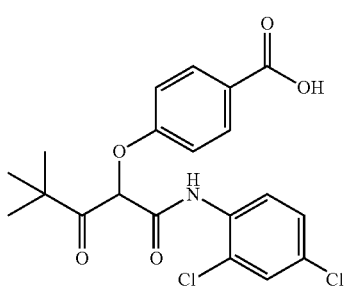
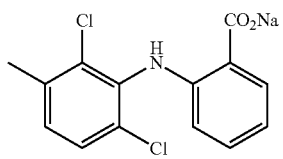
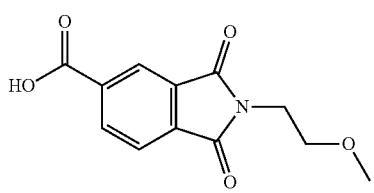
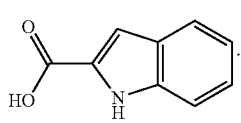
and
4. The compound of claim 1, wherein the compound of formula (I) is selected from the group consisting of:
5. A method for irreversibly inhibiting a DNA repair enzyme that possesses lyase activity in a subject, the method comprising administering to the subject a therapeutically effective amount of a compound of Formula (I):

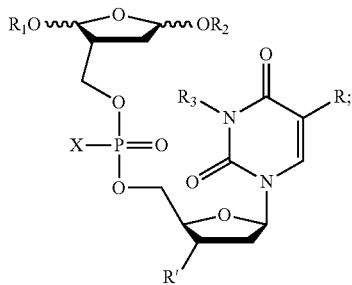

(I)

wherein:

X is selected from the group consisting of alkyl, alkoxyl, O⁻, and S⁻;

R is selected from the group consisting of —CH₃ and

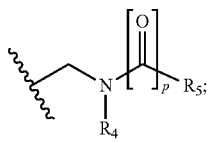

R' is selected from the group consisting of —NR₆R₇ and

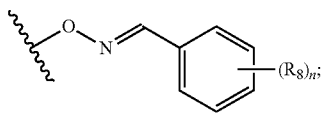

with the proviso that if R is —CH₃, then R' is —NR₆R₇;

R₁ and R₂ are each independently selected from the group consisting of hydrogen and —C(=O)-alkyl;

R₃ and R₄ are each independently selected from the group consisting of hydrogen or C₁-C₆ alkyl;

R₅, R₆ and R₇ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof;

each R₈ is independently selected from the group consisting of halogen, hydroxyl, alkyl, alkenyl, alkynyl, alkoxyl, sulfhydryl, sulfide, and carboxyl;

n is an integer selected from the group consisting of 0, 1, 2, 3, 4, and 5;

p is an integer selected from the group consisting of 0 and 1; and pharmaceutically acceptable salts thereof.

6. The method of claim 5, wherein the compound of formula (I) is selected from the group consisting of:

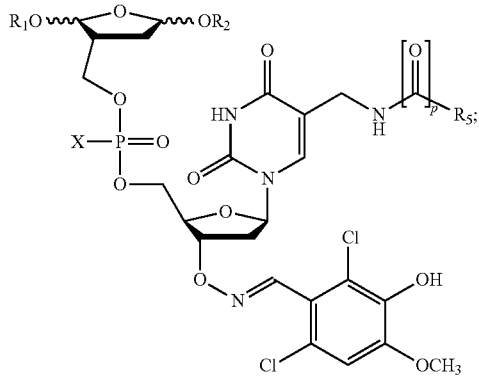

(Ia)

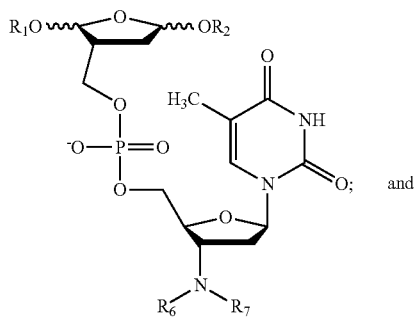

(Ib)

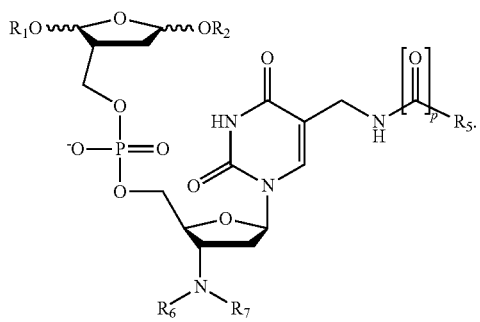

(Ic)

7. The method of claim 5, wherein R₅ is selected from the group consisting of:

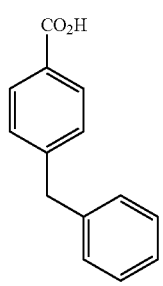

1016

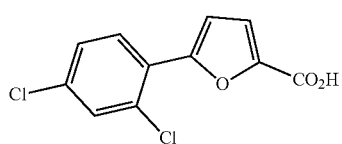

1017

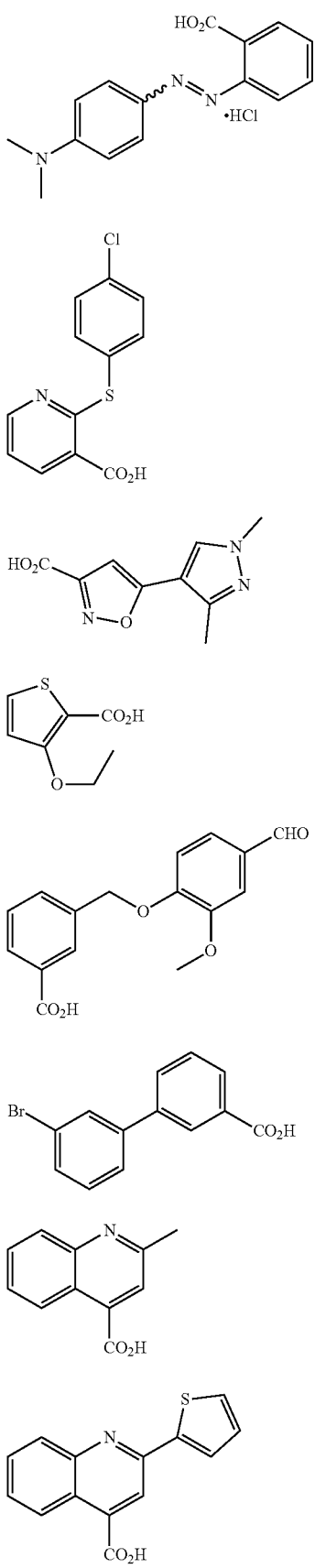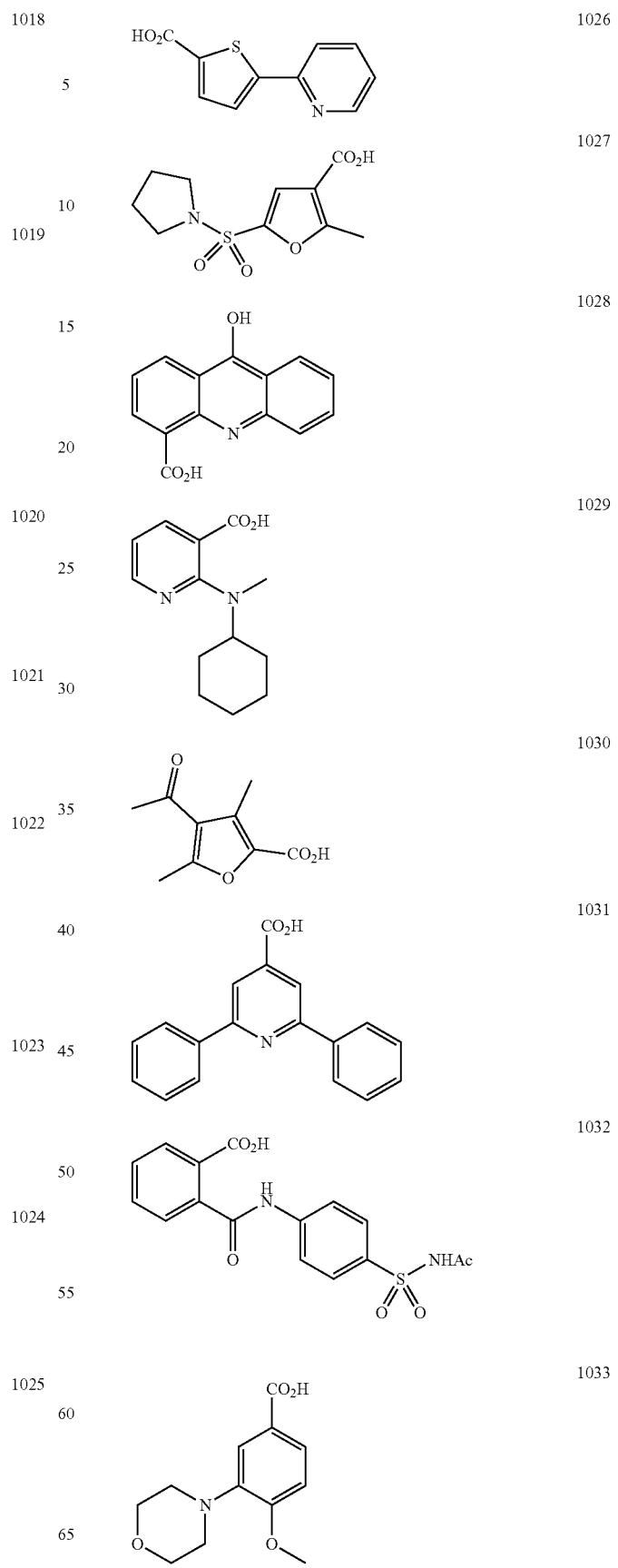

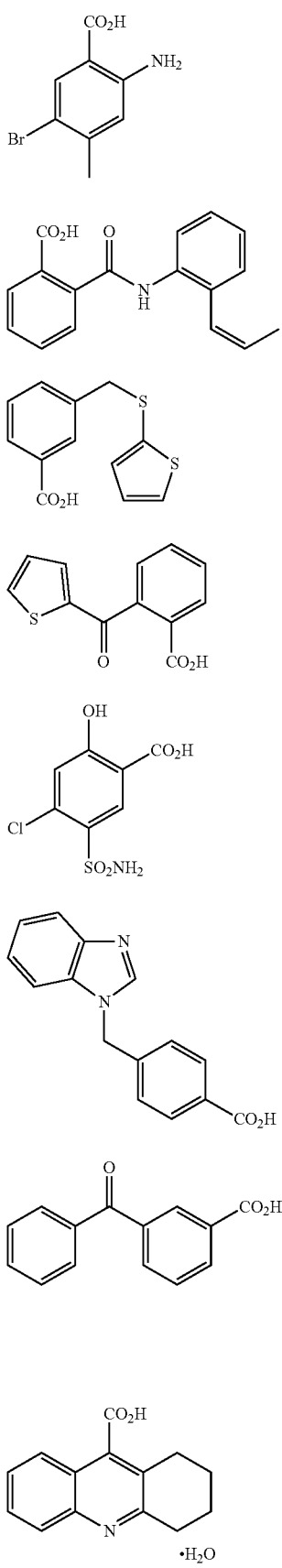
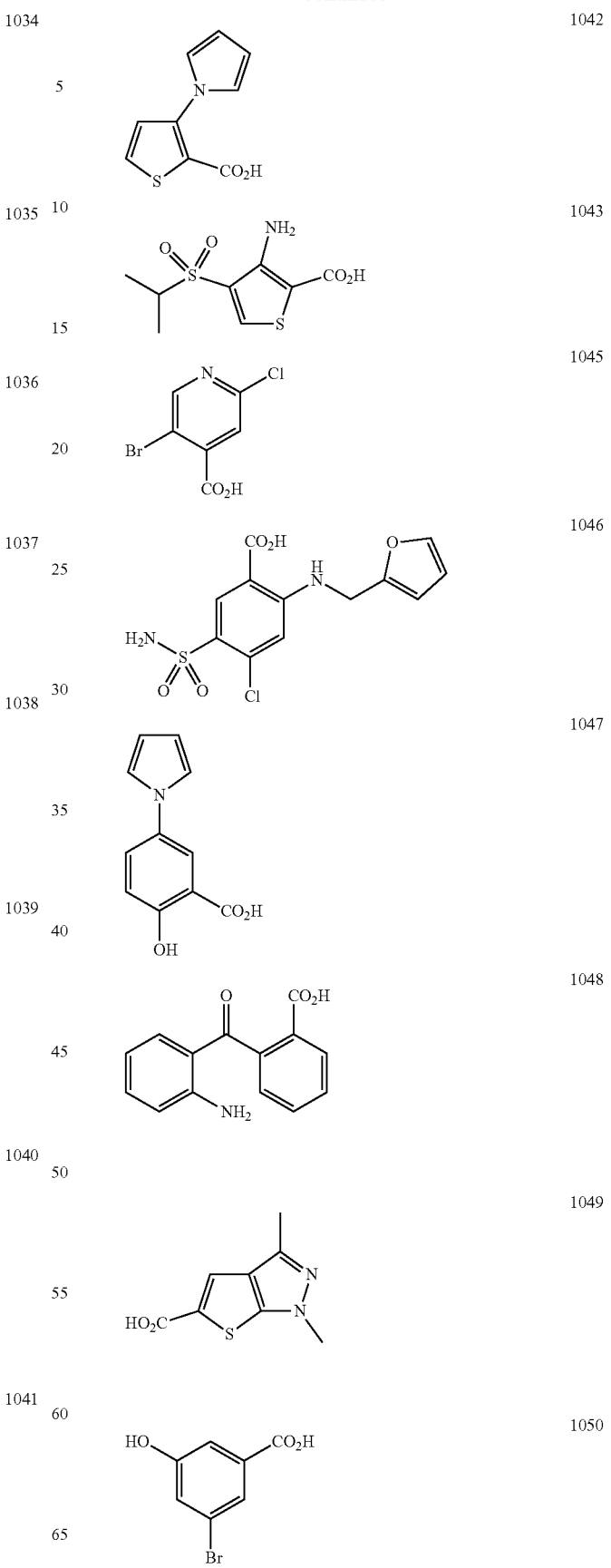

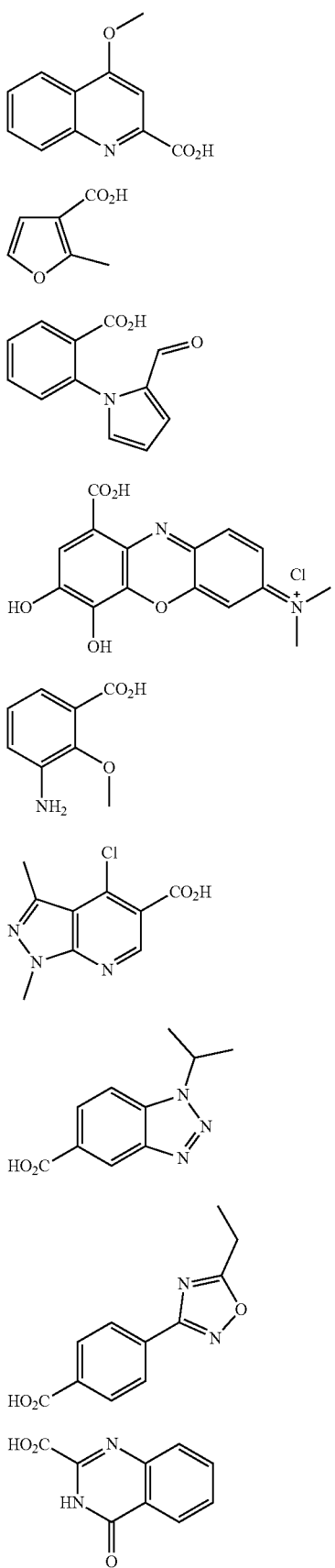
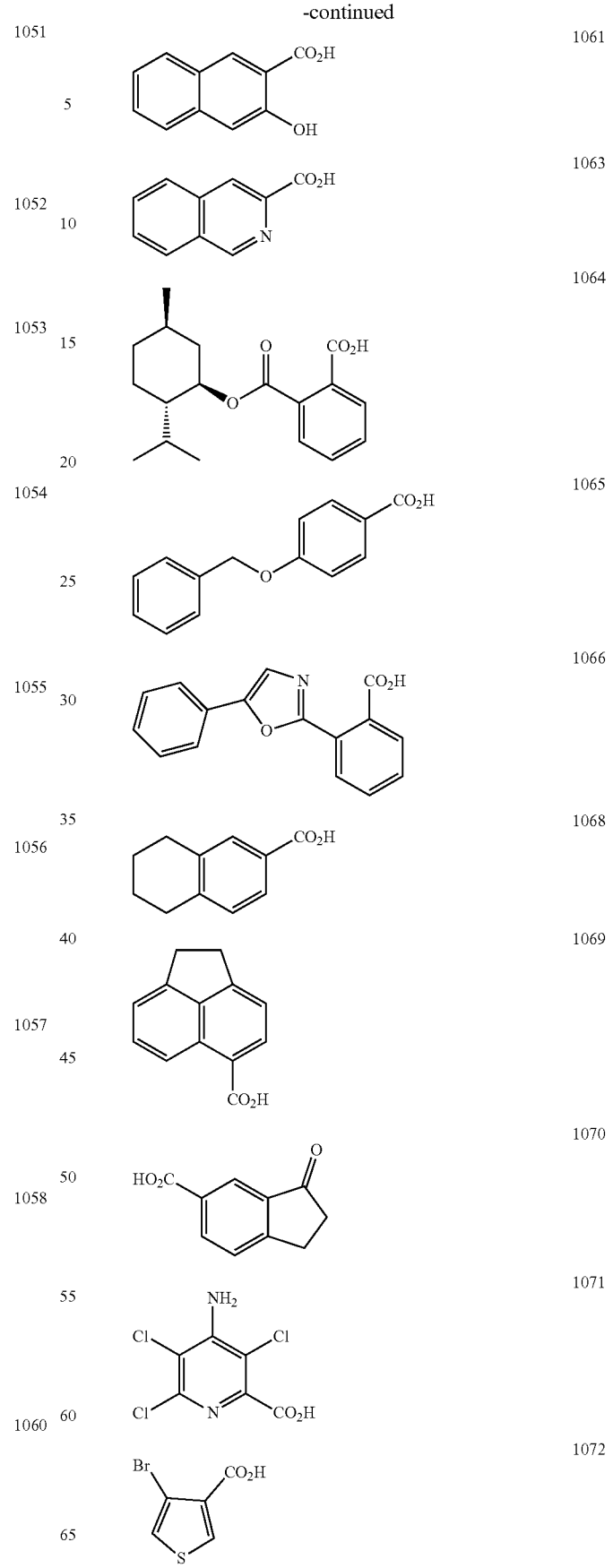

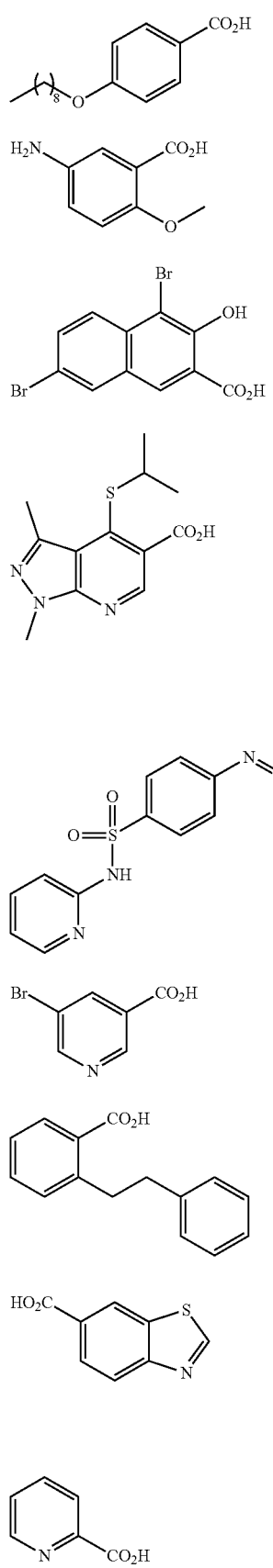
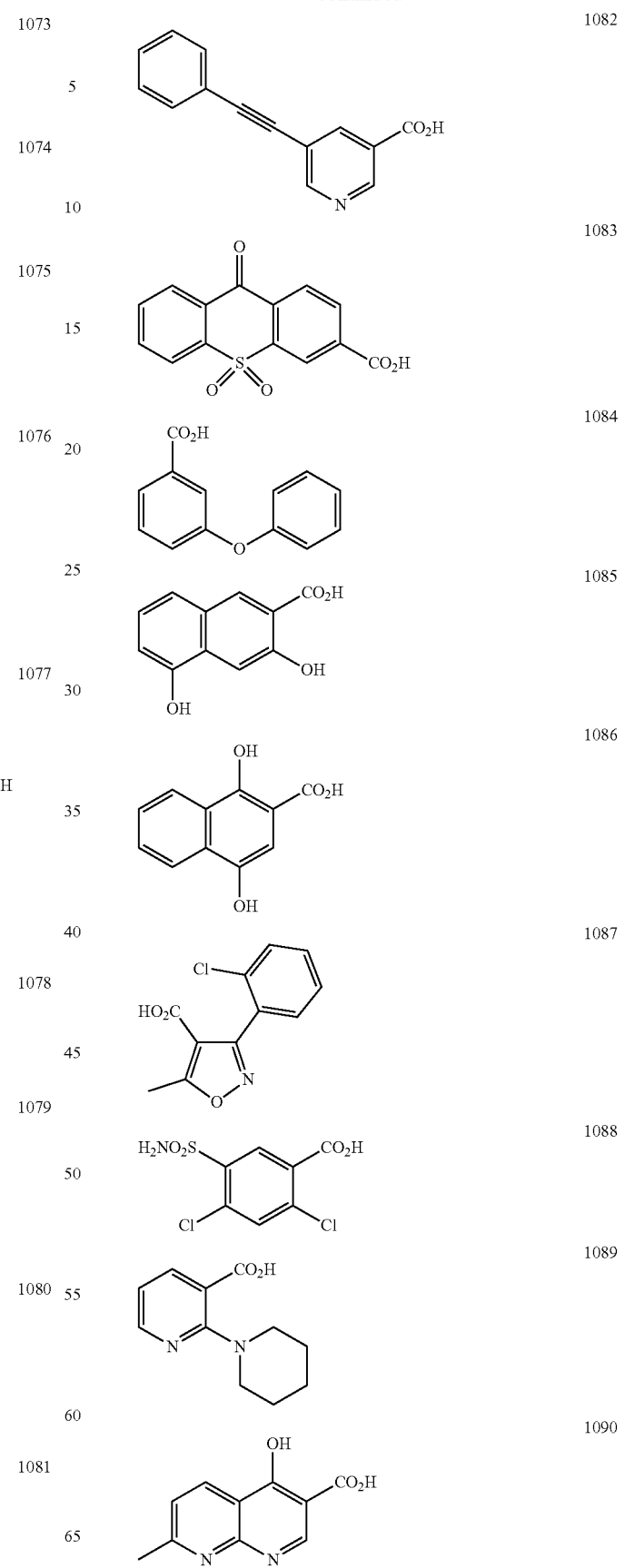

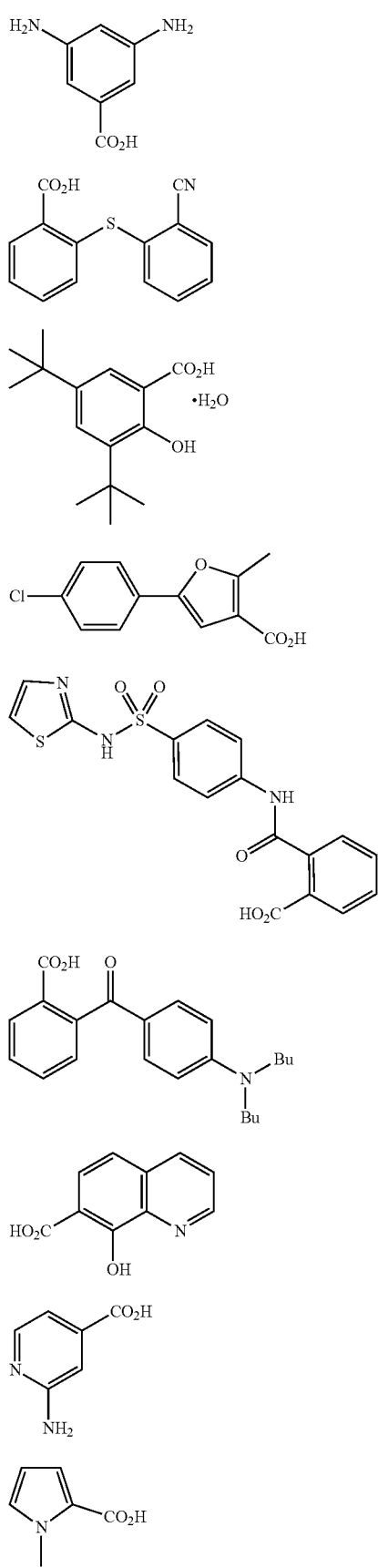
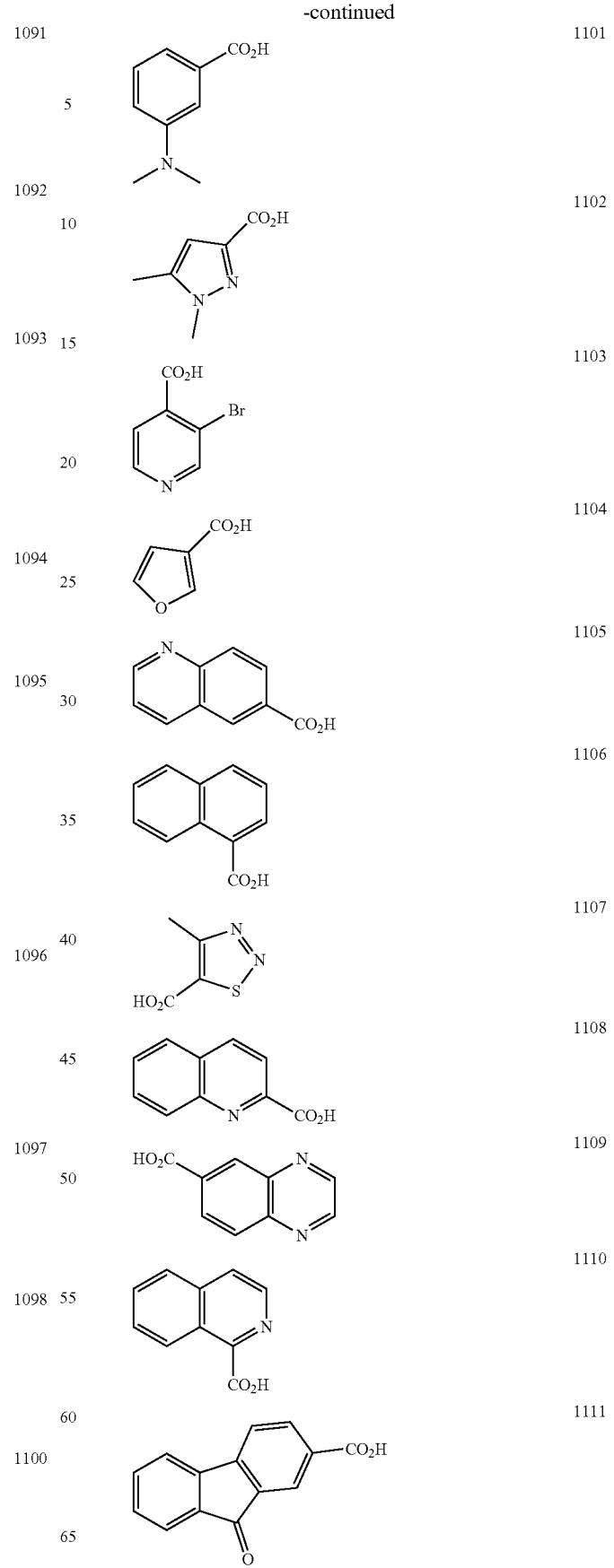

-continued
| | |
|---|---|
| 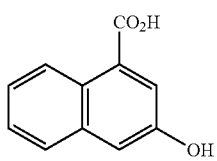 | 1112 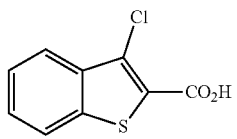 1123 |
| 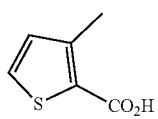 | 1113 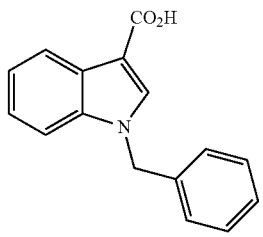 1124 |
| 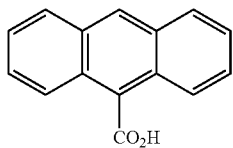 | 1114 |
| 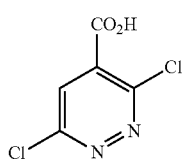 | 1115 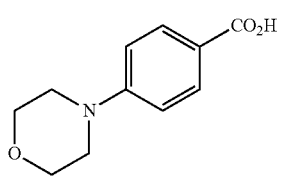 1125 |
| 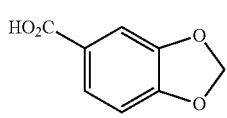 | 1116 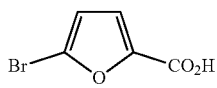 1126 |
| 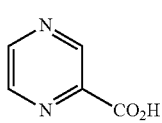 | 1117 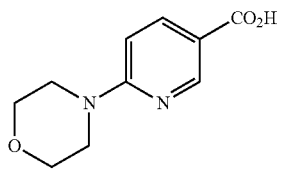 1127 |
| 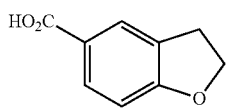 | 1118 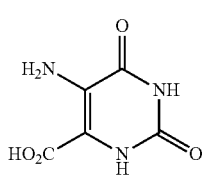 1128 |
| 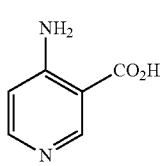 | 1119 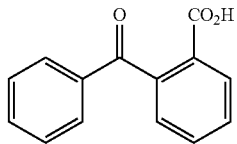 1129 |
| 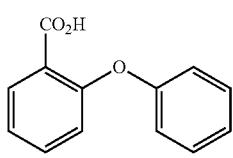 | 1120 |
| 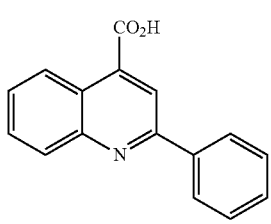 | 1121 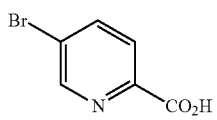 1130 |
| 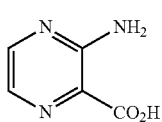 | 1122 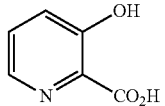 1131 |

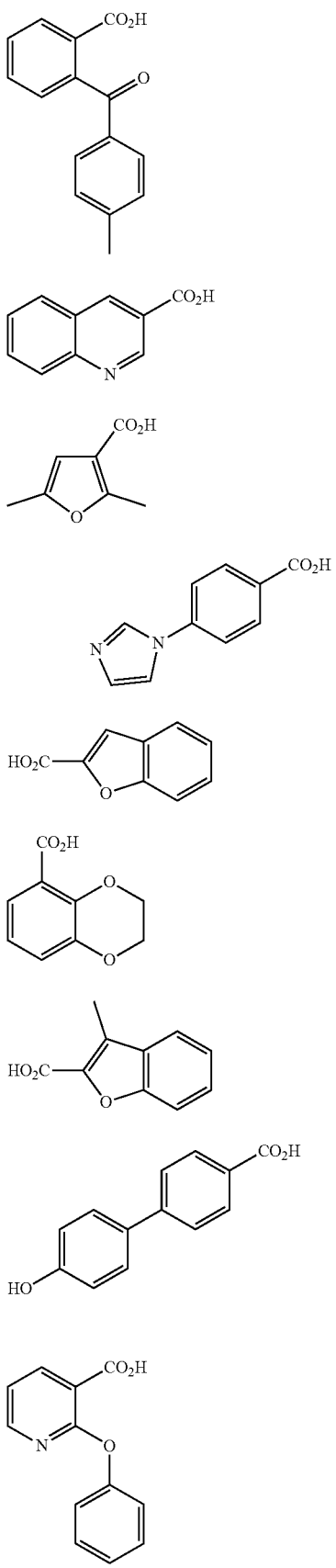
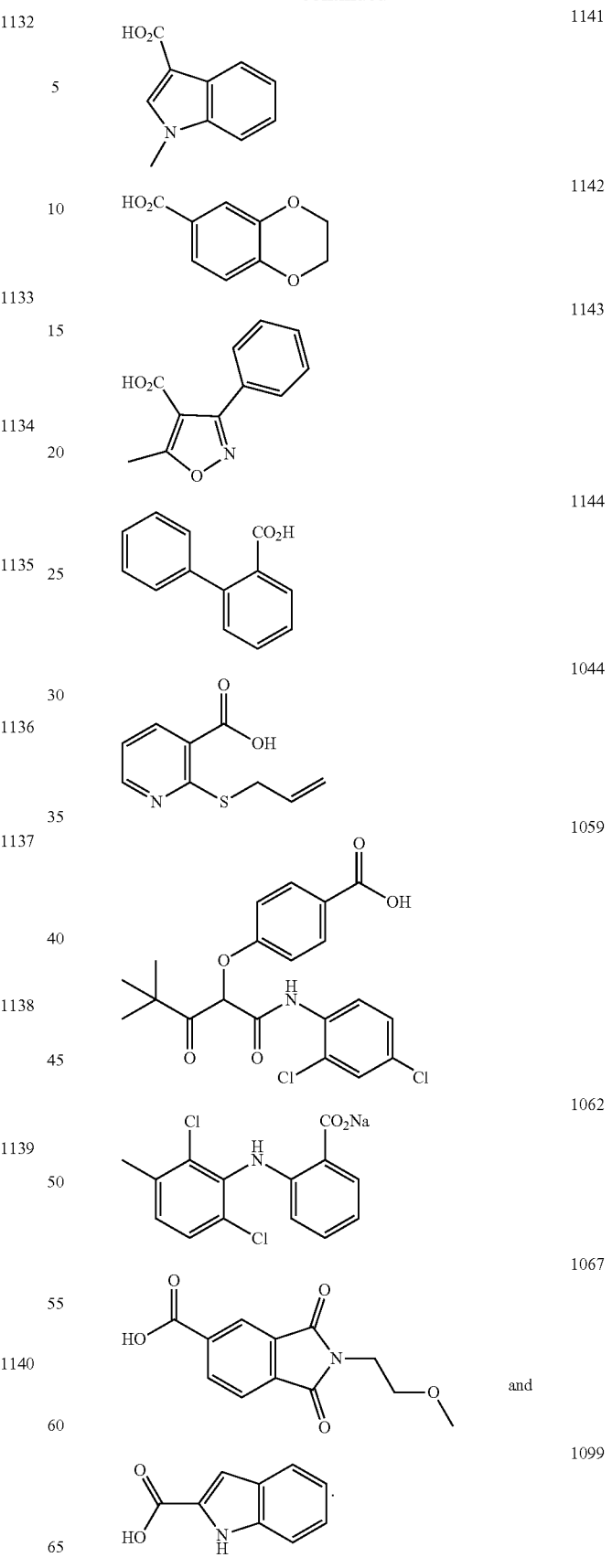

8. The method of claim 5, wherein the compound of formula (I) is selected from the group consisting of:

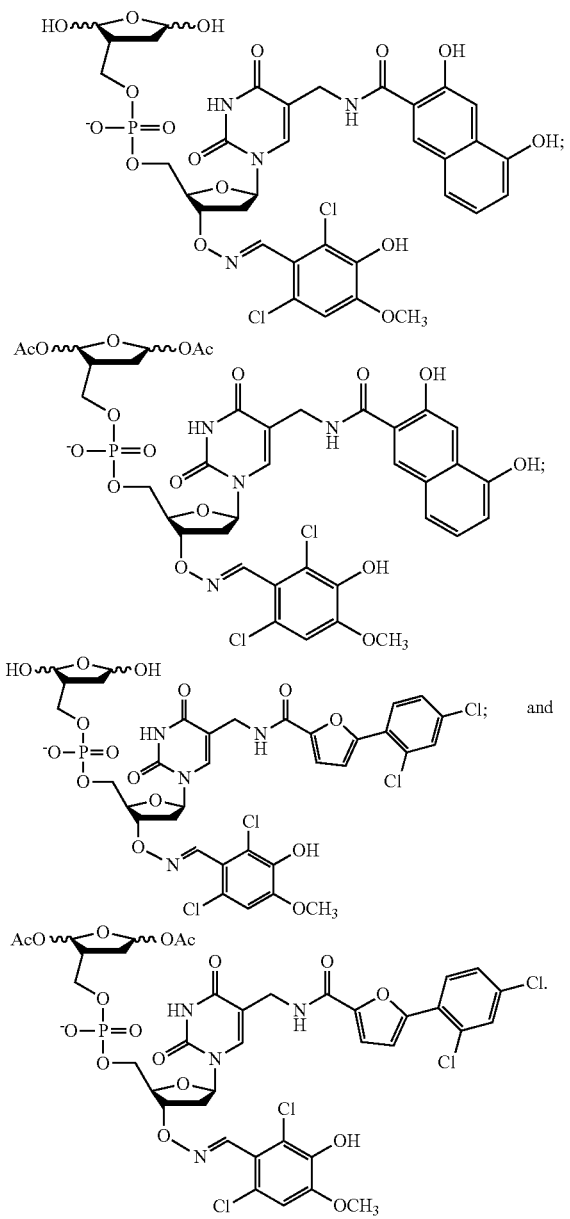

9. The method of claim 5, wherein the DNA repair enzyme is selected from the group consisting of DNA polymerase β, 5'-deoxyribose-5-phosphate lyase Ku70, and Endonuclease III-like protein 1.

10. The method of claim 5, wherein the compound inhibits the lyase activity of the DNA repair enzyme.

11. The method of claim 5, wherein the subject has cancer.

12. The method of claim 11, wherein inhibiting the DNA repair enzyme treats, inhibits, delays, or prevents the spread of the cancer in the subject.

13. The method of claim 12, further comprising treating, inhibiting, delaying, or preventing the spread of the cancer by inhibiting at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, and changes in the levels of an extracellular protease.

14. The method of claim 5, further comprising administering to the subject a DNA damaging agent.

15. The method of claim 14, wherein the DNA damaging agent is methyl methanesulfonate (MMS).

16. The method of claim 14, wherein the DNA damaging agent is administered before or simultaneously with administration of the compound of Formula (I).

17. A method for inhibiting a cancer cell, the method comprising contacting the cancer or noncancerous cell with a compound of Formula (I) in an amount effective to irreversibly inhibit a DNA repair enzyme that possesses lyase activity:

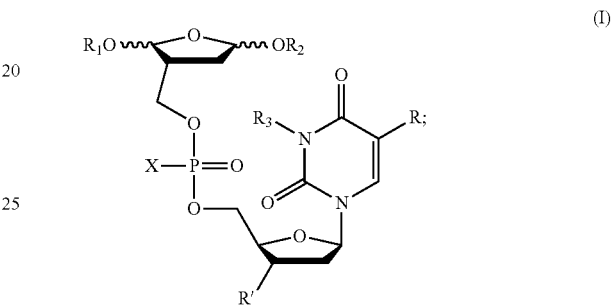

wherein:
X is selected from the group consisting of alkyl, alkoxyl, O⁻, and S⁻;
R is selected from the group consisting of —CH₃ and

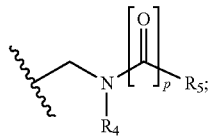

R' is selected from the group consisting of —NR₆R₇ and

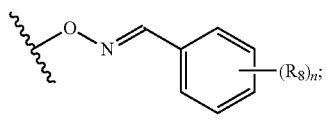

with the proviso that if R is —CH₃, then R' is —NR₆R₇;
R₁ and R₂ are each independently selected from the group consisting of hydrogen and —C(=O)-alkyl;
R₃ and R₄ are each independently selected from the group consisting of hydrogen or C₁-C₆ alkyl;
R₅, R₆ and R₇ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof;
each R₈ is independently selected from the group consisting of halogen, hydroxyl, alkyl, alkenyl, alkynyl, alkoxyl, sulfhydryl, sulfide, and carboxyl;
n is an integer selected from the group consisting of 0, 1, 2, 3, 4, and 5;

p is an integer selected from the group consisting of 0 and 1; and pharmaceutically acceptable salts thereof.

18. A method for irreversibly inhibiting a DNA repair enzyme that possesses lyase activity, the method comprising contacting the DNA repair enzyme with a compound of Formula (I) wherein contacting the DNA repair enzyme with the compound irreversibly inhibits the DNA repair enzyme:

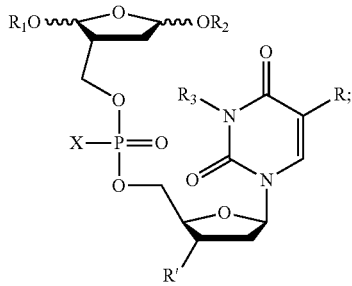
(I)

wherein:

X is selected from the group consisting of alkyl, alkoxyl, $O^-$, and $S^-$;

R is selected from the group consisting of —$CH_3$ and

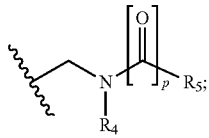

R' is selected from the group consisting of —$NR_6R_7$ and

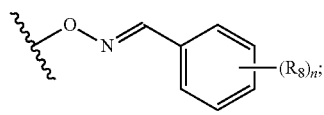

with the proviso that if R is —$CH_3$, then R' is —$NR_6R_7$;

$R_1$ and $R_2$ are each independently selected from the group consisting of hydrogen and —C(=O)-alkyl;

$R_3$ and $R_4$ are each independently selected from the group consisting of hydrogen or $C_1$-$C_6$ alkyl;

$R_5$, $R_6$ and $R_7$ are each independently selected from the group consisting of substituted or unsubstituted aryl, heteroaryl, arylalkyl, heteroarylalkyl, multicyclic aliphatic ring systems, multicylic aromatic ring systems, fused aliphatic ring systems, fused aromatic ring systems, and combinations thereof;

each $R_8$ is independently selected from the group consisting of halogen, hydroxyl, alkyl, alkenyl, alkynyl, alkoxyl, sulfhydryl, sulfide, and carboxyl;

n is an integer selected from the group consisting of 0, 1, 2, 3, 4, and 5;

p is an integer selected from the group consisting of 0 and 1; and pharmaceutically acceptable salts thereof.

19. The method of claim 18, wherein the DNA repair enzyme is selected from the group consisting of DNA polymerase β, 5'-deoxyribose-5-phosphate lyase Ku70, and Endonuclease III-like protein 1.

20. The method of claim 18, wherein the compound inhibits the lyase activity of the DNA repair enzyme.

21. The method of claim 18, further comprising contacting the DNA repair enzyme with a DNA damaging agent.

22. The method of claim 21, wherein the DNA damaging agent is methyl methanesulfonate (MMS).

* * * * *